(12) United States Patent
Hursh et al.

(10) Patent No.: US 7,118,530 B2
(45) Date of Patent: Oct. 10, 2006

(54) INTERFACE FOR A SYSTEM AND METHOD FOR EVALUATING TASK EFFECTIVENESS BASED ON SLEEP PATTERN

(75) Inventors: Steven Rawlings Hursh, Joppa, MD (US); Timothy Elsmore, Chula Vista, CA (US); Douglas Eddy, San Antonio, TX (US)

(73) Assignee: Science Applications International Corp., San Diego, CA (US)

( * ) Notice: Subject to any disclaimer, the term of this patent is extended or adjusted under 35 U.S.C. 154(b) by 244 days.

(21) Appl. No.: 10/216,860

(22) Filed: Aug. 13, 2002

(65) Prior Publication Data

US 2003/0018242 A1    Jan. 23, 2003

Related U.S. Application Data

(63) Continuation-in-part of application No. 09/899,540, filed on Jul. 6, 2001, now Pat. No. 6,579,233.

(51) Int. Cl.
*A61B 3/00* (2006.01)

(52) U.S. Cl. ....................... 600/300; 128/920

(58) Field of Classification Search ........ 600/300–301, 600/481, 509, 515, 521, 544, 545, 595; 128/898, 128/920; 340/576, 835, 978; 700/83; 607/88, 607/19, 24, 25, 27; 514/288
See application file for complete search history.

(56) References Cited

U.S. PATENT DOCUMENTS

| 4,893,291 A | 1/1990 | Bick et al. |
| 5,006,985 A | 4/1991 | Ehret et al. |
| 5,111,391 A | 5/1992 | Fields et al. |
| 5,140,562 A | 8/1992 | Moore-Ede et al. |
| 5,270,920 A | 12/1993 | Pearse et al. |
| 5,303,170 A | 4/1994 | Valko |
| 5,323,314 A | 6/1994 | Baber et al. |
| 5,433,223 A | 7/1995 | Moore-Ede et al. |
| 5,615,138 A | 3/1997 | Tanaka et al. |
| 5,845,257 A | 12/1998 | Fu et al. |
| 5,970,466 A | 10/1999 | Detjen et al. |
| 5,970,468 A | 10/1999 | Bull |
| 6,419,629 B1 * | 7/2002 | Balkin et al. ............... 600/300 |
| 6,579,233 B1 * | 6/2003 | Hursh ......................... 600/300 |
| 6,605,038 B1 * | 8/2003 | Teller et al. ................ 600/300 |

OTHER PUBLICATIONS

P. Achermann, et al., "Combining Different Models Of Sleep Regulation", Journal of Sleep Research, 1991, pp. 144-147, 1.

(Continued)

*Primary Examiner*—Max F. Hindenburg
*Assistant Examiner*—Michael C. Astorino
(74) *Attorney, Agent, or Firm*—Banner & Witcoff, Ltd.

(57) ABSTRACT

An interface for a system and method for evaluating the effectiveness of a person to perform a task based on his/her preceding or predicted sleep pattern is provided. The interface allows a user to use actual sleep data or predicted sleep data to produce predictions of the task effectiveness of a person to perform a particular task. The predictions may be in tabular, graphical, or tabular and graphical format. The interface may also represent the effectiveness of a user based on the actual or predicted sleep data in conjunction with an actual or predicted work schedule or pattern. The results can be correlated to sunlight in the user's location, and can also account for changes in the users location (transmeridian shifts), sunlight during the user's sleep cycle (shift work), and other schedule modifying events.

4 Claims, 50 Drawing Sheets

OTHER PUBLICATIONS

T. Akerstedt, et al., "Validation of the S and C Components of the Three-Process Model of Alertness Regulation", Sleep, 1991, pp. 1-6, 19(18).

R. Angus, et al., "Effects of Sleep Loss on Sustained Cognitive Performance During a Command and Control Stimulation", Behavior Research Methods, Instruments, & Computers, 1985, pp. 55-67, 17(1).

G. Belenky, et al., "Sustaining Performance During Continuous Operations: The U.S. Army's Sleep Management System", 1996, Paper Presented At The 1996 Army Science Conference.

B. Bjerner, et al., "Diurnal Variation Of Mental Performance. A Study of Three-Shift Workers", British Journal of Industrial Medicine, 1955, pp. 103-110, 12.

A. Borbely et al., "Concepts and Models of Sleep Regulation: An overview," Journal of Sleep Research, 1992, pp. 63-79, 1.

A. Borbely et al., "Sleep Initiation and Initial Sleep Intensity: Interactions of Homeostatic and Circadian Mechanisms", Journal of Biological Rhythms, 1989, pp. 149-160, 4 (2).

M. Carskadon, et al., "Sleep Tendency: An Objective Measure of Sleep Loss", Sleep Research, 1977, 6, 200.

D. Dinges, et al. "Sleepiness Impairs Optimum Response Capability", Sleep Research, 1989, 18, 366.

S. Folkard, "Diurnal Variation In Logical Reasoning", British Journal of Psychology, 1975, pp. 1-6, 66 (1).

S. Folkard et al., "A Three Process Model Of The Regulation Of Alertness And Sleepiness", Sleep, Arousal and Performance Problems and Promises, 1991, 11, 26.

S. Folkard, et al., "Towards A Model For The Prediction Of Alertness And/Or Fatigue On Different Sleep/Wake Schedules in Contemporary Advances In Shiftwork Research", Medical Academy, 1987, pp. 231-240.

S. Folkard et al., "Shiftwork and Performance", Human Factors, 1979, pp. 483-492, 21.

J. Froberg. "Twenty-Four-Hour Patterns In Human Performance, Subjective and Physiological Variables And Differences Between Morning And Evening Active Subjects", Biological Psychology, 1977, pp. 119-134, 5.

R.C. Graeber, "Recent Studies Relative To The Airlifting Of Military Units Across Time Zones", Chronobiology: Principles and Applications to Shifts in Schedules, 1980, pp. 353-370.

W. Harris, "Fatigue, Circadian Rhythm and Truck Accidents in Vigilance", 1977, pp. 133-147.

P. Hamelin, "Lorry Drivers Times Habits in Work and Their Involvement in Traffic Accidents", Ergonomics, 1987, pp. 1323-1333, 30.

Haus et al., "The Circadian Time Structure", Chronobiology: Principals & Applications to Shifts in Schedules, 1980, pp. 47-94.

S. Hursh, et al., "Modeling Human Performance To Predict Unit Effectiveness", Army Science: The New Frontiers, Military and Civilian Applications, Saratoga, 1993, pp. 309-328.

K. Klein, et al., "Air Operations and Circadian Performance Rhythms", Aviation Space and Environmental Medicine 1976, pp. 221-229, 47(3).

Klein et al., "The Effect of Transmeridian and Transequitorial Air Travel on Psychological Well-Being and Performance", Chronobiology: Principles and Applications to Shifts in Schedules, 1980, pp. 339-352.

J.T. Klopcic, "The AURA Fatigue and Heat Stress Algorithms", (Unclassified): Ballistic Research Laboratory Technical Report BRL-MR-3802, 1989.

R. Kronauer, "A Model for the Effect of Light on the Human "Deep" Circadian Rhythm" Sleep Research, 1982, 16, 620.

P. Lavie, "The 24-hour sleep propensity function (SPF): Practical and theoretical implications", Sleep, Sleepiness and Performance, 1991, pp. 65-93.

P. Lavie, "To Nap Perchance to Sleep—Ultradian Aspects of Napping," Sleep and Alertness: Chronobiological, behavioral, and medical aspects of Napping, 1989, pp. 99-120.

M. Mitler et al., "Multiple Daytime Nap Approaches to Evaluating The Sleepy Patient", Sleep 5, 1982, pp. 119-127.

T. Monk, "Circadian Aspects Of Subjective Sleepiness: A Behavioral Messenger?" Sleep, Sleepiness and Performance, 1991, pp. 39-63.

T. Monk, "Subjective Ratings Of Sleepiness: The Underlying Circadian Mechanisms", Sleep 10, 1987, pp. 343-353.

T. Monk, "The Arousal Model of Time of Day Effects in Human Performance Efficiency", Chronobiologia, 1982, pp. 49-54.

T. Monk et al., "A Field Study of Circadian Rhythms in Actual and Interpolated Task Performance" in Night and Shift Work: Biological and Social Aspects, 1981, pp. 473-480.

J. Ribak et al., "Diurnal Rhythmicity and Airforce Flight Accidents Due to Pilot Error", Aviation, Space and Environmental Medicine, 1983, pp. 1096-1099, 54.

D. Richardson, et al., "Excessive Daytime Sleepiness in Man: Multiple Sleep Latency Measurement in Narcoleptic and Control Subjects", Electroencephalography and Clinical Neurophysiology, 1978, pp. 621-627, 45.

E. Voigt, Int. Z. angew. Physiol. Einschl. Arbetisphysiol., 1968, pp. 1-12, 25.

R. Wever, "Mathematical Models of Circadian One- and Multi-Oscillator Systems", Lect. Math Life Science, 1987, pp. 205-265, 19.

R. Wever, "Use of Light To Treat Jet Lag: Differential Effects of Normal and Bright Artificial Light on Human Circadian Rythms", Annual NY Academy Science, 1985, pp. 282-304, 453.

R. Wilkinson, "Effects Of Up To 60 Hours Of Sleep Deprivation On Different Types Of Work", Ergonomics, 1964, pp. 175-186, 17.

International Search Report, Int'l. Appl. No. PCT/US03/23263.

Steven R. Hursh, "Fatigue and Alertness Management Using FAST", Internet Article, Jul. 6, 2001, 52 pages.

* cited by examiner

FAST Rationale

The technologies of modern air warfare have largely eliminated the constraints of night and day. Aircraft guidance systems and smart munitions permit us to exploit the cover of night. Mid-air refueling methods permit long duration flights that can take aircraft halfway around the world and back. It is tempting, then, for commanders to plan operations that exploit these systems for maximum surprise and intensity. Nevertheless, air operations still require the participation of human pilots, controllers, and ground support personnel. The human brain cannot function for long periods of time without severe degradation nor is it immune to variations in attention produced by day and night conditions. Fatigue is well known to degrade performance; and while countermeasures can temporarily extend the performance of crews under unusual circumstances, in the long run there is no substitute for adequate sleep to refresh mental capacity.

A great deal of research has been done to study the limits of human performance under sleep deprivation and experts can advise on how to best utilize crew members to avoid the disruptions of day-night rhythms and fatigue. Unfortunately, there is currently no system that permits the military planner to automatically consider the lessons of sleep and performance research when planning flight operations. The FAST program uses a newly-developed computer model (the SAFTE model) of human sleep and performance as the basis of a fatigue avoidance decision aid for operational planning. This scheduling system permits a planner to evaluate the relative benefits of various schedules that accomplish a mission. With this computerized system, optimal performance can be arranged at critical times and degradations can be avoided, scheduled at times of minimal workload, or at times when they will potentially have the least impact.

See: *Circadian rhythms*

INTERFACE FOR A SYSTEM AND METHOD FOR EVALUATING TASK EFFECTIVENESS BASED ON SLEEP PATTERN

RELATED APPLICATIONS

The present application is a continuation-in-part application of Ser. No. 09/899,540, now U.S. Pat. No. 6,579,233 B2, filed Jul. 6, 2001, entitled a System and Method for Evaluating Task Effectiveness Based on Sleep Pattern.

BACKGROUND OF THE INVENTION

1. Field of the Invention

The present invention relates to an interface for a system and method for evaluating the effectiveness of a person to perform a task based on his/her preceding or predicted sleep pattern. More particularly, the present invention relates to an interface for a system and method for evaluating task effectiveness that allows the user to use actual sleep data or predicted sleep data to produce predictions of the task effectiveness of a person to perform a particular task.

2. Background of the Invention

Numerous studies have been conducted relating to the analysis of sleep, alertness, and performance. One study is by Jewett and Kronauer, entitled "Interactive Mathematical Models of Subjective Alertness and Cognitive Throughput in Humans," *J. Biological Rhythms,* 1999; 14(6): pages 588–597. The Jewett and Kronauer model (JK model hereafter) uses arbitrary units and then scales the result from 1 to 0 to fit the actual data, scaled from maximum to minimum. Consequently, the JK model does not make an independent prediction of performance without knowing the range of the results.

Prior studies and patents do not provide an easy-to-use interface for a system of evaluating the effectiveness of a person to perform a specific task based on his or her previous sleep pattern. The prior studies and patents are directed to general concepts and do not provide an individual with an easy-to-use interface or system in which actual historic data or predicted future data can be input, and adjustments to future sleep patterns can be made to control the effectiveness of a person to perform a task. In addition, the prior studies and patents are not designed to utilize both actual sleep data or predicted sleep data to predict future changes in task effectiveness based upon the actual or predicted pattern of sleep and activity taking into account many complex factors that contribute to the sleep experience.

SUMMARY OF THE INVENTION

The forgoing and other deficiencies are addressed by the present invention, which is directed to an interface for a system and method for evaluating the effectiveness of a person to perform a task based on his/her previous or predicted sleep pattern. The interface allows a user to predict changes in task effectiveness at any time of day, based upon numerous patterns of sleep and activity (wakefulness), either experienced or planned for the future. The interface allows the user to take into account progressive increases in sleep deprivation (fatigue), the effects of the time of day (circadian rhythms) on performance, and changes in the time when a person sleeps and works (shift work and trans-meridian phase shifts). Numerous sleep-related factors can be manipulated through the interface to produce predictions of task effectiveness.

The interface provides both graphical and tabular outputs. The interface can be used to schedule sleep and wake periods relative to specific tasks depending on the skills required for the task. The interface can be used to anticipate the detrimental effects of jet lag, the beneficial effects of naps, the variations in performance and attention due to circadian rhythms, the variations in sleep quality with time of day and environmental conditions, the safest times to perform difficult tasks, and to help determine when to take sedatives or stimulants, if needed. All of the foregoing factors can be manipulated through the interface.

BRIEF DESCRIPTION OF THE DRAWINGS

These and other attributes of the present invention will be described with respect to the following drawings in which:

FIG. 23 is a screen showing a schedule information box for the interface for the system for evaluating the effectiveness of a person to perform a task according to the present invention;

FIG. 30 is an edit schedule properties screen of the interface for the system for evaluating the effectiveness of a person to perform a task according to the present invention;

FIG. 49 is a help screen displayed by selecting the fatigue avoidance tool (FAST) option from the screen shown in FIG. 48, for the interface for the system for evaluating the effectiveness of a person to perform a task according to the present invention;

FIG. 54 is a knowledge base menu, accessed from the help menu screen shown in FIG. 48 according to the present invention.

DETAILED DESCRIPTION OF THE INVENTION

Figure 1:
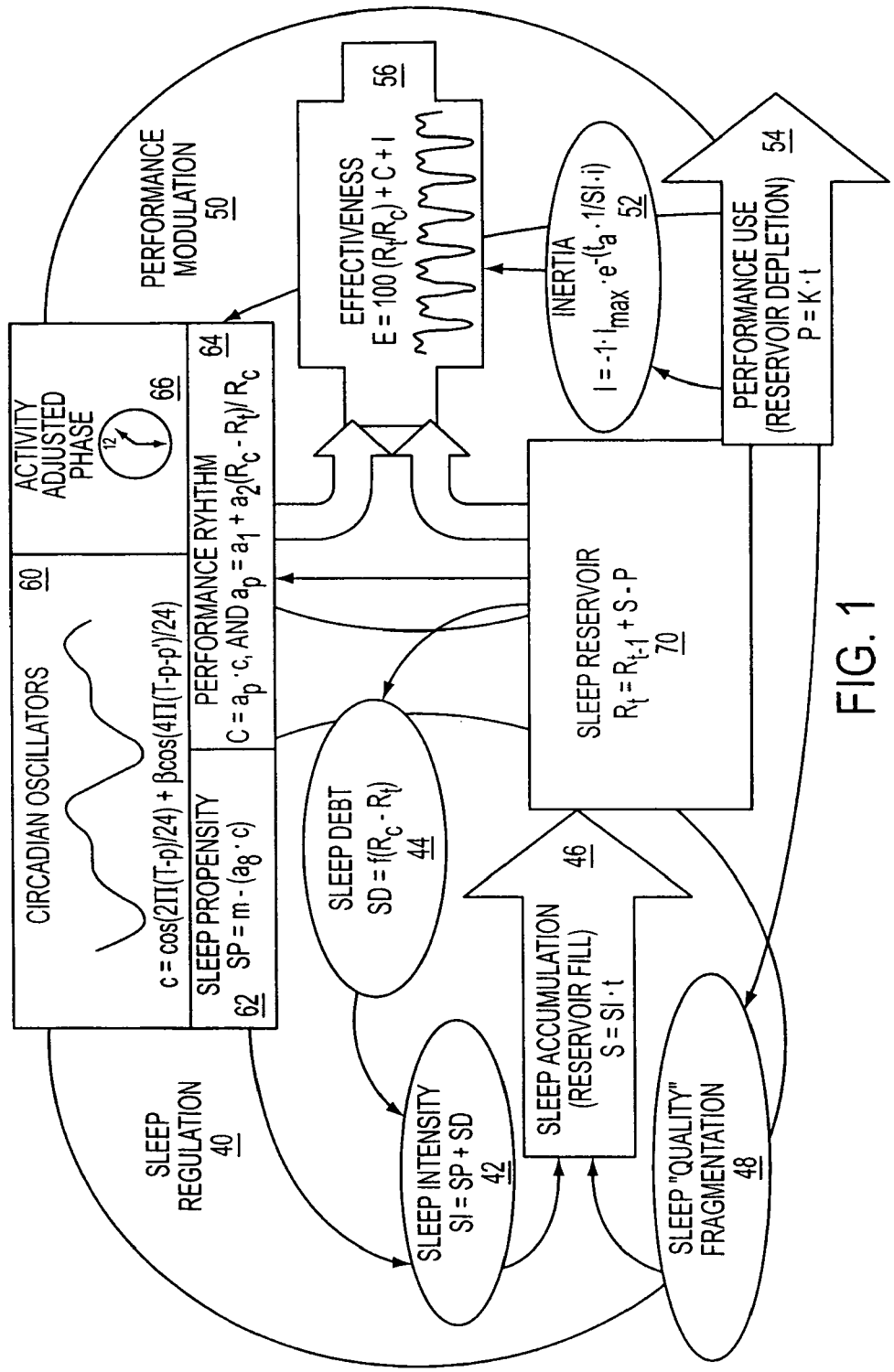
FIG. 1 shows a method and system for evaluating the effectiveness of a person to perform a task according to the present invention.

The method and system for evaluating the effectiveness of a person to perform a specific task accessed through the interface of the present invention, is illustrated in FIG. 1. A user can employ the system to predict modulation of performance based on regulation of a sleep pattern. The factors utilized to regulate sleep are broadly indicated in the sleep regulation section 40, shown in FIG. 1. These factors include sleep intensity 42, sleep debt 44, sleep accumulation 46, and sleep quality or fragmentation 48. Performance modulation section 50 contains factors that are used for such performance modulation, including circadian rhythm 64, sleep inertia 52, effectiveness 56 and performance use 54, as shown in FIG. 1.

A circadian process 60 influences both the performance modulation 50 and sleep regulation 40. Sleep regulation 40 is dependent on the hours of sleep and wakefulness, current sleep debt, the circadian process, which is represented by the circadian oscillators 60, and fragmentation 48, namely awakenings during periods of sleep. Performance modulation 50 depends on the current balance of the sleep reservoir, the circadian process, and sleep inertia. Through the implementation of mathematical modeling the system and method of the present invention can predict changes in cognitive performance. One embodiment of the present invention makes use of a multi-oscillator circadian process, a circadian sleep propensity process, a sleep fragmentation process, and a circadian phase adjusting feature for time zone changes. These processes can be implemented on a general-purpose digital computer.

Performance while awake and the drive to sleep are both controlled, in part, by a circadian process 60. Numerous studies of performance, reaction time, alertness ratings, measures of the tendency to fall asleep, and body temperature indicate that the underlying circadian process is not a simple sine wave. Performance and alertness reach a major peak in the early evening, about 2000 hours, and fall to a minimum about 0400 hours. There is a secondary minimum in the early afternoon, about 1400 hours, and a morning peak at about 1000 hours. Correlated with this pattern is a rising tendency to fall asleep that reaches a peak at about the same time performance and alertness reach a minimum. The existence of both a major and a minor peak in performance and two corresponding minima at other times, suggest that at least two oscillators are involved in the circadian process. These multiple oscillators are accounted for in the method for evaluating the effectiveness of the present invention.

Figure 2:
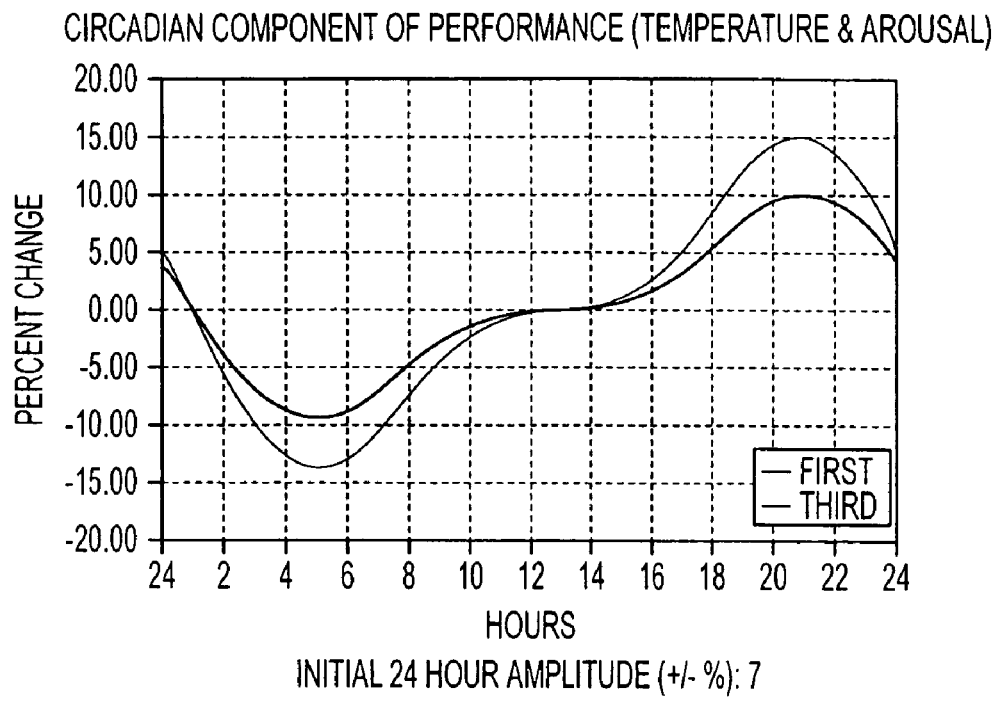
FIG. 2 is a graph illustrating a complex circadian oscillator using units of percent change in effectiveness.

One embodiment of the present invention incorporates a circadian process that is composed of the sum of two cosine waves, one with a period of 24 hours, and one with a period of 12 hours. The two sinusoidal oscillators are out of phase thereby producing a predicted variation in arousal that closely parallels known patterns of body temperature. Referring to FIG. 2, a graph of the complex circadian oscillator is illustrated using units of percent change in effectiveness in one variation of the invention.

The circadian process within the method for evaluating the effectiveness generates an arousal function that mirrors circadian changes in oral temperature. This arousal oscillator drives both variations in predicted cognitive effectiveness and sleep propensity. These two translations of the oscillator have identical frequency and phase components and differ only in amplitude and sign; a rise in arousal produces an increase in performance and a decrease in propensity to sleep. The circadian process 60 is depicted in FIG. 1.

The control of sleep and the influence of sleep on cognitive capacity is a homeostatic process. At the center of the homeostatic process is the sleep reservoir 70, shown in FIG. 1. A fully rested person has optimal performance capacity, indicated as the reservoir capacity $R_c$. While awake, the reservoir is depleted according to a performance use function, indicated by the arrow 54 pointing away from the reservoir 70. While asleep, the reservoir is filled to replenish the capacity to perform and be alert as indicated by the arrow 46 representing sleep accumulation. The rate of accumulation for each minute of sleep is called sleep intensity, and is driven by two factors: 1) the circadian variation in sleep propensity 62, and 2) the current sleep deficit 44, which is the reservoir capacity $R_c$ minus the current level of the reservoir $R_t$ at time t. This deficit is constantly changing as a person sleeps and replenishes the reservoir 70, or is awake and depletes the reservoir 70. The effectiveness 56 is determined from the circadian oscillators 60 and performance rhythm 64, the sleep reservoir 70, and the sleep inertia 52.

The circadian oscillators 60 are represented by the following equation:

$$c = \cos(2\Pi(T-p)/24) + \beta \cos(4\Pi(T-p-p')/24),$$

where T=time of day, p=24 hr phase in hours, p'=12 hr relative phase in hrs, and $\beta$=rel. amplitude of 12 hr cycle.

The sleep propensity is represented by the following equation:

$$SP = m - (a_s \cdot c)$$

where m=mesor (a point around which a sine wave oscillates), and $a_s$=sleep propensity amplitude.

The performance rhythm is represented by the following equation:

$$C = a_p \cdot c$$

where $a_p = a_1 + a_2(R_c - R_t)/R_c$, performance rhythm amplitude.

The connection of the sleep reservoir to the sleep debt calculation 44 forms a feedback loop with the sleep intensity 42, the sleep accumulation 46, and back to the sleep reservoir 70. The sleep debt is represented by the following equation:

$$SD = f(R_c - R_t),$$

where $R_c$=Reservoir Capacity, $R_t$=Current Reservoir Balance, $(R_c - R_t)$=Current Reservoir Deficit, and f=amplitude of feedback.

The reservoir balance of the sleep reservoir 70 is represented by the following function:

$$R_t = R_{t-1} + S - P, \text{ and represents the total sleep units at time interval t.}$$

The sleep intensity 42 is represented by the following equation:

$$SI = SP + SD, \text{ in sleep units per minute, } SI \leq SI_{max}$$

The sleep inertia 52 is represented by the following equation:

$$I = -1 \cdot I_{max} \cdot e^{-(ta \cdot 1/SI\ 1)},$$

where max=$I_{max}$, and i=inertia time constant for two hr after awakening.

The sleep accumulation 46 is represented as:

$$S = SI \cdot t,$$

Where t=time interval.

Sleep fragmentation 48 caused by a poor quality sleep environment results in a pause in sleep accumulation after returning to sleep following each awakening from a sleep interval.

The performance use 54 can be represented by the following linear equation:

$$P = K \cdot t,$$

where K=performance use rate.

The prediction of the model is cognitive effectiveness 56 interpreted as percent of baseline cognitive throughput and calculated by the equation:

$$E = 100(R_t/R_c) + C + I$$

Table 1 shows the default values for the variables in the foregoing equations.

TABLE 1

SAFTE Model parameters and default values.

| Parameter: | Default Value: |
| --- | --- |
| p = 24 hr component phase in hours | 1700 hrs initially, adjusts to 3 hr after average awake hour according to algorithm described in Attachment B. |
| p' = 12 hr component relative phase in hrs | 3 hrs earlier than p |
| β = relative amplitude of 12 hr cycle | 0.5 |
| m = sleep propensity mesor | 0 |
| $a_s$ = sleep propensity amplitude | 0.55 sleep units |
| $a_1$ = constant performance rhythm amplitude factor | 7 percent |
| $a_2$ = variable performance rhythm amplitude factor | 5 percent |
| $R_c$ = Reservoir Capacity | 2880 sleep units - units required for 4 days continuous awake |
| f = amplitude of feedback | 0.0026243 |
| $SI_{max}$ = maximum sleep unit accumulation per min | 4.4 units per min |
| Sleep fragmentation pause in sleep accumulation | 5 min delay after start of new sleep interval |
| i = inertia time constant for two hr after awakening | 0.04 |
| $I_{max}$ = maximum inertia following awakening | 5 percent |
| K = performance use rate | 0.5 units per minute |
| t = time interval | 1 minute |
| $t_a$ = time awake | Minutes since awakening |

Figure 14:
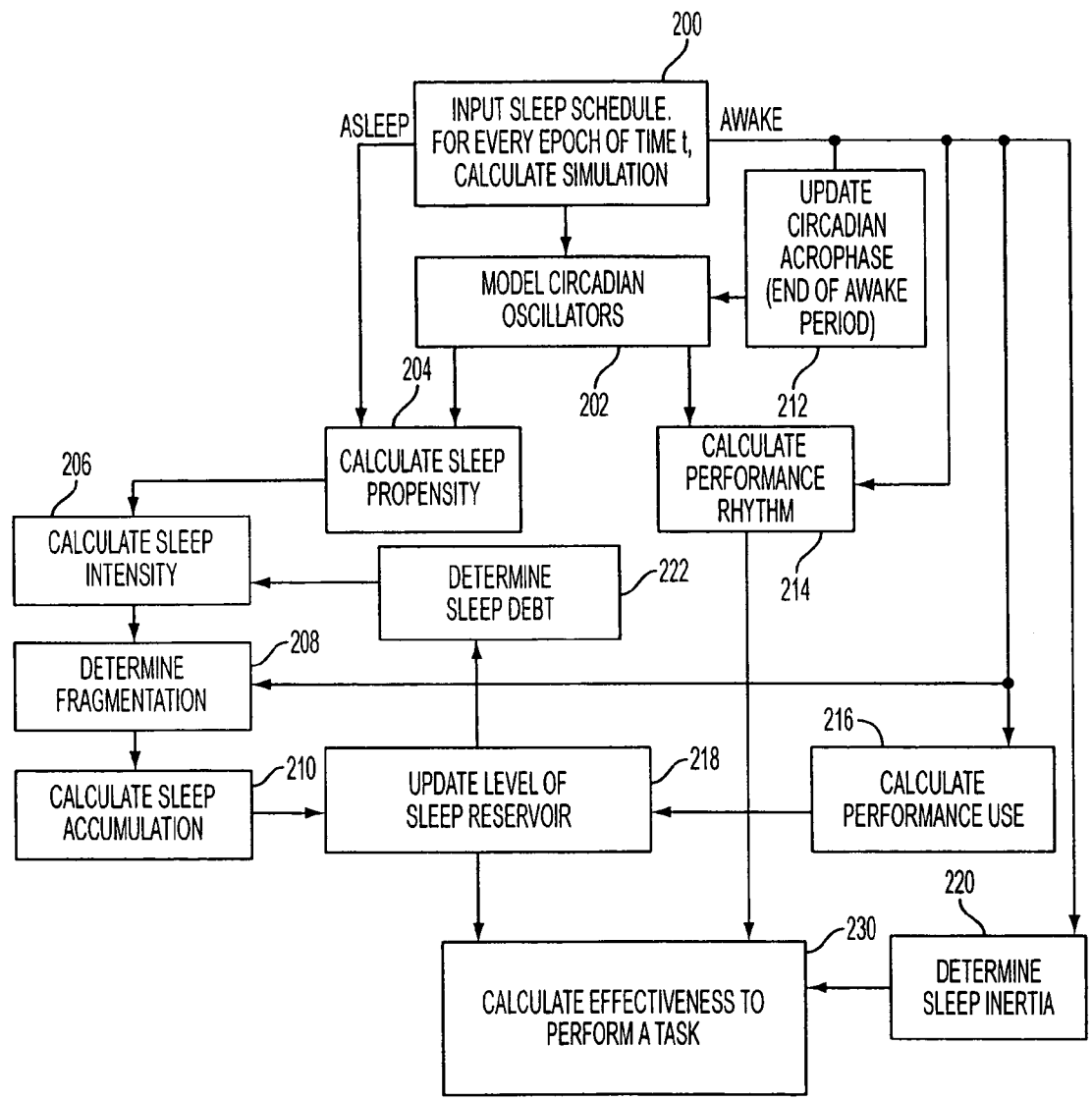
FIG. 14 is a flow chart of a method for evaluating the effectiveness of a person to perform a task according to the present invention.

A method according to the present invention is also illustrated in the flow chart shown in FIG. 14. In step 200 the sleep schedule (past and/or future) is input to the simulation. At each time epoch, t, of the schedule, the sleep state (asleep or awake) is determined and the simulation is updated accordingly. In step 202 the circadian oscillators are modeled. When asleep, the circadian oscillators are used to calculate the sleep propensity 204, which partly determines sleep intensity in step 206. After any pause caused by fragmentation 208, sleep accumulation is calculated in step 210, which is used to update the amount of effective sleep in the sleep reservoir 70 in step 218. The sleep debt is determined in step 222 based on the sleep reservoir calculated in step 218 and is used in step 206 to calculate the sleep intensity. When awake, performance use is calculated in step 216 and also triggers a sleep fragmentation determination in step 208. At the start of each awake period, sleep inertia is calculated in step 220 and contributes to the cognitive effectiveness calculation at 230. The sleep inertia from step 220, the amount of effective sleep in the reservoir 70, calculated in step 218, and the circadian oscillators, modeled in step 202, are used to calculate the performance rhythm at step 214, are all used to calculate the effectiveness to perform the task in step 230. Steps 218, 222, 206, 208 and 210 form a feedback loop.

Figure 3:
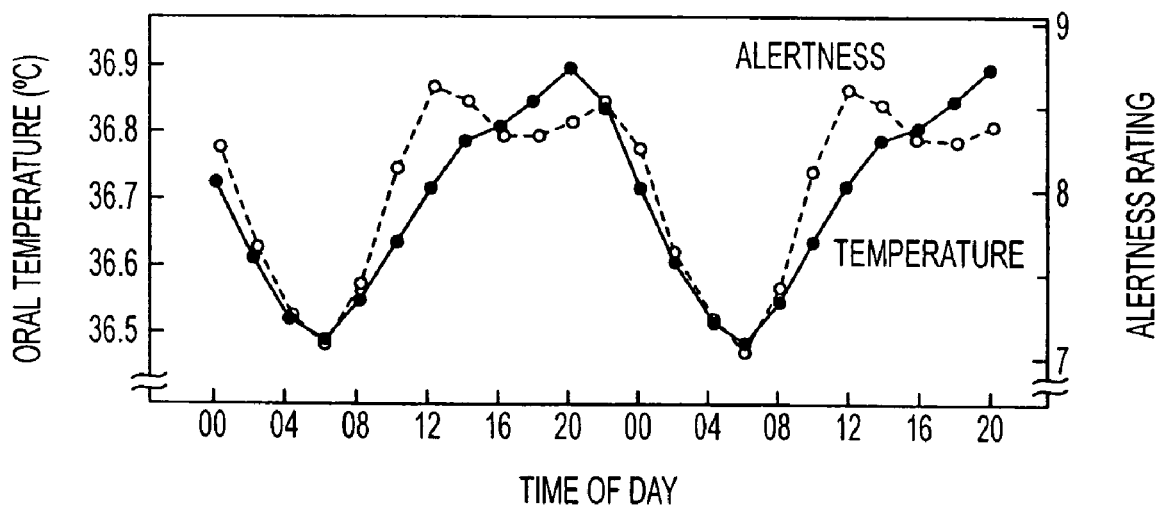
FIG. 3 is a graph illustrating circadian rhythm in oral temperature and substantive alertness.

FIG. 2 is a graph representing circadian oscillation in performance corresponding to the temperature and arousal rhythm as a function of the time of day. The arousal oscillator 60 drives both variations in predicted performance (cognitive effectiveness) and sleep propensity. These two translations of the oscillator have identical frequency and phase components and differ only in amplitude and sign. A rise in arousal produces an increase in performance and a decrease in propensity to sleep. FIG. 2 illustrates an inventive simulation of the performance rhythm for the first day of a fully rested person and after three days of sleep deprivation. The amplitude of the performance rhythm increases with the accumulated sleep debt on the third day. As can be seen in FIG. 3, the circadian rhythm, as represented by oral temperature, and the subjective alertness are closely related, but not identical since alertness and performance are also sensitive to level of the sleep reservoir. The oscillation in the reservoir level is called the sleep-wake cycle and represents the current sleep debt ($R_c - R_t$). Sleep accumulation does not start immediately upon retiring to sleep. Following a period of wakefulness there is a minimal delay of approximately 5 minutes required to achieve a restful sleep state. This factor accounts for the penalty during recuperation that is caused by sleep in an environment that leads to frequent interruptions. These components of the sleep accumulation function are indicated as 42 and 48, respectively, in FIG. 1, to the left of the sleep reservoir 70 feeding into the sleep accumulation function 46.

The level of the reservoir 70 at time t+1 is the level at time t, $R_t$, plus sleep accumulation (S) while asleep and minus performance use (P) while awake. The units of the reservoir 70 are minutes of effective sleep. The method of the present invention can easily accommodate a complex pattern of sleep and waking. While asleep, the simulation adds to the reservoir 70; while awake the simulation depletes the reservoir 70. A schedule can oscillate between these states as often as once a minute and the simulation will keep account of the net effects on performance capacity as the balance in the reservoir 70, similar to the balance in a check book.

The total reservoir capacity is 2880 units (nominal minutes) of effective sleep. This value is based on the following considerations. The average person is assumed to require 8 hours of sleep and is awake for 16 hours in the typical day. To remain in balance, then, sleep units must accumulate at twice the rate it is used during performance. Hence, the rate of performance use, κ, is 0.5 relative to the average rate of sleep accumulation. Studies of total sleep deprivation indicate that cognitive capacity depletes at a rate of about 25% per day. Hence, the reservoir has the capacity to sustain performance for four days. This translates into 2880 units of sleep: 4 days×24 hours×60 min/hr×0.5.

The outcome of the reservoir process, according to the method of the present invention, during continuous sleep converges to an exponential accumulation function, if one ignores the circadian effects on sleep intensity. One embodiment of the method of the present invention is based on minute-by-minute additions to the reservoir 70 during sleep, with the size of these increments proportional to the reservoir deficit (the feedback process). Integrated over time, this iterative process is described by an approximate exponential function, but is not an exponential function; rather, it is a moment-by-moment simulation of the effects of sleep on the reservoir balance. Therefore, the method can easily accommodate a momentary interruption in sleep (fragmentation) caused by a poor quality sleep environment. The incremental process is interrupted for the duration of the awakening and the reservoir 70 is depleted for that period of time by the performance function. Upon return to sleep after an interruption, there is a delay before resumption of sleep accumulation, with the delay set at 5 min in one embodiment of the method. The result of this process is directly tied to real world events that drive the process, not to an a priori mathematical equation.

The feedback process of the method of the present invention is used to determine the effects of long schedules of less than optimal sleep. Such schedules deplete the reservoir 70, and increase the intensity of sleep when sleep occurs. Eventually, the greater average intensity of sleep permits the person to adjust to such a schedule and find a new equilibrium of sleep and stable performance, within limits. Performance will not be as effective as it might be with a full eight hours of sleep, but performance does not necessarily degrade indefinitely. This is what is meant by a homeostatic sleep and performance process. It is much like a person adjusting to a restricted diet; the person loses weight and conserves energy so that a new equilibrium stable weight is reached under the limited input of calories.

According to the method of the present invention, cognitive effectiveness and alertness are primarily dependent on variations in the two processes just described: the endogenous circadian rhythm (reflected in body temperature) and current sleep reservoir balance resulting from the sleep-wake cycle. A third factor is a temporary disturbance in performance that may occur immediately following awakening, called sleep inertia I.

The variations in measured alertness, shown in FIG. 3 as a dashed line, do not exactly match the variations in oral temperature. This is because, according to one aspect of the present invention, simulated cognitive effectiveness is computed as the sum of these three factors: the relative level of the sleep reservoir in percent units (100×Rt/Rc) plus the effects of the circadian oscillator, C, and minus sleep inertia, I. Sleep inertia is represented as an exponential decay function of sleep intensity at the time of awakening and lasts for at most 2 hours.

The predictions are normally in terms of changes in cognitive effectiveness, expressed as percent of baseline performance for a person when well rested. This measure corresponds to performance of a standard serial add-subtract task or the average of a range of standard cognitive tests, described below in greater detail. In addition, the parameters of the performance calculation can be adjusted to predict other components of performance, such as reaction time, lapses in attention, and target error.

The method of the present invention can be used to make a number of predictions, such as for example, performance and alertness. The average person is assumed to require eight hours of sleep per day to be fully effective and to avoid accumulation of sleep debt. Based on the joint interaction of the endogenous circadian oscillator, c, and the sleep-wake cycle, performance is predicted to have two peaks in percent effectiveness at approximately 1000 hours and 2000 hours, a minor dip in performance at about 1400 hours, and a major trough in effectiveness during the early morning hours when the person is normally asleep.

Figure 4:
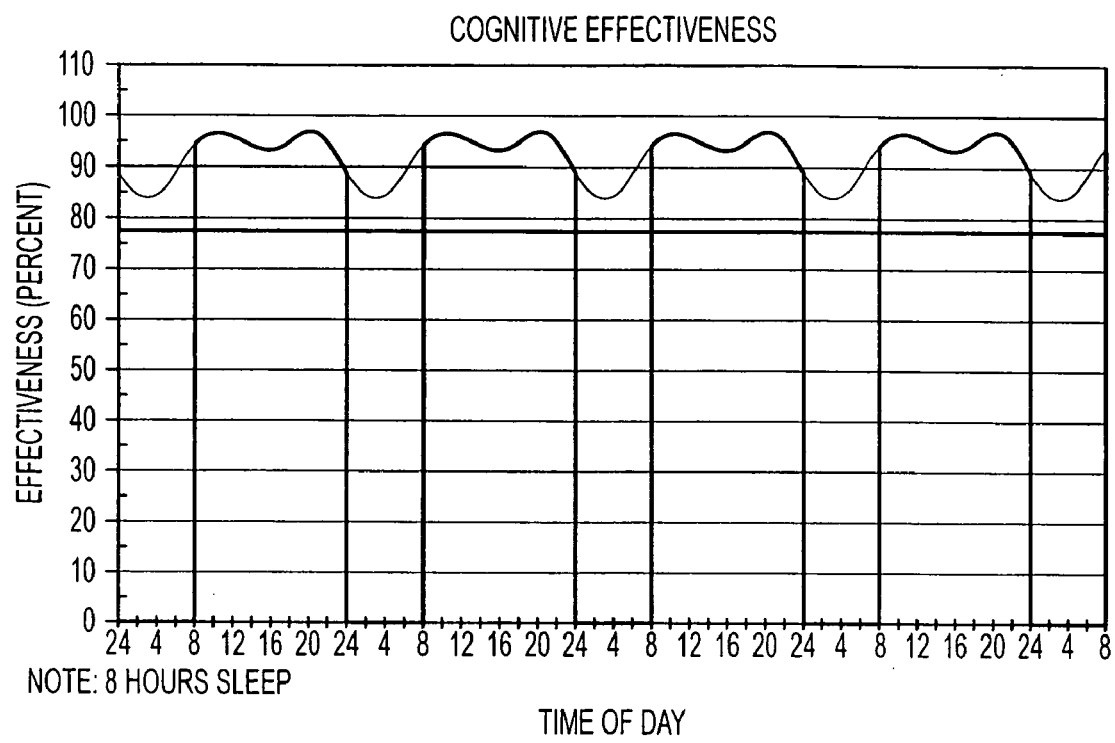
FIG. 4 is a graph illustrating the predicted variations in performance for a person sleeping eight hours per day from midnight to 0800 hours according to one variation of the present invention.

FIG. 4 displays the predicted variations in performance for a person sleeping eight hours per day from midnight to 0800 hours, heavy line. Since the individual is asleep between midnight and 0800, predicted performance is shown as a fine line indicating potential effectiveness, if awake. The nighttime pattern reveals a major trough in performance at about 0300 hours and a minor trough in performance at about 1400 hours. Referring to FIG. 3, the empirical pattern of alertness closely parallels the prediction of the method of the present invention with two peaks in alertness, a mid-afternoon dip in alertness, and a major trough in alertness at 0600 hours. Note that what is important is the pattern of performance and alertness, not the exact time of peaks and troughs, which is a parameter of the model.

Figure 5:
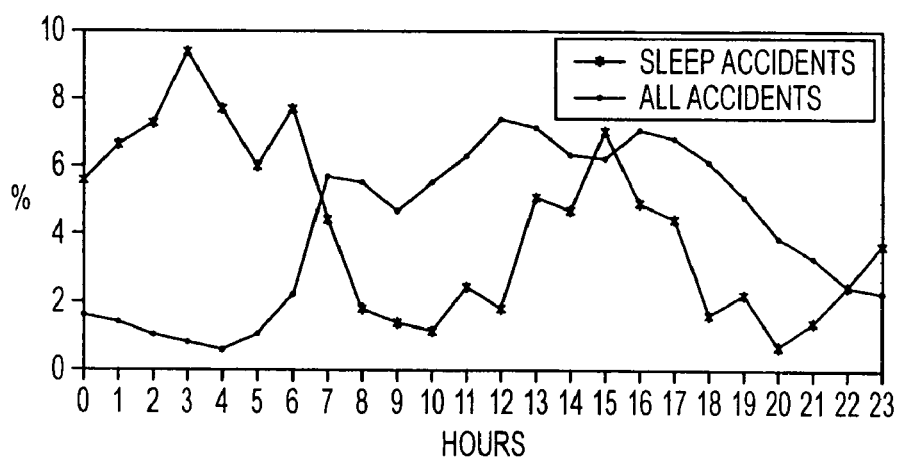
FIG. 5 is a graph illustrating hourly distribution of traffic accidents in Israel caused by falling asleep while driving, for six years, 1984–1989, in comparison with all traffic accidents.

A number of studies agree with the bimodal pattern of performance shown in FIGS. 3 and 4. Lavie (1991) reported the results of a study of sleep related traffic accidents in Israel between 1984 and 1989. In FIG. 5, the connected stars reveal two peaks in sleep related accidents, a major peak at about 0300 hours and a minor peak at about 1500 hours in the afternoon. These correspond to the dips in performance predicted by the model in FIG. 4.

Figure 6:
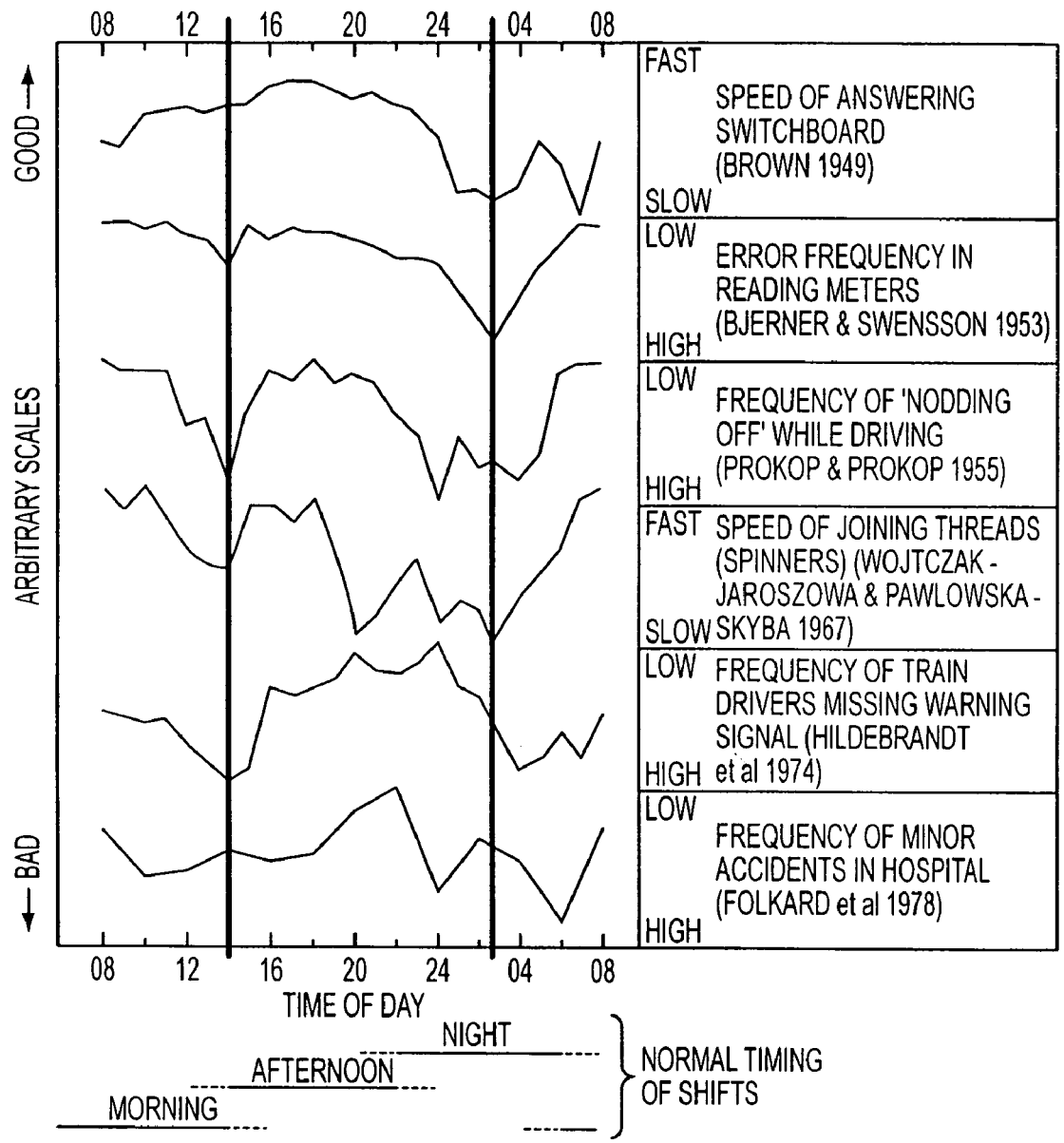
FIG. 6 is graph illustrating circadian rhythm of various industrial activities.

FIG. 6 shows the results from a variety of studies of performance from industrial settings. All performances are scaled so that "good" performance was high on the y-axis and "bad" performance was low on the y-axis. Generally, there were two dips in performance, one at about 0300 hours and a second at about 1400 hours. All these results are consistent with the predictions of the model shown in FIG. 4.

Figure 7:
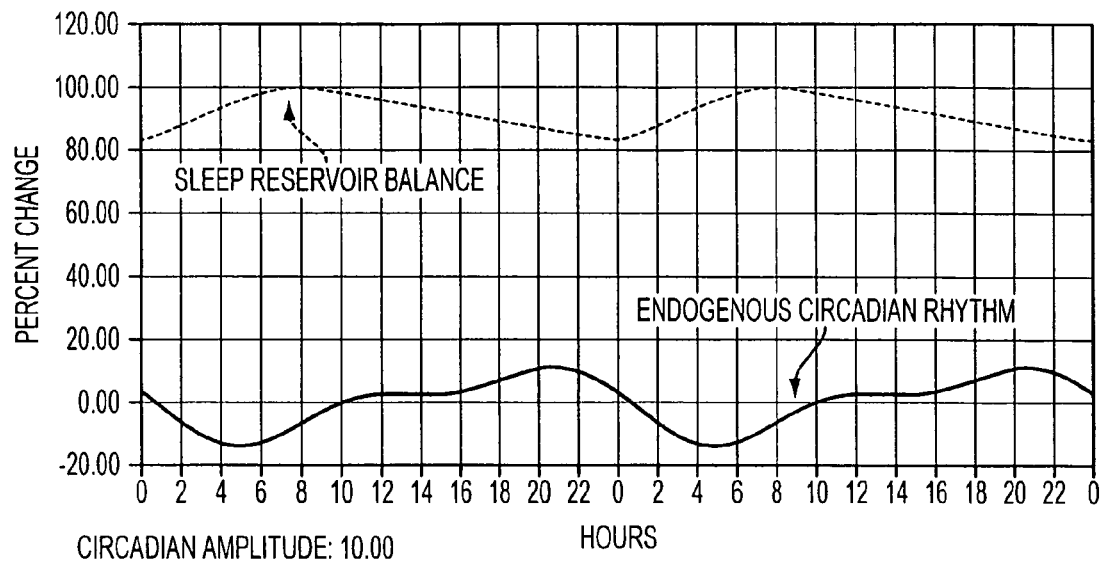
FIG. 7 is a graph illustrating constituents of performance rhythm—sleep reservoir balance and endogenous circadian rhythm of temperature and arousal according to one variation of the present invention.

The basis for the performance pattern shown in FIG. 4 is illustrated in FIG. 7. Within the model, performance is the sum of two major factors, the oscillation of the sleep reservoir balance, top curve, and the oscillation of the circadian arousal process, bottom curve. The two curves are roughly in phase so that as sleep debt is accumulated while awake (top curve), the circadian arousal process is increasing and largely offsets the change in performance. Performance is not perfectly constant, however, for two reasons. First, the two processes are not exactly in phase and this causes a strong early morning trough when the two cycles are both decreasing. Second, the temperature rhythm displays an afternoon plateau and is responsible for the mid-afternoon dip in performance when sleep debt accumulates while temperature is roughly constant.

Figure 8:
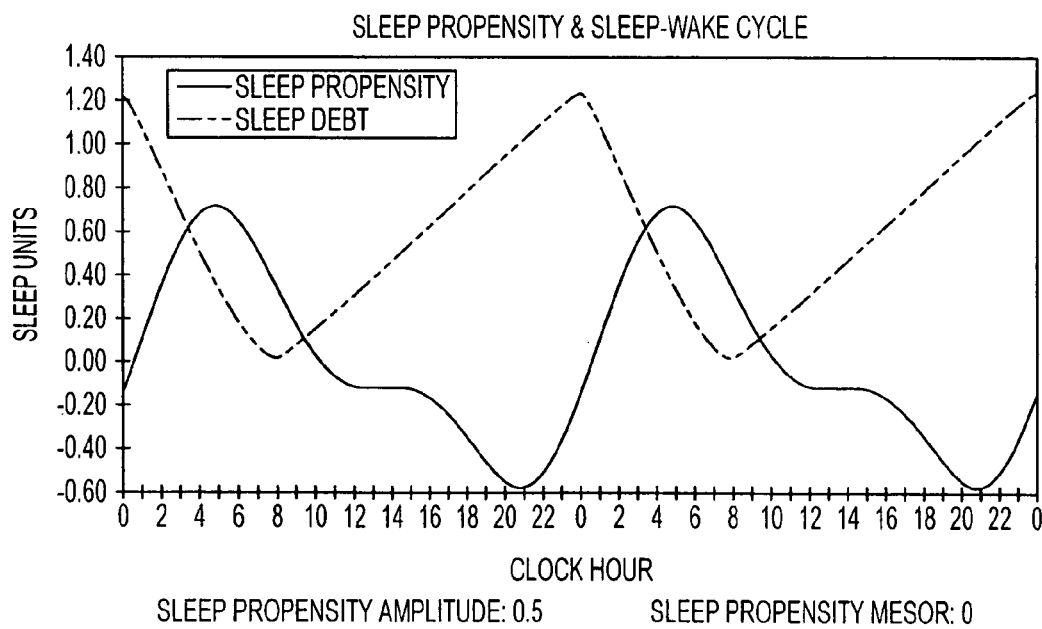
FIG. 8 is a graph showing circadian sleep propensity and sleep debt, according to one variation of the present invention.

As described earlier, the circadian process produces an oscillation in sleep propensity, shown as the solid line in FIG. 8. This rhythm is the negative of the arousal rhythm shown in FIG. 2 and scaled in sleep units. Sleep propensity SP combines with the current sleep debt SD resulting from the sleep-wake cycle, shown as the dashed line in FIG. 8.

Figure 9:
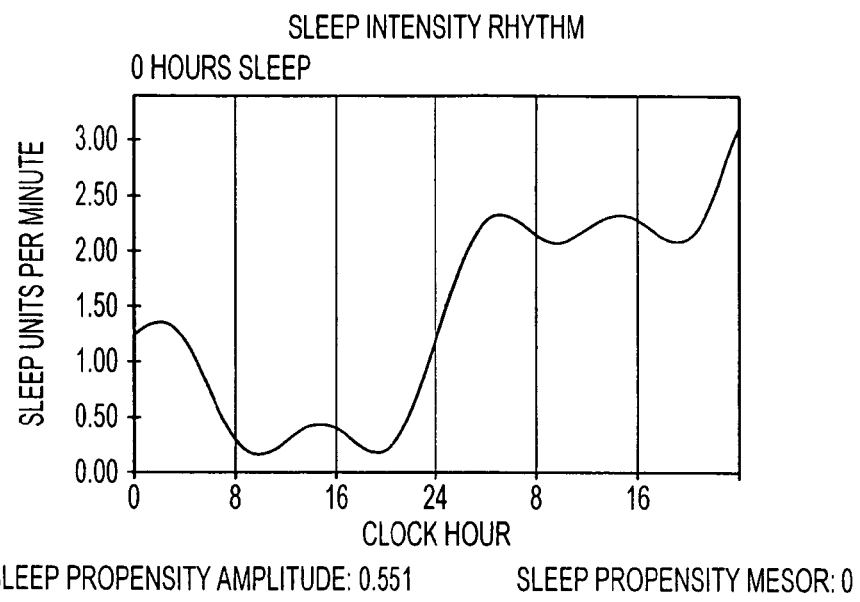
FIG. 9 is a graph illustrating sleep intensity, according to one variation of the present invention.

The summation of this sleep-wake cycle and the circadian process is called sleep intensity SI and is diagrammed in FIG. 9. For a person taking a normal 8 hours sleep from midnight to 0800 hours, sleep is most intense in the early morning at about 0300 hours. There is a mid-afternoon increase in sleep propensity at about 1500 hours that coincides with the mid-afternoon dip in alertness, FIG. 3, and increases in sleep related traffic accidents, FIG. 5.

Figure 10:
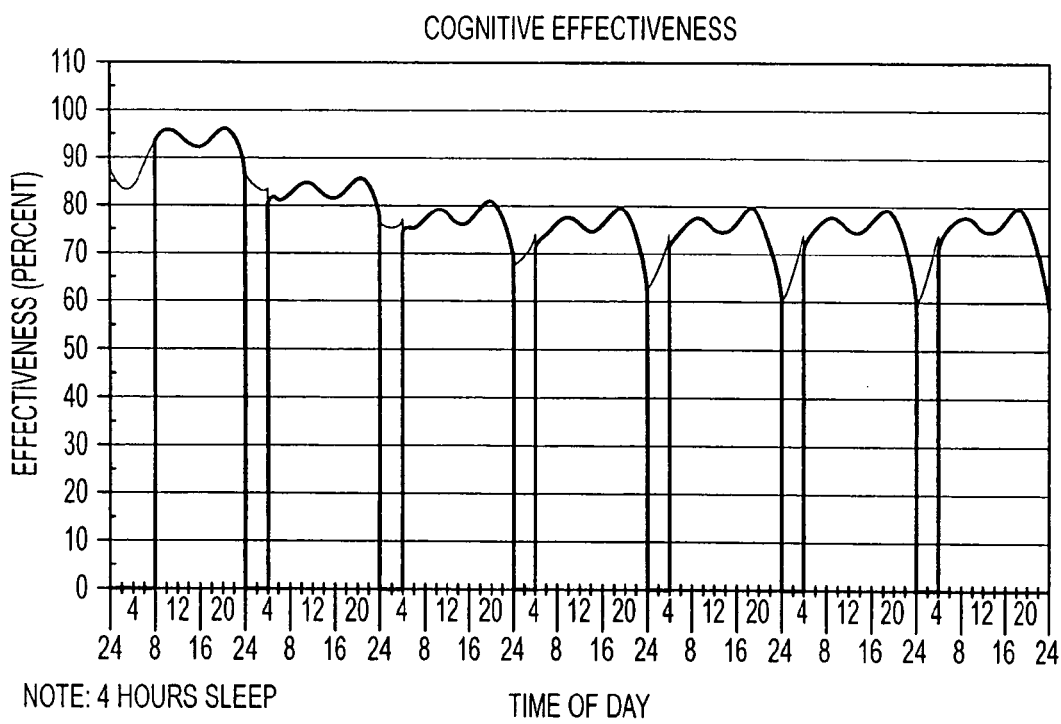
FIG. 10 is a graph illustrating sleep and predictions of cognitive effectiveness with four hours of sleep per night, according to one variation of the present invention (the heavy line is performance while awake)

The method for evaluating effectiveness according to the present invention can be used to predict equilibrium states. A homeostatic representation of sleep regulation leads to an important implication that is seldom recognized. If a subject is scheduled to take less than an optimal amount of sleep each night, for example, four hours per day, the reservoir 70 initially loses more units during the awake period than are made up during the sleep period. This results in a sleep debt at the end of the sleep period that accumulates over days. However, since the rate of sleep accumulation increases with sleep debt, eventually, the rate of sleep accumulation increases such that four hours of sleep makes up for twenty hours awake. At this point, the reservoir 70 reaches an equilibrium state and no further debt is accumulated, although the initial deficit remains as long as the person remains on this schedule. The result of this process is shown in FIG. 10, in which a schedule of one day with 8 hours of sleep followed by six days of 4 hours of sleep per day is illustrated, with each sleep period starting at midnight. By the sixth day of the restricted sleep schedule, cognitive performance oscillates about a stable level well below the baseline level achieved with 8 hours of sleep. Minimum effectiveness is about 60% on the seventh day.

FIG. 10 also illustrates the operation of sleep inertia SI during the first two hours following awakening according to the simulation. With only four hours sleep per night, the average intensity of sleep is high compared to a normal 8 hours sleep period. As a consequence, sleep inertia, which is driven by sleep intensity at time of awakening, is relatively high. This is evident as the initial "notch" in performance immediately after awakening in this seven-day record of performance.

Figure 11:
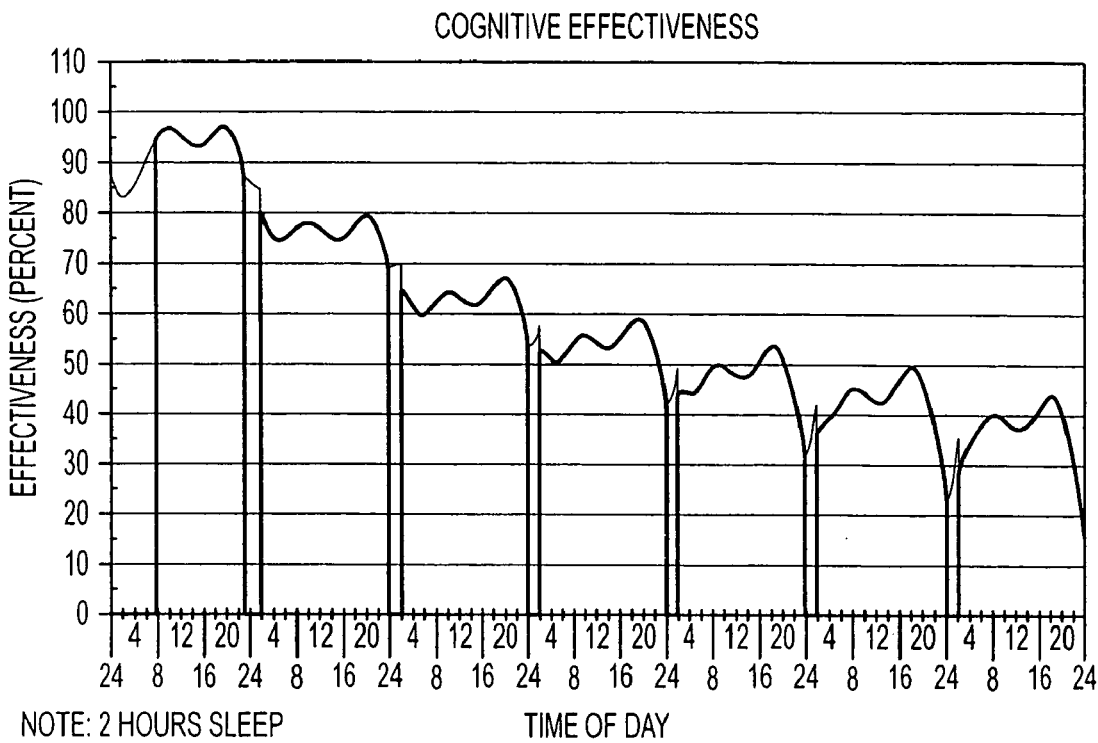
FIG. 11 is a graph illustrating an extended record of sleep and performance under a schedule of only 2 hours of sleep per day, according to one variation of the present invention (the heavy line is performance while awake)

Progressive sleep debt under extreme schedules can also be predicted using the method for evaluating the effectiveness according to the present invention. The sleep homeostat is not infinitely elastic; there is a limit to the rate of sleep accumulation (sleep intensity). Any schedule that provides less than 3 hours of sleep per day (for the average person) will not reach an equilibrium state and performance capacity will gradually deplete to zero, although the rate of depletion slows over the first week of restriction as sleep intensity rises to its maximum level. FIG. 11 is a graph illustrating a simulation of an extended record of sleep and performance under a schedule of only 2 hours of sleep per day. Under such a schedule, minimum performance declines to about 17% at the end of the seventh day.

Figure 12:
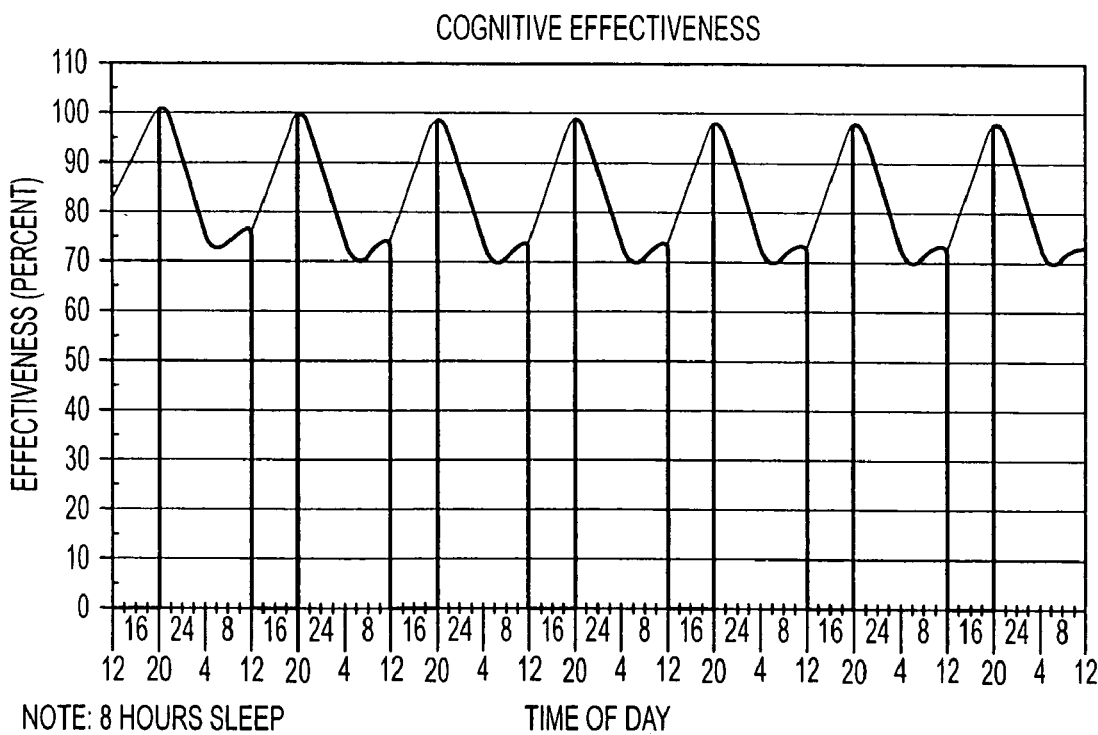
FIG. 12 is a graph illustrating the predicted performance of an individual given eight hours of sleep per day, starting at 1200 hours (noon) each day, according to one variation of the present invention and with phase adjustment deactivated for illustration (the heavy line is performance while awake)

The performance effects of sleep timing can be predicted. The method for evaluating the effectiveness of the present invention is sensitive to the time of day of the sleep period. FIG. 12 illustrates the predicted performance of an individual given eight hours of sleep per day, starting at 1200 hours (noon) each day, 12 hours out of phase from that shown in FIG. 4. Although performance reaches a peak of 100% at the start of each awake period (2000 hours), predicted performance then rapidly declines during the late night and early morning hours to a strong dip at about 0500 hours. Minimum predicted performance under this schedule is predicted to be as low as 69% compared to minimum performance under a normal sleep schedule of 86%. Note that for this chart, the phase correction algorithm was disabled so that the full effects of out of phase sleep could be visualized.

This alteration in pattern results from two factors. First, sleep intensity is initially less for sleep periods starting at noon. This results in accumulation of a small debt that is quickly offset by the homeostatic sleep mechanism. The second, more persistent pattern is the combined effect of the circadian oscillation of performance that reaches its minimum in the early morning hours and the sixteen hours of accumulated sleep debt at the end of the awake period that predicts a strong dip in effectiveness toward the end of the awake period. This pattern has strong implications for performance under shift schedules that require daytime sleep. It is well documented that most mistakes on the night shift occur during the early morning hours and this outcome is predicted by the present method for evaluating effectiveness.

The system and method for evaluating effectiveness of the present invention can predict changes in cognitive capacity as measured by standard laboratory tests of cognitive performance. It is assumed that these tests measure changes in the fundamental capacity to perform a variety of tasks that rely, more or less, on the cognitive skills of discrimination, reaction time, mental processing, reasoning, and language comprehension and production. However, specific tasks, such as specific military tasks vary in their reliance on these skills, and deficits in cognitive capacity may not produce identical reductions in the capacity to perform all military tasks. It is reasonable to assume, however, that the changes in military task performance would correlate with changes in the underlying cognitive capacity. In other words, if one were to plot changes in military task performance as a function of measured changes in cognitive capacity, there would be a monotonic relationship between the two variables. Therefore, if these two sets of data were available from a test population subjected to sleep deprivation, linear (or non-linear) regression techniques could be applied to derive a transform function; this transform translates predicted cognitive changes into changes in military task performance. Based on this reasoning, the method for evaluating the effectiveness, discussed previously as the cognitive effectiveness 56, can be extended to predict variations in any task or component of a task (given appropriate test data) using the generalized task effectiveness (TE) expression as follows:

$$TE = A(R_t/R_c) + B + C1[\cos(2\Pi(T-P)/24) + C2(\cos(4\Pi(T-P-p')/24))] + I,$$

where A=linear component slope, B=linear component intercept, C1=Circadian weighting factor, C2=12 hr weighting factor, and P=acrophase of the task.

Figure 13A:
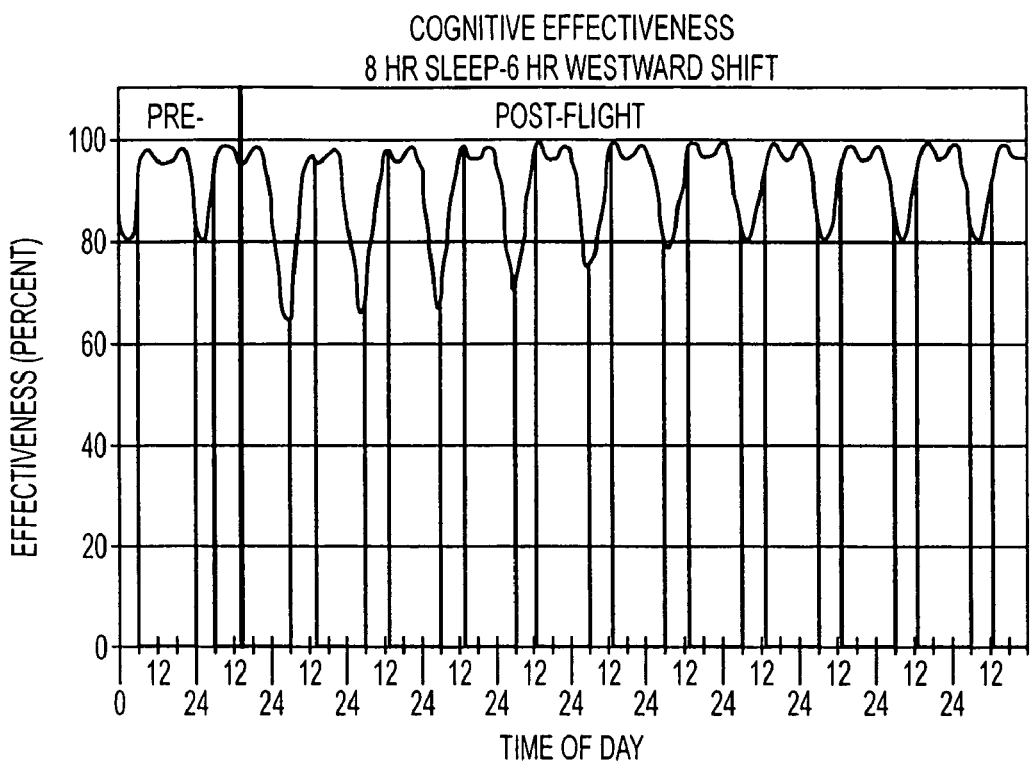
FIG. 13 is a is a graph illustrating the adjustment of performance to two flights, an east-bound flight across six time zones and a west bound flight across 6 time zones, according to one variation of the present invention.
Figure 13B:
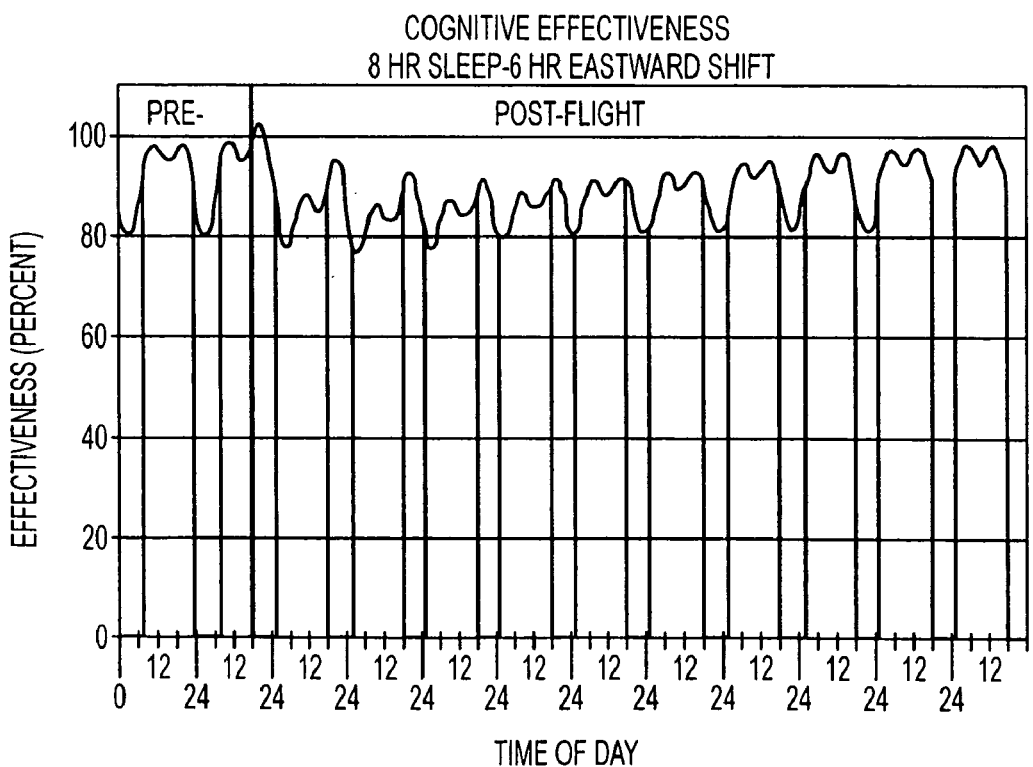

With regard to "Jet Lag" the system and method for evaluating effectiveness can predict the adaptation of performance to changes in time zones that might accompany trans-meridian flights or that might occur if the subject shifts to a regular schedule of nighttime work. FIG. 13 is a graph illustrating the adjustment of performance to two flights, an east-bound flight across six time zones and a west bound flight across 6 time zones.

Predicted performance while awake is more disrupted for a longer period of time by the east bound flight compared to the west bound flight, a commonly reported difference in "jet lag" for east and west plane travel. These effects on performance are a logical and inherent outcome of the interplay of the various processes in the model and do not require a special "jet lag" algorithm. The method for evaluating the effectiveness of the present invention has logic to detect such a change in work pattern and to readjust the phase of the circadian rhythm to the new work pattern indicative of the shift in time zone. The performance prediction was a natural outgrowth of the shifting circadian phase.

When a person moves to another time zone or alters work patterns so that sleep and work occur at different times of day, the internal circadian oscillator that controls body temperature and alertness shifts to this new schedule. During the period of adjustment, a person experiences performance degradation, disrupted mood, and feelings of dysphoria, called circadian desynchronization or "jet lag".

Figure 15:
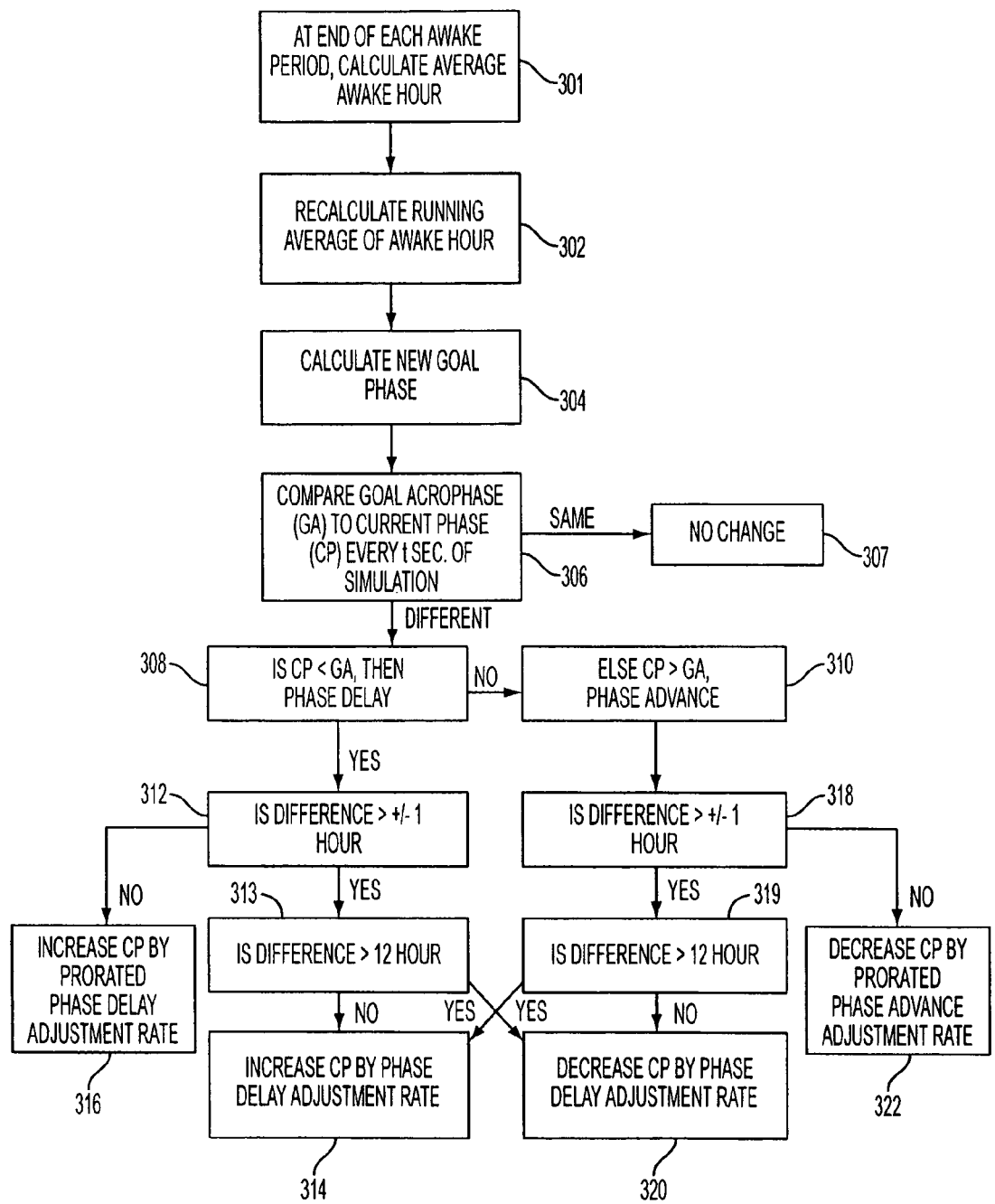
FIG. 15 is a flow chart of a method for adjusting the phase of a person's circadian oscillator based on the timing of major awake periods, according to the present invention.

The method for evaluating the effectiveness of the present invention can simulate this process and automatically adjust the phase of the circadian rhythm to coincide with the activity pattern of the person, at step 212, FIG. 15. Such simulation is important in order to accurately predict the effects of moving to a new time zone or changing to a new and regular work pattern, such as changing from the day shift to the night shift. The method for evaluating the effectiveness detects the average time of the period of wakefulness, and gradually adjusts the time of the peak in the circadian rhythm in relation to the new average awake hour.

The details of the phase adjusting process 212 are charted in FIG. 15. The peak of the circadian rhythm has a reliable relationship to the timing of the period of wakefulness. When a person moves to a new work schedule or a new time zone, the change in average awake time 301 and 302 (relative to a reference time zone) is detected and a new "goal phase" is computed, 304. For example, when moving from the central US time zone to Germany, the awake time of the subject advances six hours. Instead of waking at, say, 0600 Central Time, the subject awakens at 0000 Central Time, which is 0600 German time. This causes a shift of 6 hours in the "goal phase" of the person.

However, the human physiological system does not adapt immediately to such a shift. In general, the speed of adjustment depends on whether the change requires a phase advance or a phase delay. A phase advance (eastward time change) takes about 1.5 days per hour of shift. One embodiment of the present invention adjusts to the new "goal phase" gradually over the course of about nine days for a six hour advance, steps 310, 318, 319, 320, 322. During that time, the performance of the subject will show degradation due to the desynchronization of the internal circadian rhythm from the new rhythm of work and sleep. Likewise, westerly travel causes a phase delay in the circadian rhythm and research shows that phase delays take less time for adjustment, about one day per hour of shift, or six days for a six hour time change, steps 308, 312, 313, 314, 316.

The details of the mathematics of this process are as follows:

A basic premise of the method is that periods of wakefulness provide a strong entrainment stimulus that serves as the basis of phase adjustments to the circadian rhythm. As a result, the time of the period of wakefulness is the primary factor in determining the phase of the circadian rhythm. At the end of each period of wakefulness the model computes a new "running average awake hour," which is the average of that period of wakefulness averaged with the average awake hour of the prior two periods of wakefulness, 301 and 302. Although the wakefulness period is used, this is not to imply that there are not other entrainment stimuli for adjusting the phase of the circadian rhythm such as bright light, activity, etc. Also, brief awakenings during the night lasting only a few minutes (for example, less than 60 minutes) are disregarded.

Based on the running average awake hour, the system computes a new "goal phase" as the running average awake hour plus, for example, 3 hours, 304. For an awake time from 08 to 24 (average of 16), that gives an acrophase of 19, which is a current default.

The system adjusts the current acrophase each minute by comparing the goal to the prior current acrophase. If the difference is greater than 1 hr (+/−1), it starts adjusting the acrophase by ¹⁄₁₄₄₀ of an hour for each minute of delay (314) or ¹⁄₂₁₆₀ of an hour for each minute of advance (320). The system adds or subtracts, depending on whether the difference is + or −. If the difference is less than an hour, it adjusts by that difference times ¹⁄₁₄₄₀ or ¹⁄₂₁₆₀ each minute, 316 or 322. It checks to see if the difference is greater than 12 hours, in which case it is shorter to go in the opposite direction. In that case, the current acrophase is adjusted by + or −24, and the direction of change is reversed. This method ensures that the current acrophase is adjusted along the shortest path to the goal phase.

The result is a model that adjusts about one hour a day per hour of phase delay and one hour per 1.5 days for each hour of phase advance. It adjusts smoothly and continuously so that it will also deal with rotating shifts, in which case the goal acrophase shifts back and fourth and the adjusting acrophase keeps trying to find the goal at the prescribed rate, but never gets there unless the schedule stabilizes. Other factors, such as bright light or dietary factors, may be incorporated in the model as factors that change the rate of adjustment of the physiological rhythm to the predominant schedule represented by the goal acrophase. As indicated below, the rates of phase change for advances and delay are reduced for shift-work changes in sleep pattern, indicated by sleep during daylight hours.

As used herein a number of terms have specific meanings. In particular, the term AVERAGE AWAKE HOUR 301 refers to the average awake hour of any awake period based on the average clock time of the awake period, provided the awake period is one hour or longer. Therefore, a period from 0800 hrs to midnight would have an average clock time of 1600 hrs (the middle of the period). The RUNNING AVERAGE AWAKE HOUR 302 is the average of the average awake hours for the last three periods of wakefulness. The three periods are weighted so that the period just ended has greater weight than either of the two previous periods and the previous period greater weight than the period prior to it, for example (1x+0.67y+0.33z)/2.

The term GOAL PHASE is simply the RUNNING AVERAGE AWAKE HOUR plus a constant displacement, which has a default value of +3 hours, 304. This gives a 'standard' acrophase of 1900 hrs for a 16 hour period of wakefulness from 0800 hrs to midnight.

The term ADJUSTING ACROPHASE (steps 308 to 322) refers to a calculation that adjusts at a rate of one hour per day for phase delays or ⅔ hour per day for phase advance until it is within 1 hour of the goal, and then gradually approaches it from that point to zero deviation. The ADJUSTING ACROPHASE is needed to account for the fact that the biological phase cannot shift in one big jump to the GOAL PHASE.

Running Average Awake Hour 302

The following is a breakdown of the determination of the RUNNING AVERAGE AWAKE HOUR according to the present invention.

Given:

CA=Cumulative minutes awake at end of awake period.

TAE=Time of awake period end $AH_n$=AVERAGE AWAKE HOUR for awake period n (301).

AV=RUNNING AVERAGE AWAKE minutes (302).

At the end of each awake period calculate new AV, where n=0 is just ended awake period, n=1 is previous awake period, and n=2 is awake period prior to that.

Equation 1a, $AH_n$, AVERAGE AWAKE HOUR for awake period n:

$$AH_n = IF\ (TAE-(CA/60)<0),\ \text{then}\ (TAE+24+(TAE+24-(CA/60)))/2),$$

$$\text{else}\ (TAE+(TAE-(CA/60))/2)).$$

Equation 1b, RA, RUNNING AVERAGE AWAKE HOUR:

$$AV=(0.33*AH_2+0.67*AH_1+w*AH_0)/(w+1),$$

where $w=CA_0/120$, and minimum value=1.

Explanation:

(TAE−(CA/60)) is the time of the start of the awake period in hours, and (TAE+(TAE−(CA/60)))/2 calculates the AVERAGE AWAKE HOUR 301 as the simple average of the beginning time and ending time. For unusually long awake periods greater than 24 hours, the average hour of the last portion of the awake period less than 24 hrs is averaged with a time 12 hrs after the start of the awake period for each proceeding 24 hour period awake.

AV 302 is calculated as the weighted average of the last three awake periods, such that the just ended period has weight equal to half the duration in hours of the just ended awake period, the two prior periods have a combined weight of one, and the prior period has a weight twice that of the period prior to it.

Goal Phase 304

Given: RA=A parameter that sets the RELATIVE ACROPHASE based on the AVERAGE AWAKE HOUR. For example an RA=3 gives an acrophase of 19 by adding it to the AVERAGE AWAKE HOUR of 16 for an awake period from 0800 to 2400. This is a parameter.

GA=GOAL PHASE

Then: at the end of each awake period calculate a new GOAL PHASE:

$$GA=AV+RA \qquad \text{Equation 2:}$$

Explanation:

The acrophase of the arousal/temperature rhythm is set relative to the AVERAGE AWAKE HOUR. That is the essence of using the awake time as the entrainment stimulus for the phase shifting model. As average awake hour shifts with a new schedule or time zone, then the goal phase adjusts also. The actual phase of the temperature rhythm does not adjust immediately to this new goal phase, but gradually moves toward it according to the adjustment algorithm discussed next.

Adjusting Acrophase—Phase Correction Algorithm (308 to 322)

Given: CP=Current Acrophase, $PC_a$=amount of Phase Change in minutes for each hour of advance, default value is 2160 minutes per hour of advance (eastward flight direction), $PC_d$=amount of Phase Change in minutes for each hour of delay, default value is 1440 minutes per hour of delay (westward flight direction).

Then: at each minute of schedule, adjust the current acrophase according to the following algorithm:

Equation 3:

If GA=CP, then no change. 307
If CP<GA: Phase Delay 308
Then, If GA−CP>1, 314
If GA−CP>12, then New CP=Old CP+24−1/$PC_a$
Else, New CP=Old CP+1/$PC_d$
Else, New CP=Old CP+(GA−CP)*1/$PC_d$, 316
If CP>=GA: Phase Advance, 310
Then, CP−GA>1, 320
If CP−GA>12, then New CP=Old CP−24+1/$PC_d$
Else, New CP=Old CP−1/$PC_a$
Else, New CP=Old CP+(GA−CP)*1/$PC_a$, 322

Explanation:

The initial IF statements 308 and 310 check to see which is greater, GOAL PHASE or CURRENT ACROPHASE. That determines which way to move the CURRENT ACROPHASE, i.e. phase delay or advance.

The next level of IF statements determines if the difference is greater than one hour, the basic unit of change, 312 and 318. If it is greater than one, then the acrophase is moved by +/−1/PC hours; if it is less than one, the acrophase is moved by the difference times 1/PC. This gives an average rate of change of about 1/PC and then approaches the Goal value gradually.

The next level of IF statements determines if the difference is greater than 12 hours, 313 and 319. If it is greater than 12 hours, then 24 is subtracted or added as appropriate and moved in the opposite direction. Otherwise, CP is adjusted by the delay or advance rate as appropriate, 314 or 320. This determines the shortest distance and adjusts the direction of change accordingly.

Note that the method of change when the difference is less than 1 hour is the same expression, regardless of which is greater, GA or CP. This is because the (GA−CP) term will have the appropriate sign to move in the correct direction.

The above algorithm can be adjusted to account for the effects of light and other shift work factors on phase adjustment. The adjustment logic may use light information to determine whether the individual has undergone a transmeridian shift (i.e., changes time zones) or a phase shift in the same location (i.e., is performing shift work). The algorithm may use the standard rates of circadian phase change for the transmeridian shifts and slower rates for shift work based on known shift work literature. The algorithm does not attempt to precisely model the laboratory studies of light effects on the grounds that in the real working world the rates of adjustment to shift work are the combined effects of light on physiology and the effects of activity, as well as social and environmental cues. Hence, the model may use the reported rates of change in body temperature in shift-workers as a summary of the effects of all those inhibiting factors.

The rate of phase change for an advance or a delay is adjusted for the percent of the sleep period that coincides with daylight, indicative of shift work. This percentage is corrected for the amount of darkness available based on latitude and season of the year. The inventive method and system may use the location information entered at the time the schedule is created, and any WAYPOINTS that change the subject's location, combined with the date and time of day, to determine the amount of available solar light at that location at that time and season. These calculations are based on standard astrophysical calculations available in the public domain. The gray bars along the x-axis of the FAST graphical screen (described below, e.g., bar 505 in FIG. 19) indicate the calculated periods of darkness.

For low percentages of daylight during sleep (indicative of normal night-time sleep), rates of adjustment are as indicated above for adjustments to transmeridian relocation. For larger percentages of daylight during sleep (indicative of shift work sleep during the day), the rate of adjustment is progressively reduced to reflect the slower rates of adjustment indicative of shift work. The shift work rate of adjustment may be calculated as follows:

Percent Sleep Light=(Hrs Light Asleep/Total Hrs Asleep)−(Minimum Hrs Light/Total Hrs Asleep)

Minimum Hrs Light=Total Hrs Asleep−Total Hrs Dark in 24 hrs, if <Total Hrs Asleep, else=0

The model may define four percentage ranges for determining rate of shift, as shown in the table below:

| Percent Sleep Light | Phase Change Factor | Resulting Rates of change (min. per hour of phase change) | |
|---|---|---|---|
| | | Delay ($PC_d$) | Advance ($PC_a$) |
| 0%–16.7% | 1.0 | 1440 | 2160 |
| 16.7%–33.3% | 1.5 | 2160 | 3240 |
| 33.3%–50.0% | 2.0 | 2880 | 4320 |
| >50.0% | 2.67 | 3845 | 5767 |

Figure 16:
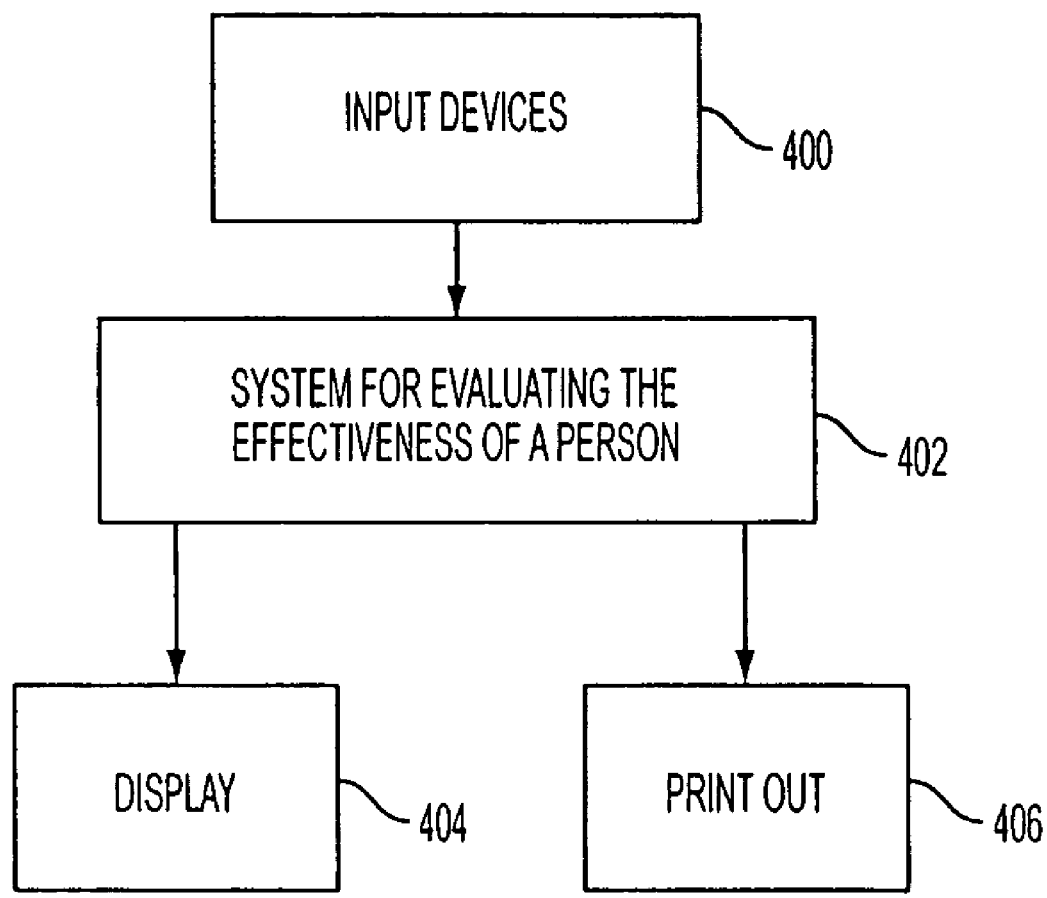
FIG. 16 is a block diagram of a system of evaluating the effectiveness of a person according to the present invention.

FIG. 16 illustrates a block diagram of a system for predicting task effectiveness according to the present invention. Data is entered using input devices 400. These input devices 400 may include a keyboard and mouse, a data storage medium from which the data maybe extracted, and sensors that provide time and sleep/wakefulness data.

The system 402 may include a microprocessor that uses the data entered through the input devices 400 to provide results either to the display 404 or the print out 406. These results may be similar to the graphs shown in FIGS. 4, 10, 11, and 12. The system can utilize actual data for a particular person to provide task effectiveness data that is particular to that person, or can be used to predict task effectiveness for the general population or a sub-group of the population.

For example, FIGS. 10 and 11 are graphs illustrating sleep and predictions of cognitive effectiveness with four and two hours of sleep per night, respectively, while FIG. 12 shows a graph of the predicted performance of an individual given eight hours of sleep per day, starting at 1200 hours (noon) each day. These figures illustrate the predictive capacity of the system of the present invention. The raw sleep/wake data is entered, most likely, through a keyboard so that the system can produce the general predictive results, such as shown in FIGS. 10–12.

For a particular person, the actual sleep data may be entered for that person. The data may be manually entered into the system 402 via a keyboard and/or automatically through sensors that provide the sleep/wake data for that person. Similarly, the data concerning the cognitive skills required for a particular task may be entered using the keyboard or may be downloaded from a storage medium.

The details of the interface of the present invention, and how the interface utilizes the system and method described above, will now be described with reference to FIGS. 17–54.

Figure 17:
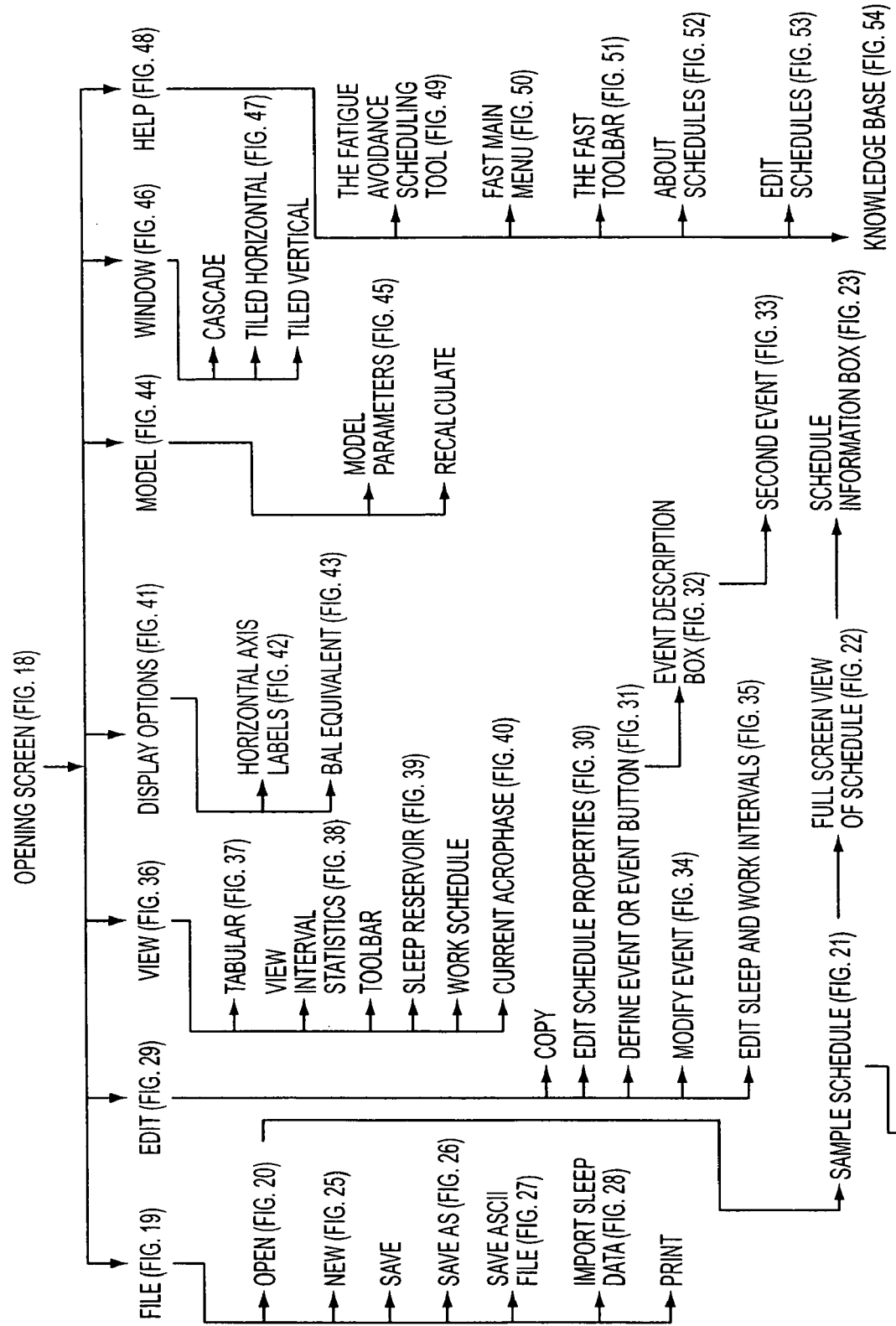
FIG. 17 is a flow chart showing the inter-relationship of the screens of the interface for the system for evaluating the effectiveness of a person to perform a task according to the present invention.
Figure 18:
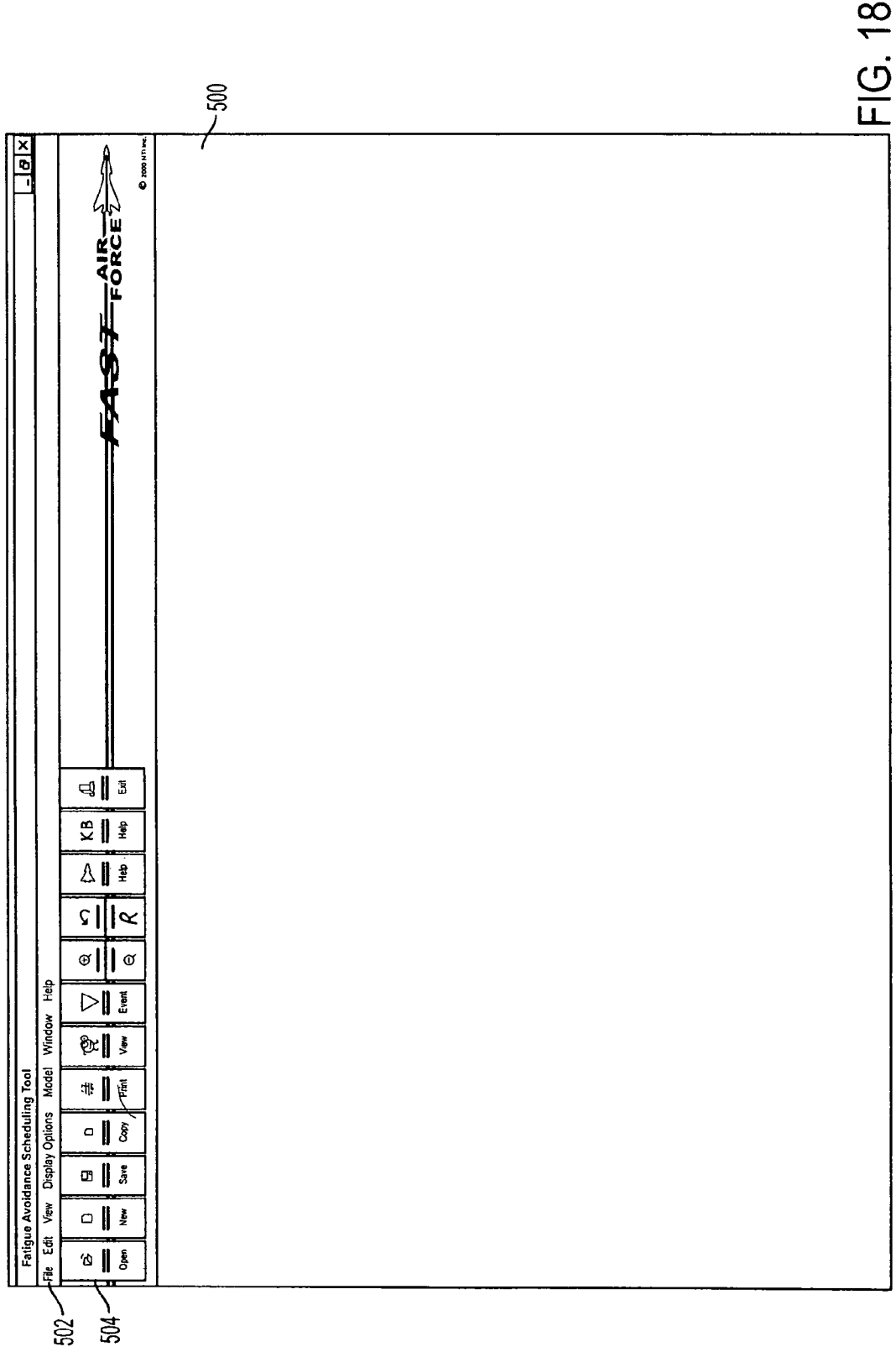
FIG. 18 is an opening screen of the interface for the system for evaluating the effectiveness of a person to perform a task according to the present invention.

FIG. 17 illustrates a flow chart showing the inter-relationship of the screens of the interface for the system for evaluating the effectiveness of a person to perform a task according to the present invention. The interface begins with the opening screen 500 shown in FIG. 18. The opening screen 500 includes a main toolbar 502, and a secondary toolbar 504.

The Main toolbar 502 may include FILE, EDIT, VIEW DISPLAY, OPTIONS, MODEL, WINDOW, and HELP options. The secondary toolbar 504 may include OPEN, NEW, SAVE, COPY, PRINT, VIEW, EVENT, ZOOM±, UNDO, RECALCULATE, HELP, and EXIT options. Not all of the options in the main toolbar 502 and secondary toolbar are immediately available from the opening screen 500.

Figure 19:
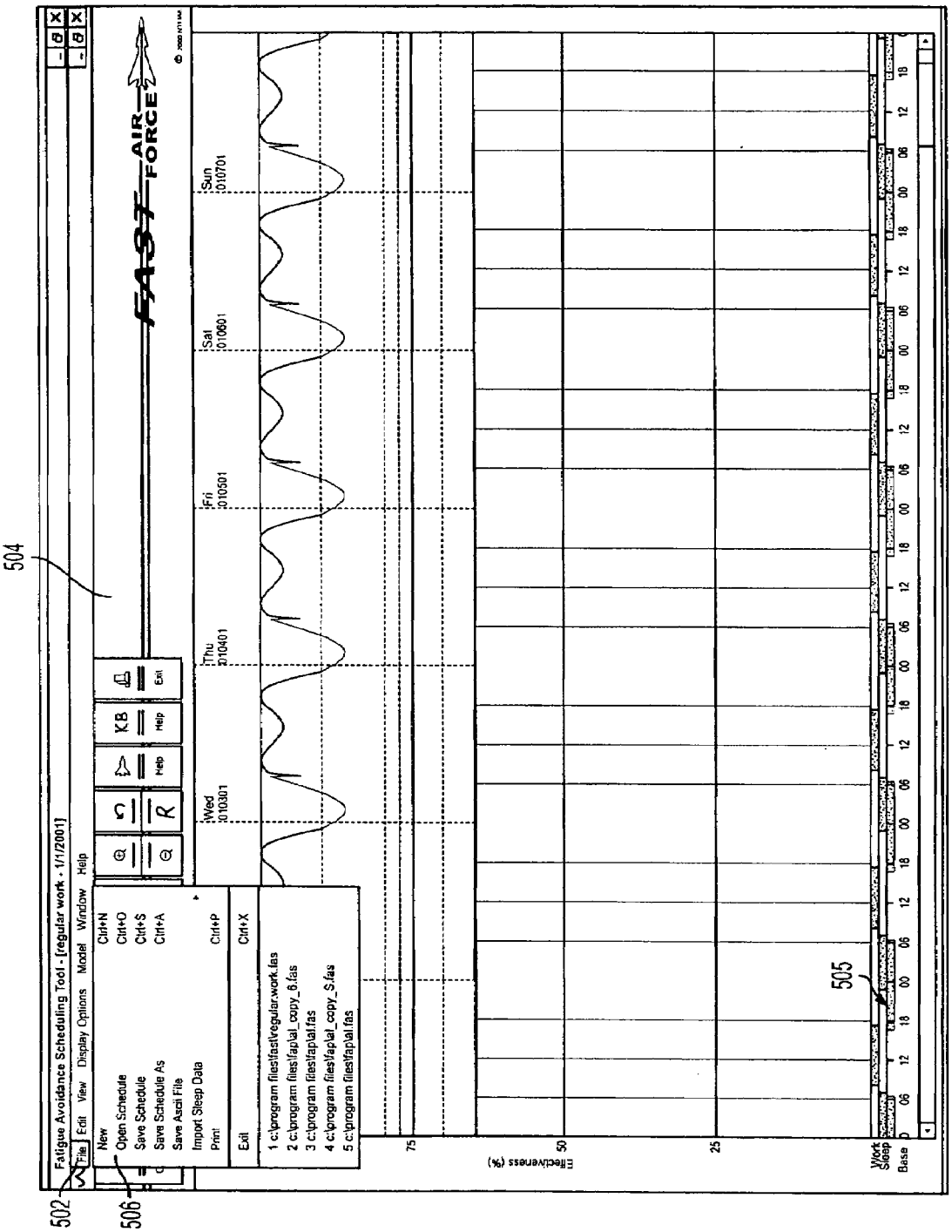
FIG. 19 is a file menu screen of the interface for the system for evaluating the effectiveness of a person to perform a task according to the present invention.

By selecting the FILE option from the main toolbar 502, the file menu screen 506, shown in FIG. 19, is displayed, and includes NEW, OPEN SCHEDULE, SAVE SCHEDULE, SAVE SCHEDULE AS, SAVE AS ASCII FILE, IMPORT SLEEP DATA, and PRINT options. Some of these options duplicate options in the secondary toolbar 504. A user may select interface elements on the display using any known input device, such as a computer keyboard, mouse, trackball, touchpad, and the like.

Figure 20:
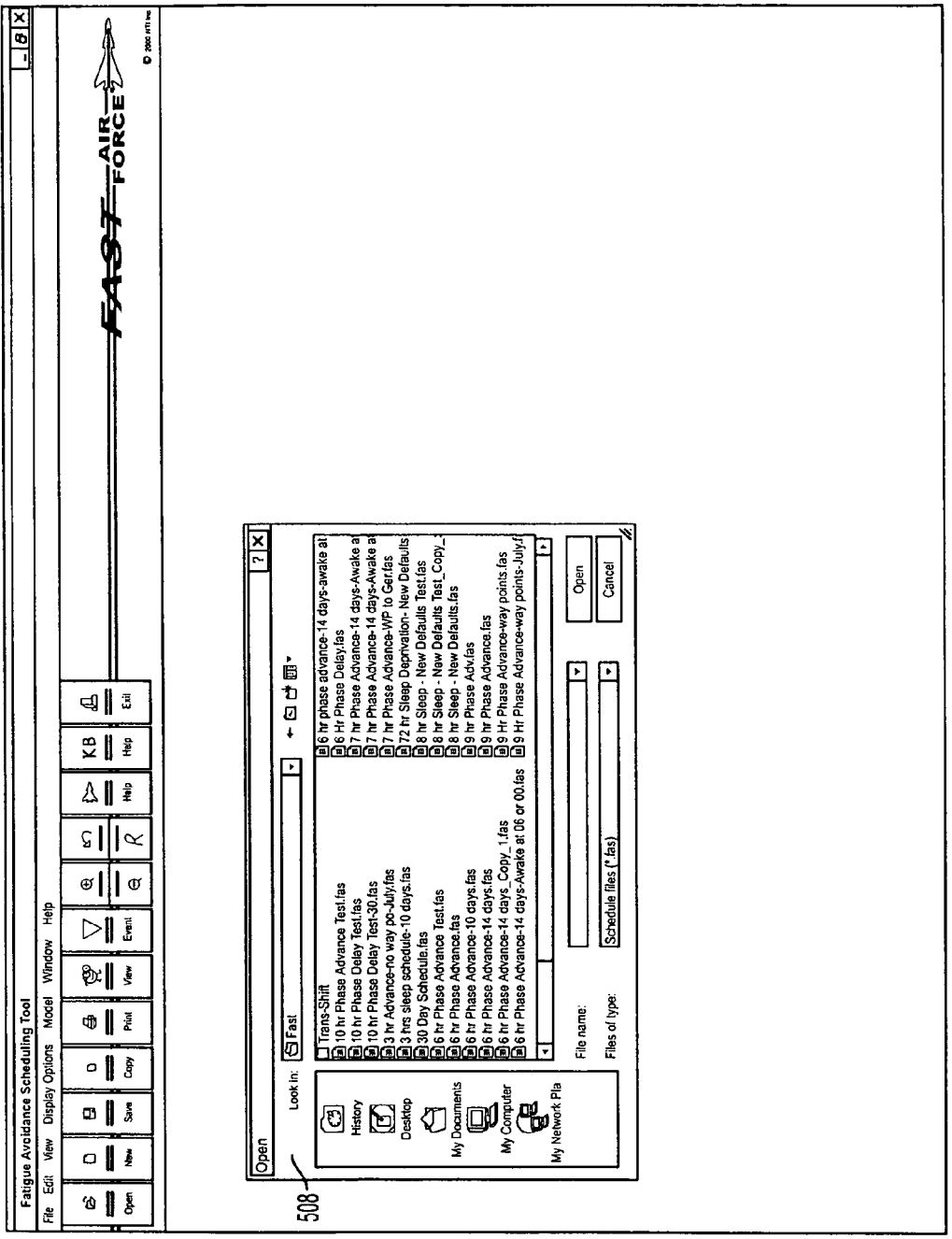
FIG. 20 is a file open screen of the interface for the system for evaluating the effectiveness of a person to perform a task according to the present invention.
Figure 21:
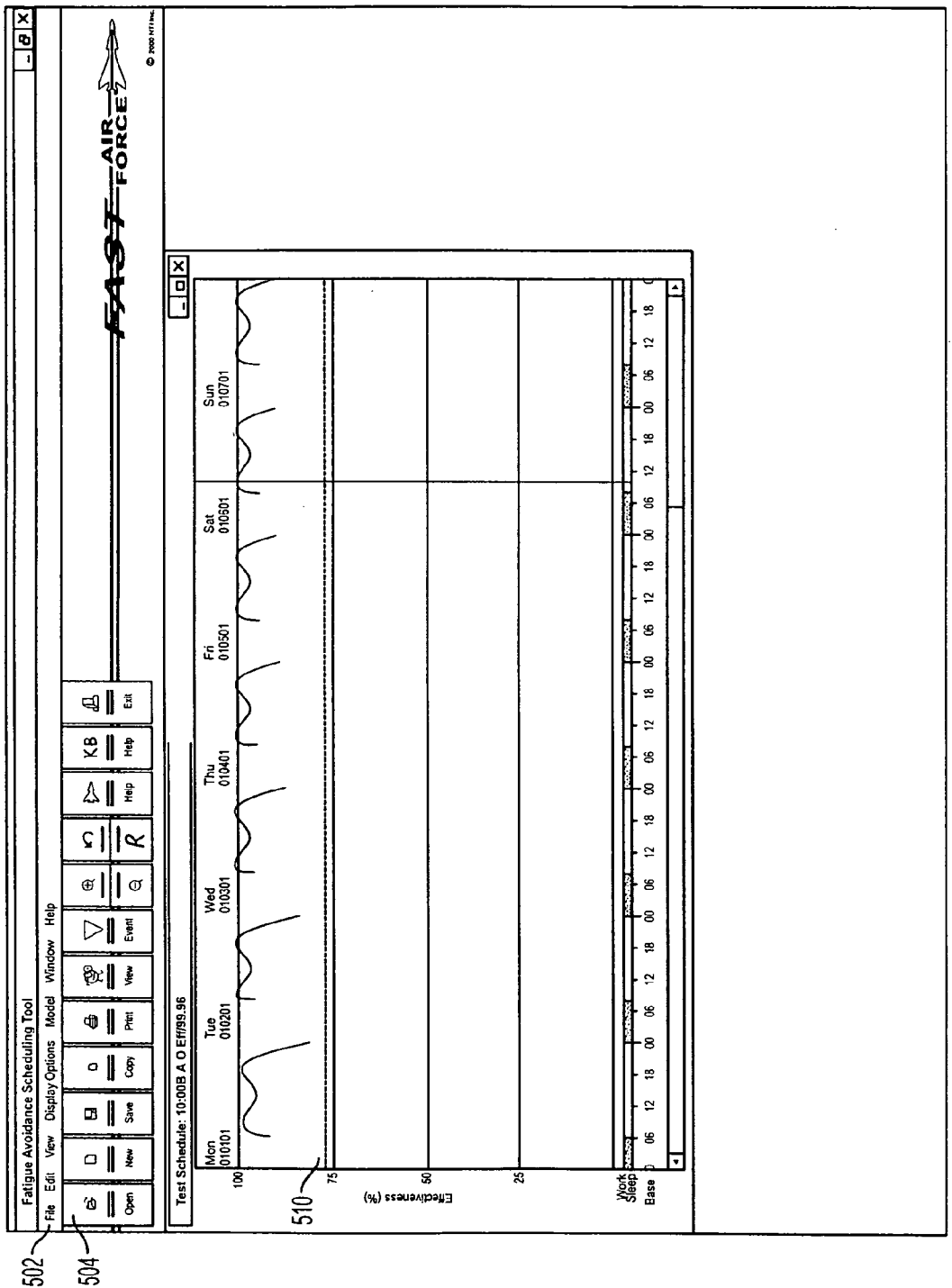
FIG. 21 is a sample schedule screen of the interface for the system for evaluating the effectiveness of a person to perform a task according to the present invention.
Figure 22:
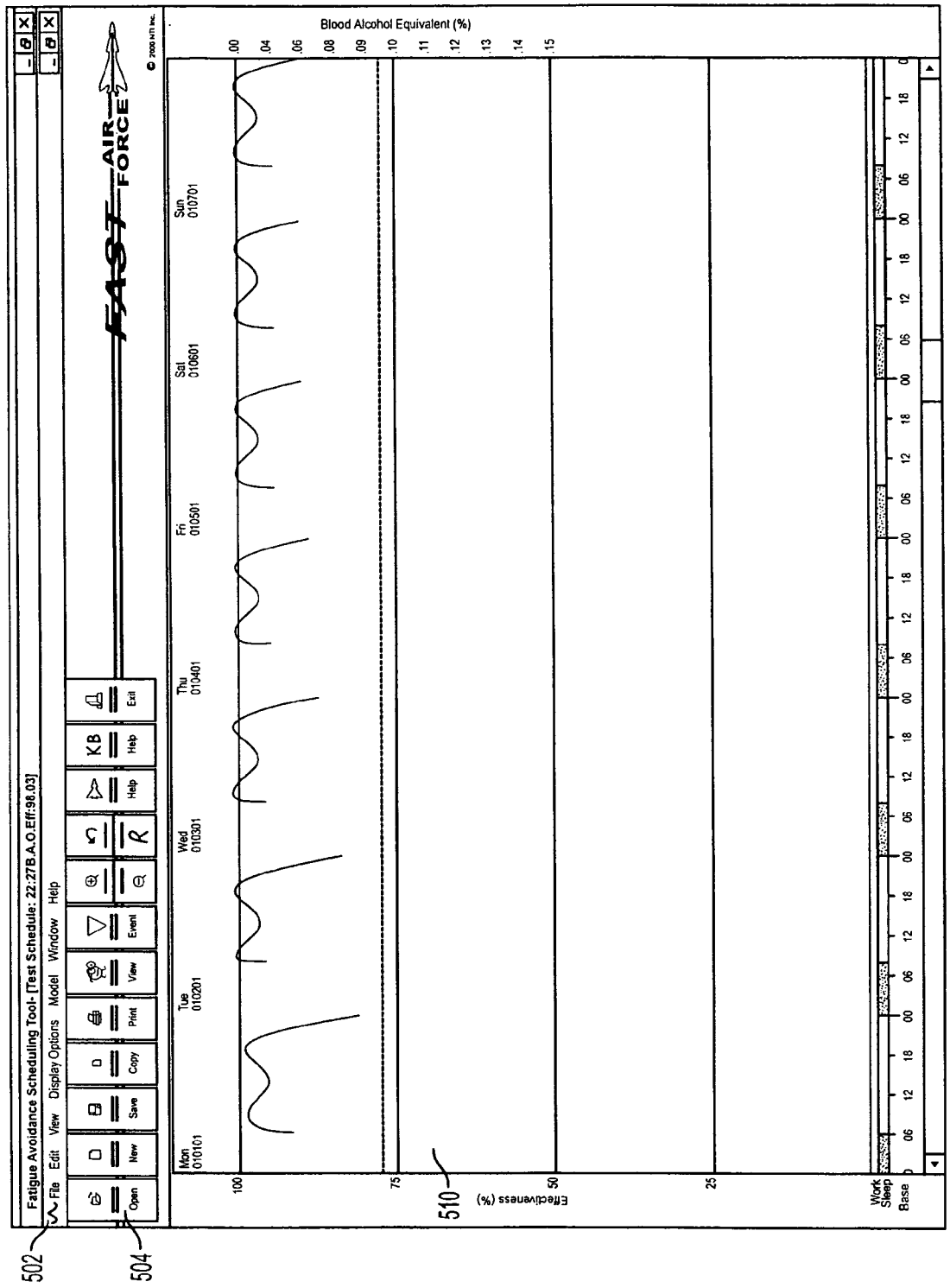
FIG. 22 is a full-screen view of a single schedule of the interface for the system for evaluating the effectiveness of a person to perform a task according to the present invention.

Selection of the OPEN option from file menu screen 506 or from secondary toolbar 504 causes the file open screen 508, shown in FIG. 20, to appear. Through the file open screen 508, a user can select previously saved files for new use or editing. As shown in FIG. 21, the user can view a schedule screen 510 corresponding to the selected file from the file open screen 508. While the schedule screen 510 illustrated in FIG. 21 is not a full screen, a user can select a full-screen view as shown in FIG. 22. Each schedule, by default, illustrates an individual's effectiveness based on his or her sleep patterns. Effectiveness is displayed as a percentage, using an individual's maximum effectiveness as the baseline from which the percentage is calculated. The schedule of FIG. 22 illustrates a typical circadian rhythm sleep schedule, calculated using the above-described model.

Figure 23:
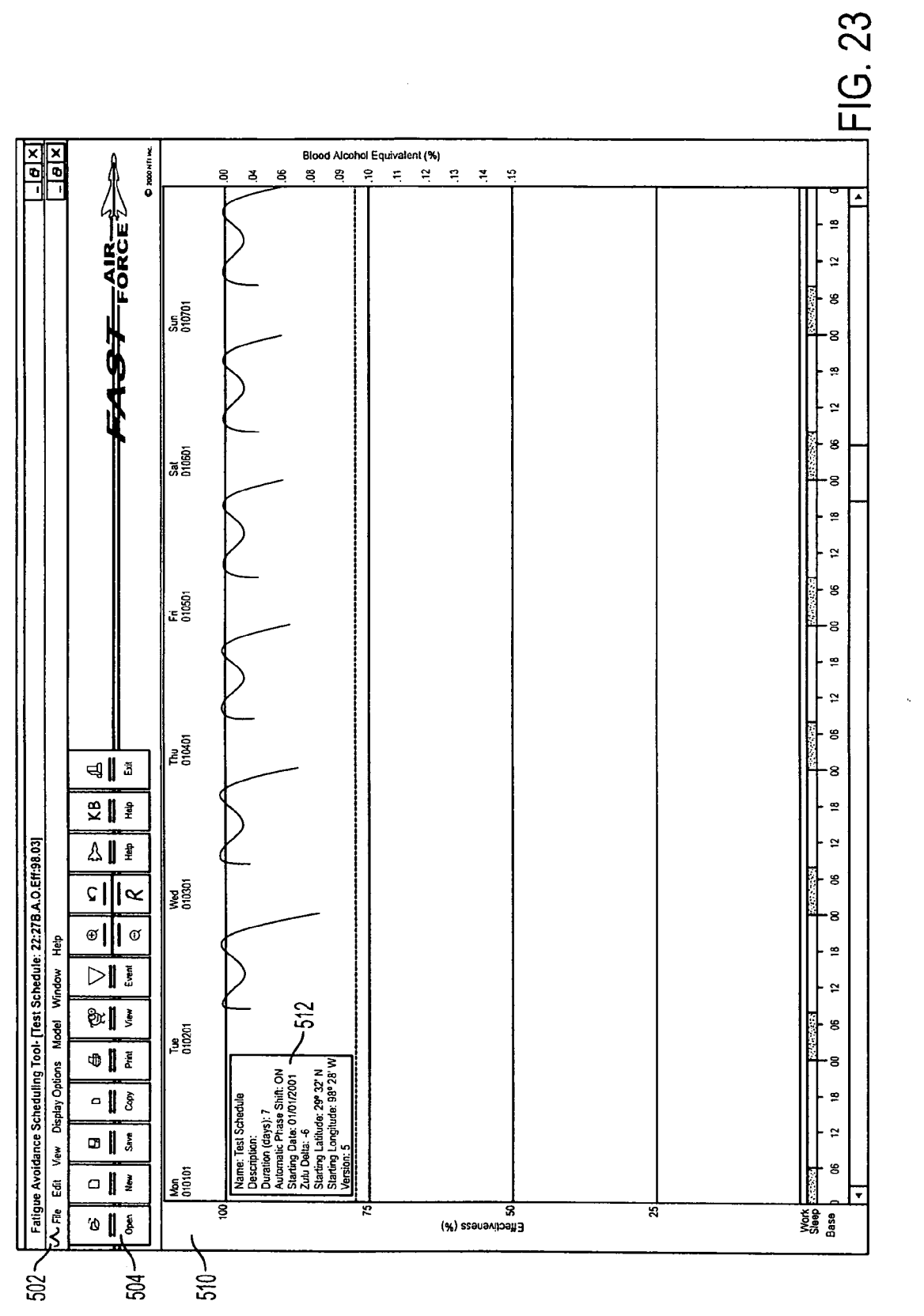

In addition, a displayed schedule may also have a schedule information box 512, illustrated in FIG. 23, superimposed on the schedule screen 510. While the schedule 510 comprises actual sleep/fatigue information as calculated above, the schedule information box 512 may contain metadata about the schedule, such as the name of the schedule, the schedule's duration, an indication whether automatic phase shift is on, the starting date, Zulu delta, starting latitude and longitude, and the version number. Zulu delta is the time expressed as the difference between the time at the present location from Zulu time.

Figure 24:
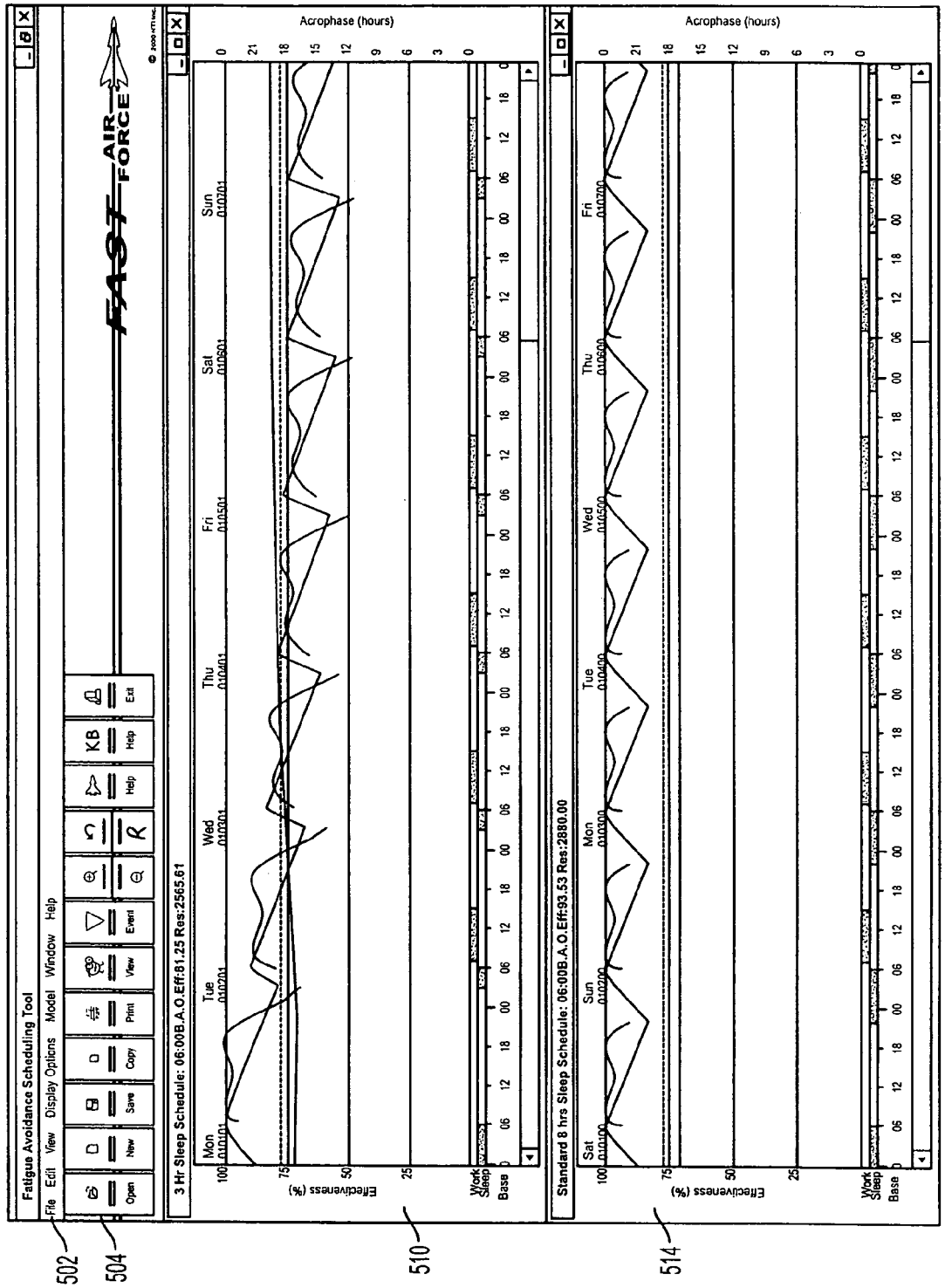
FIG. 24 is a screen showing two schedules tiled horizontally with reservoir and acrophase lines according to the interface for the system for evaluating the effectiveness of a person to perform a task of the present invention.

After selecting a first schedule screen 510, a user may select a second schedule screen 514, and choose to display them adjacent one another, such as tiled horizontally, as shown in FIG. 24. In this manner the user receives a simple side-by-side visual comparison of the two schedules. Obviously, other display arrangements may be used.

Figure 25:
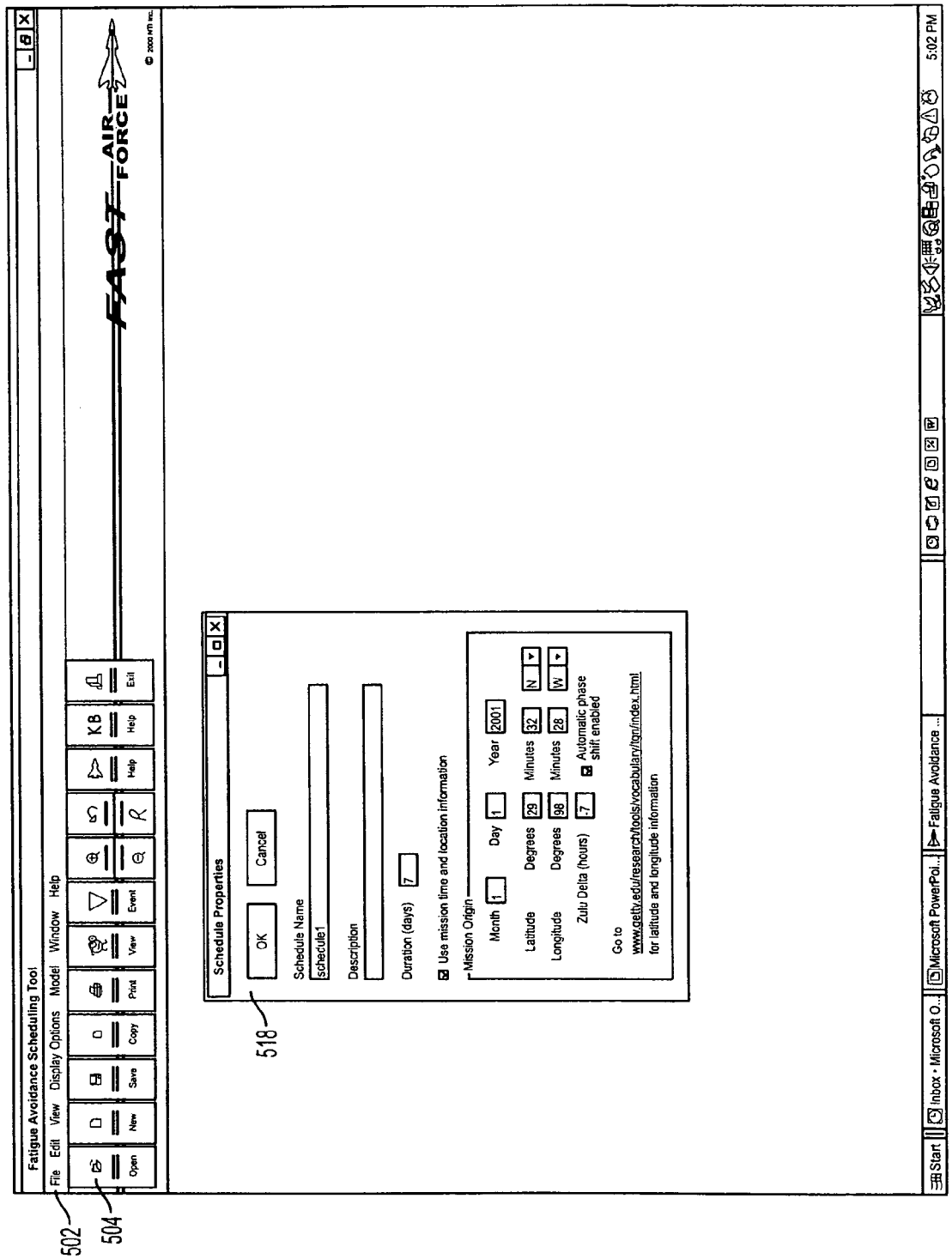
FIG. 25 is a schedule properties drop-down screen of the interface for the system for evaluating the effectiveness of a person to perform a task according to the present invention.

When a user selects the NEW option from either the drop-down screen 506 or from the secondary toolbar 504, the new schedule screen 518 is produced, as shown in FIG. 25. The user then enters the defining parameters of the schedule. These parameters correspond to the information contained in the schedule information box 512. A link to the Internet may be provided to assist in obtaining longitude and latitude data.

Figure 26:
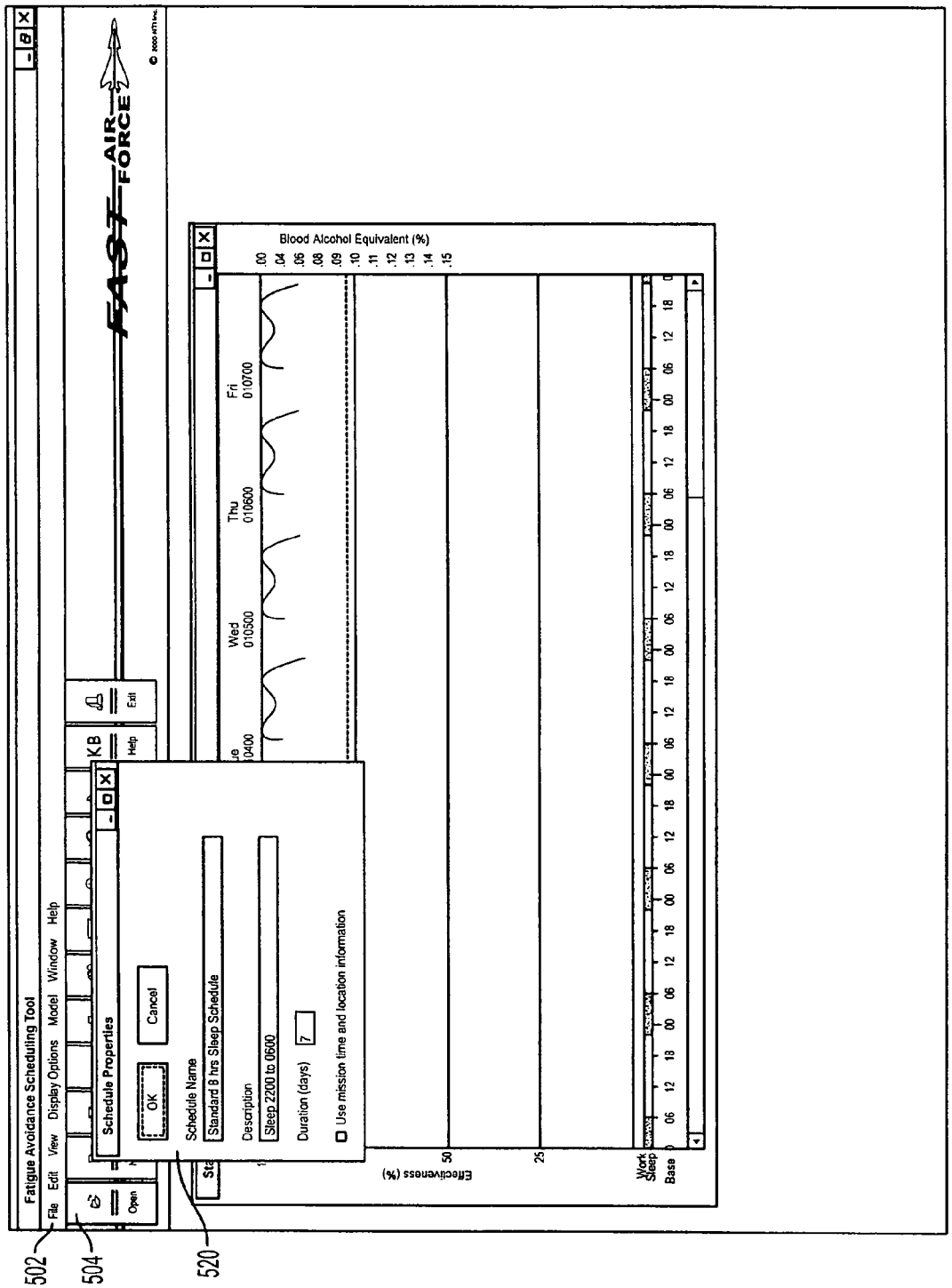
FIG. 26 is a schedule save screen for the interface of the system for evaluating the effectiveness of a person to perform a task according to the present invention.

After a schedule has been created, a user can save the schedule by selecting the SAVE SCHEDULE AS option from the drop down screen 506, shown in FIG. 19, and a schedule properties screen 520 is provided, as shown in FIG. 26. The user then may enter a name, description, and duration for the schedule.

Figure 27:
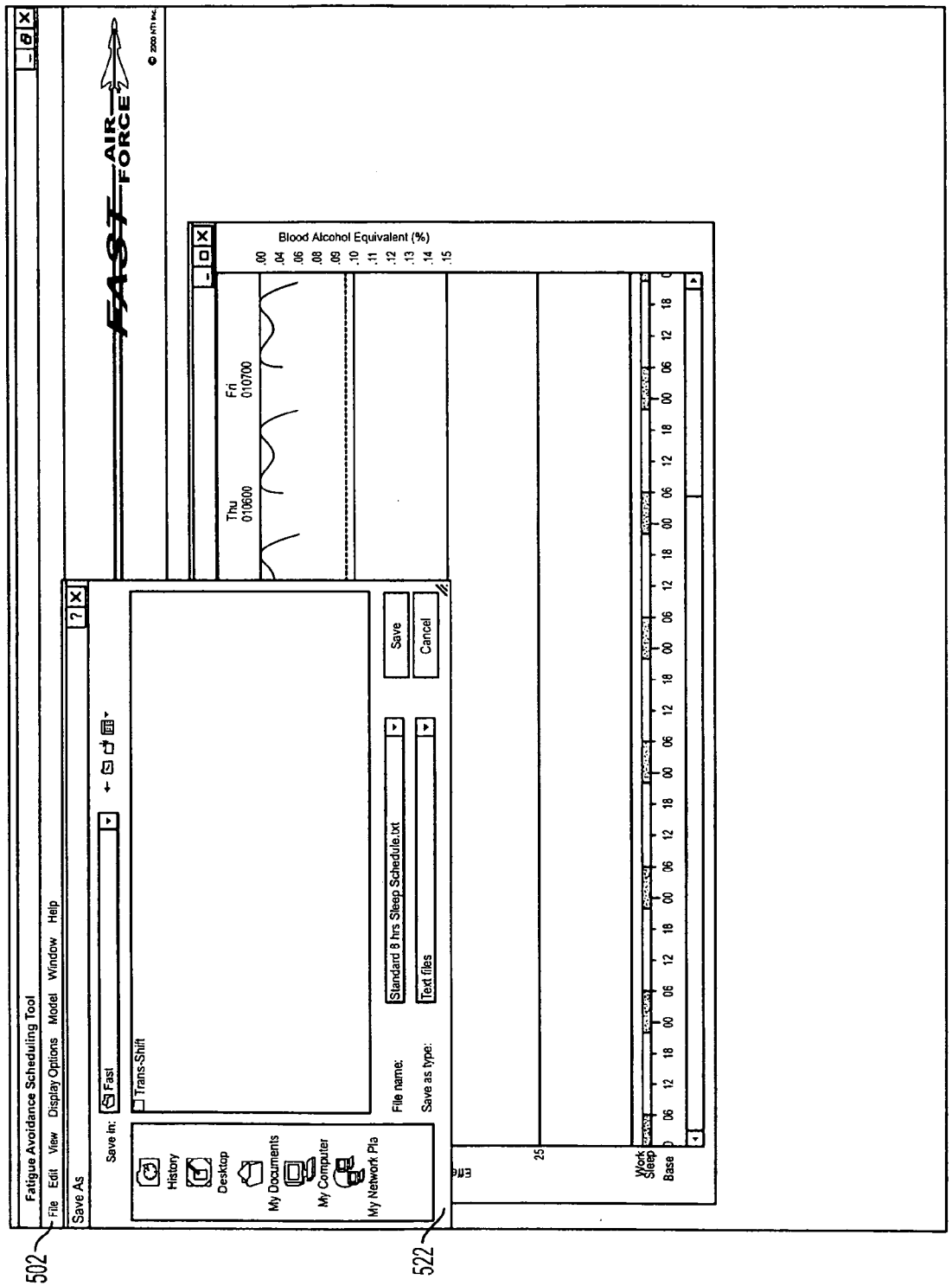
FIG. 27 is a screen for saving a schedule as an ASCII text file of the interface for the system for evaluating the effectiveness of a person to perform a task according to the present invention

Alternatively, the user can choose to save the schedule as an ASCII file. To do this the user selects the SAVE ASCII FILE option from the drop-down screen 506 shown in FIG. 19. By choosing the SAVE ASCII FILE option the save screen 522 shown in FIG. 27 is produced. The user then can choose where to save the file and what the file name should be.

Figure 28:
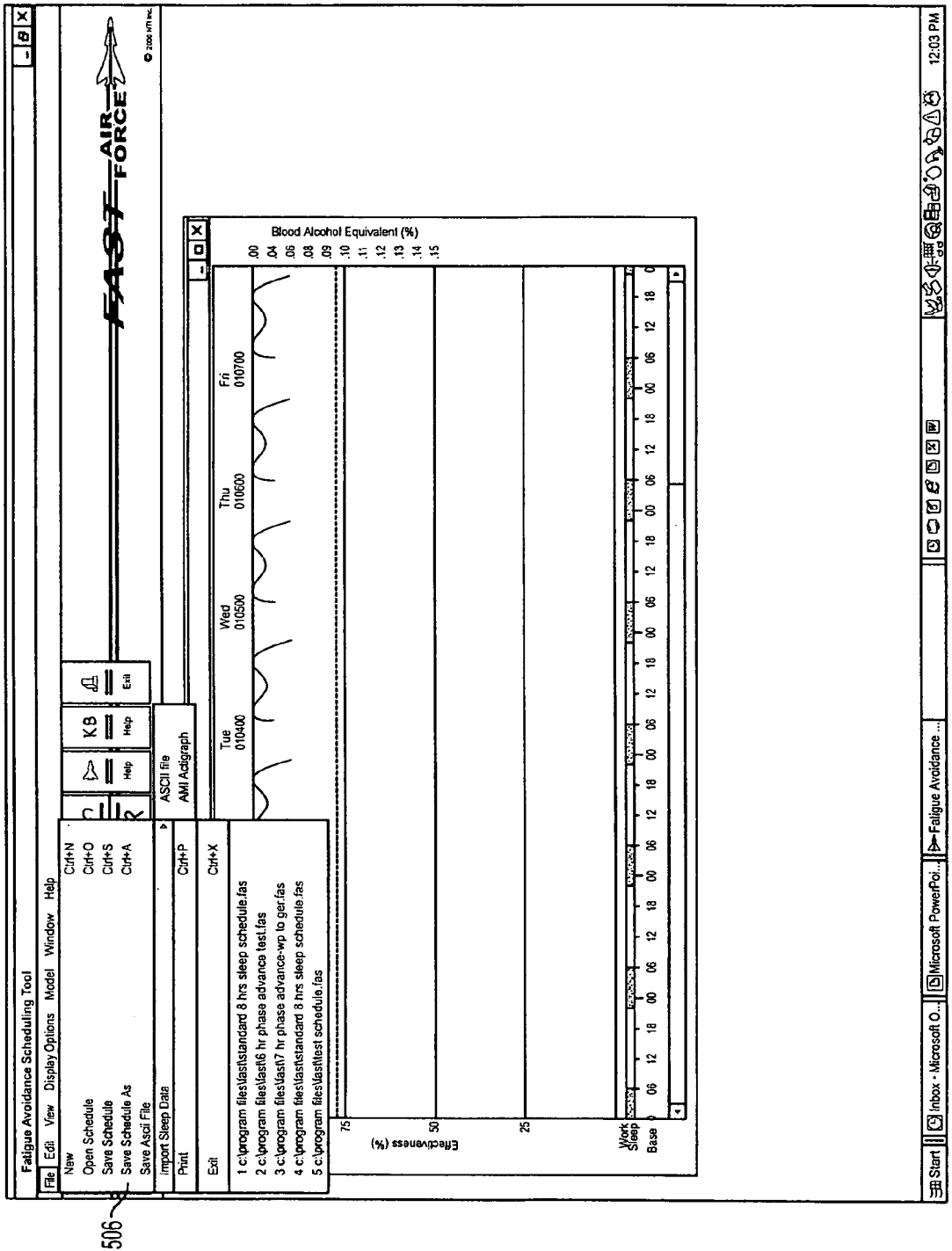
FIG. 28 is a screen for importing sleep data of the interface for the system for evaluating the effectiveness of a person to perform a task according to the present invention.

A user can import sleep data into the system using the interface. The sleep data can be either an ASCII text file or an AMI Actigraph file. To import such data the user selects the IMPORT SLEEP DATA option from the FILE drop-down screen 506, as shown in FIG. 28, and then selects either ASCII or AMI Actigraph as the data type.

The FILE drop-down screen 506 also has a SAVE SCHEDULE option and a PRINT option. The SAVE SCHEDULE option is for saving a previously opened file after making changes or after its creation. The PRINT option produces a paper print-out of the schedule, either as a graphic display or a table, depending upon the view option selected.

Figure 29:
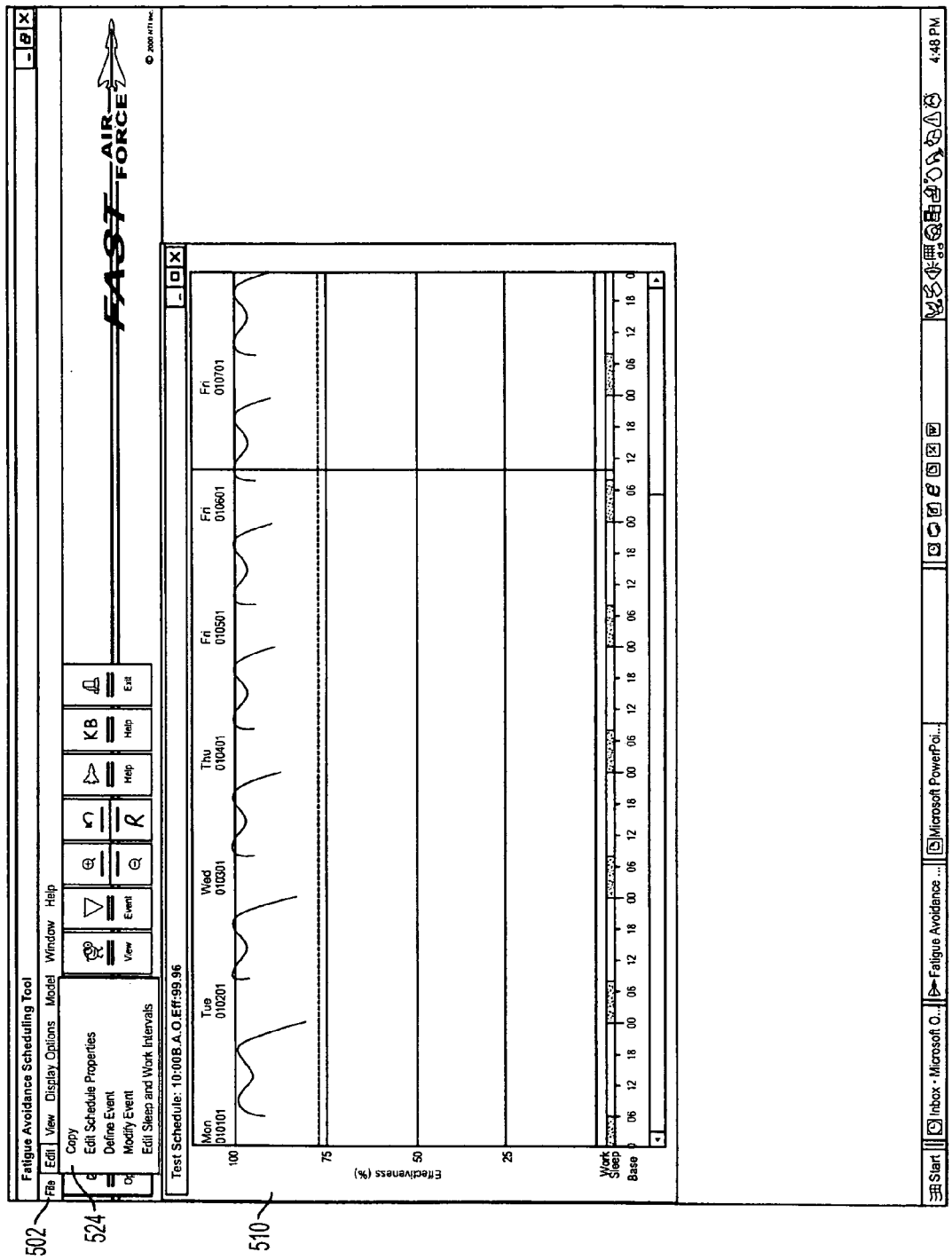
FIG. 29 is an edit menu screen for the interface of the system for evaluating the effectiveness of a person to perform a task according to the present invention.

From the main toolbar 502 a user may select the EDIT option, which produces an EDIT drop-down screen 524, shown in FIG. 29, and may include the following five options: COPY, EDIT SCHEDULE PROPERTIES, DEFINE EVENT, MODIFY EVENT, and EDIT SLEEP AND WORK INTERVALS, all of which allow the user to edit schedules.

Figure 30:
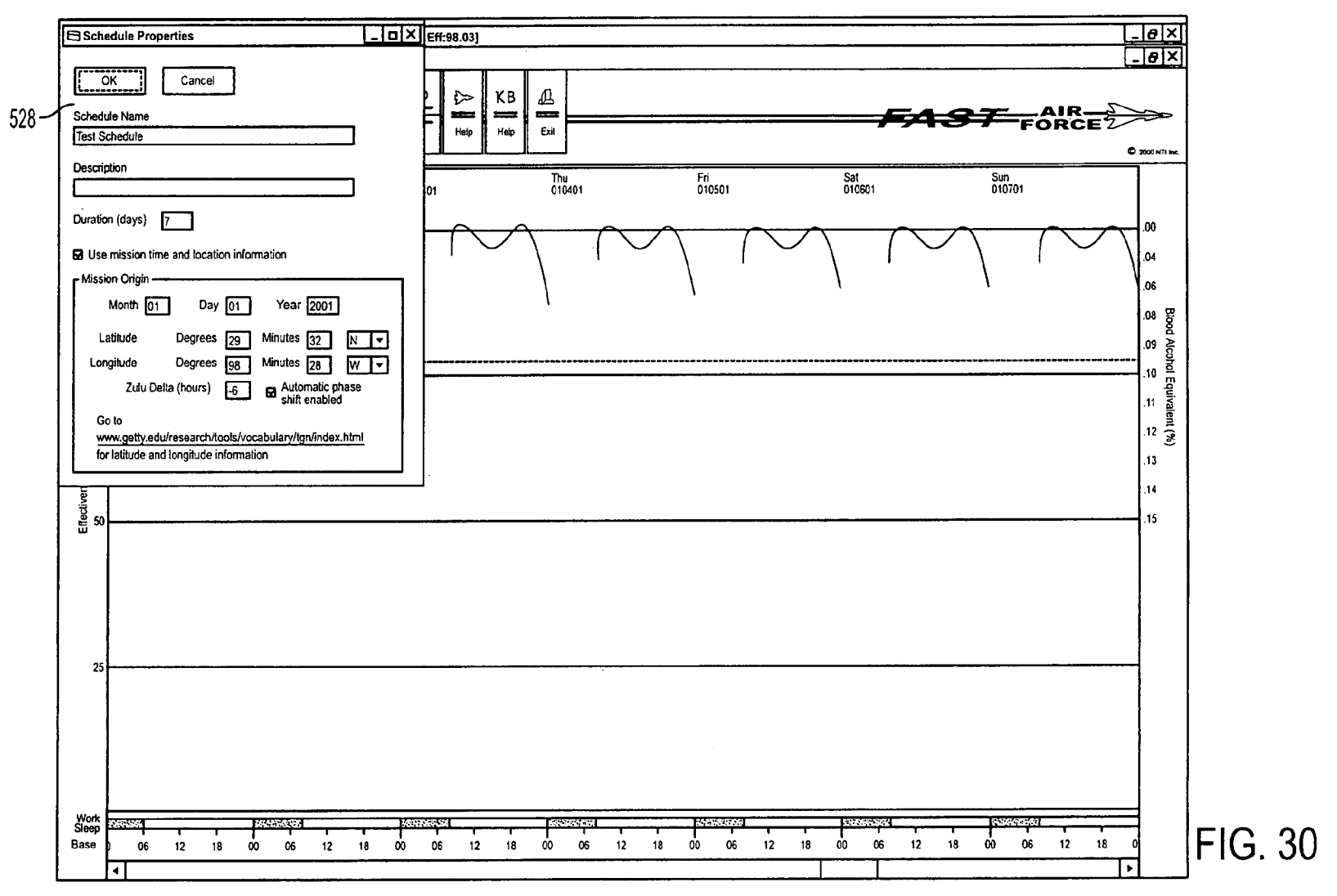

The EDIT SCHEDULE option in the screen 524 produces the schedule properties screen 526, illustrated in FIG. 30, and is the same as the schedule properties screen 514 shown in FIG. 25. Unlike the schedule properties screen 514, the fields of the screen 526 are not empty, but rather contain the previously entered data pertaining to the selected schedule.

Figure 31:
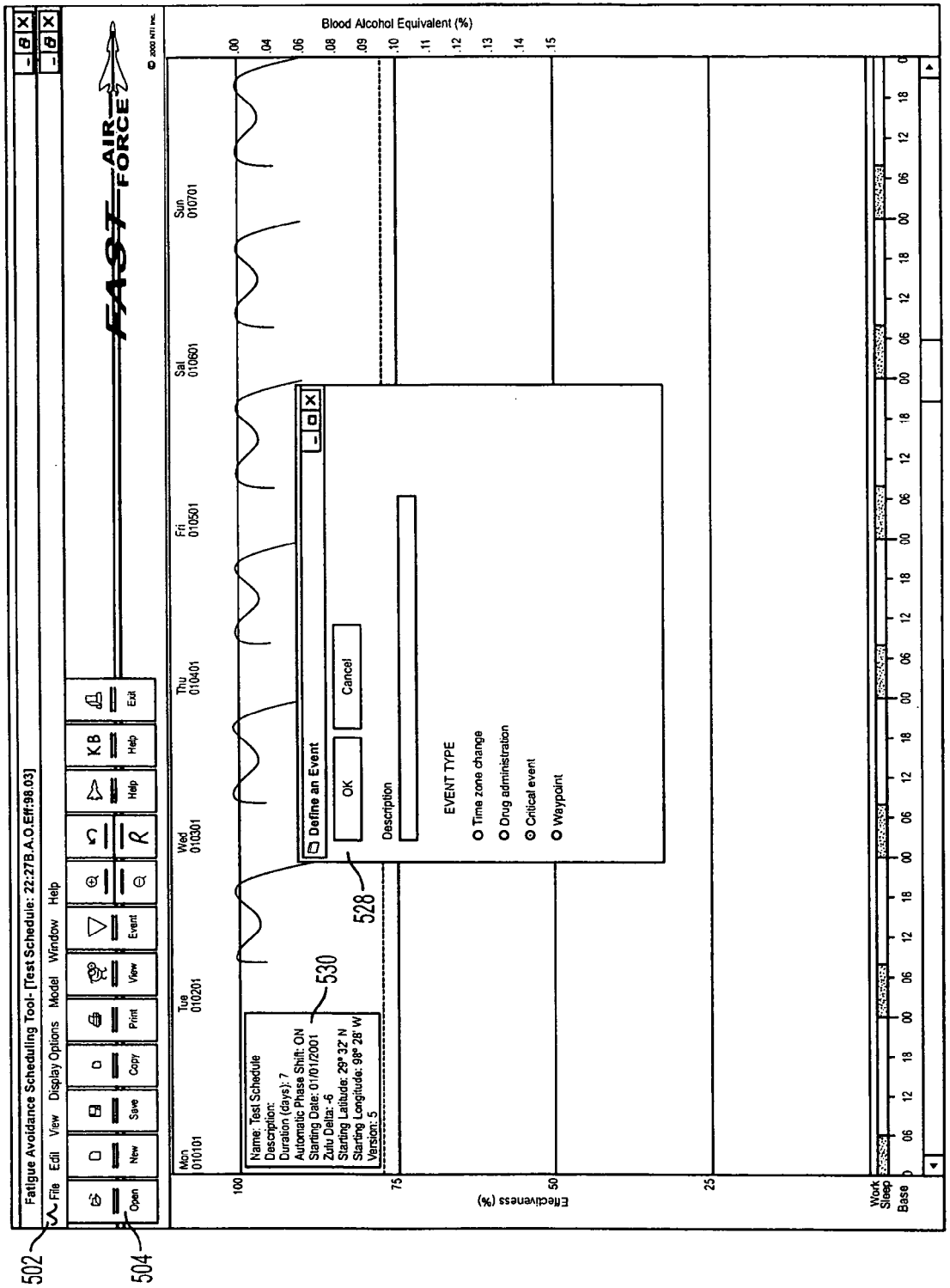
FIG. 31 is a define event screen of the interface for the system for evaluating the effectiveness of a person to perform a task according to the present invention.

The DEFINE EVENT option in the drop-down screen 524 produces the define event screen 528, shown in FIG. 31, when selected. From the define event screen 528 a user can select from a number of events, which may include a time zone change, a fatigue intervention (e.g., a drug administration), a waypoint, and a critical event which can be labeled, such as take-off, landing, or other performance critical time point. . Any combination of such events may be combined in a single simulation. Some events may alter the predicted performance as shown in screen 510, such as way pointes and drug deliveries, and other events are primarily for information display, such as critical events.

Figure 32:
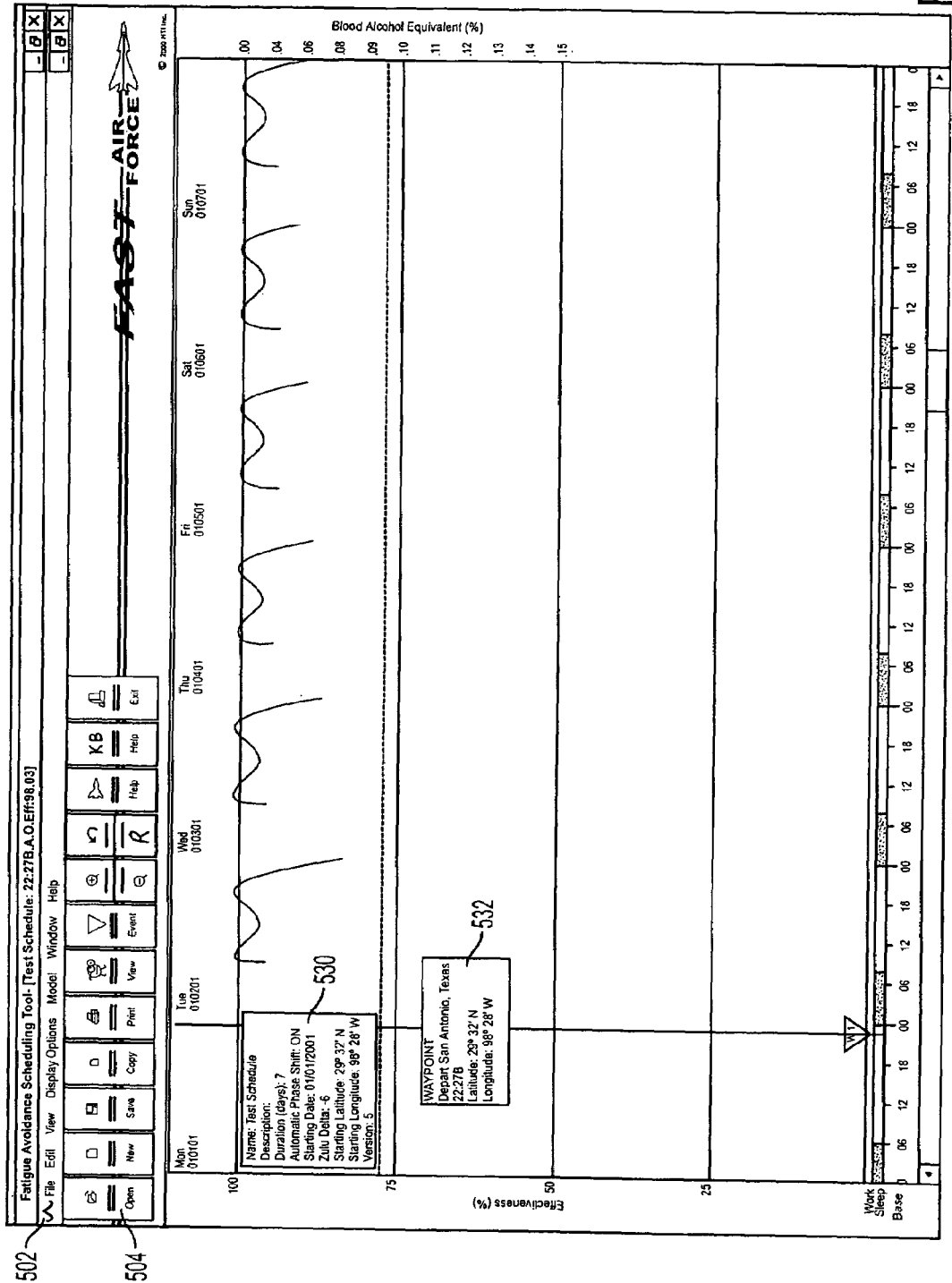
FIG. 32 is an event description box of the interface for the system for evaluating the effectiveness of a person to perform a task according to the present invention.
Figure 33:
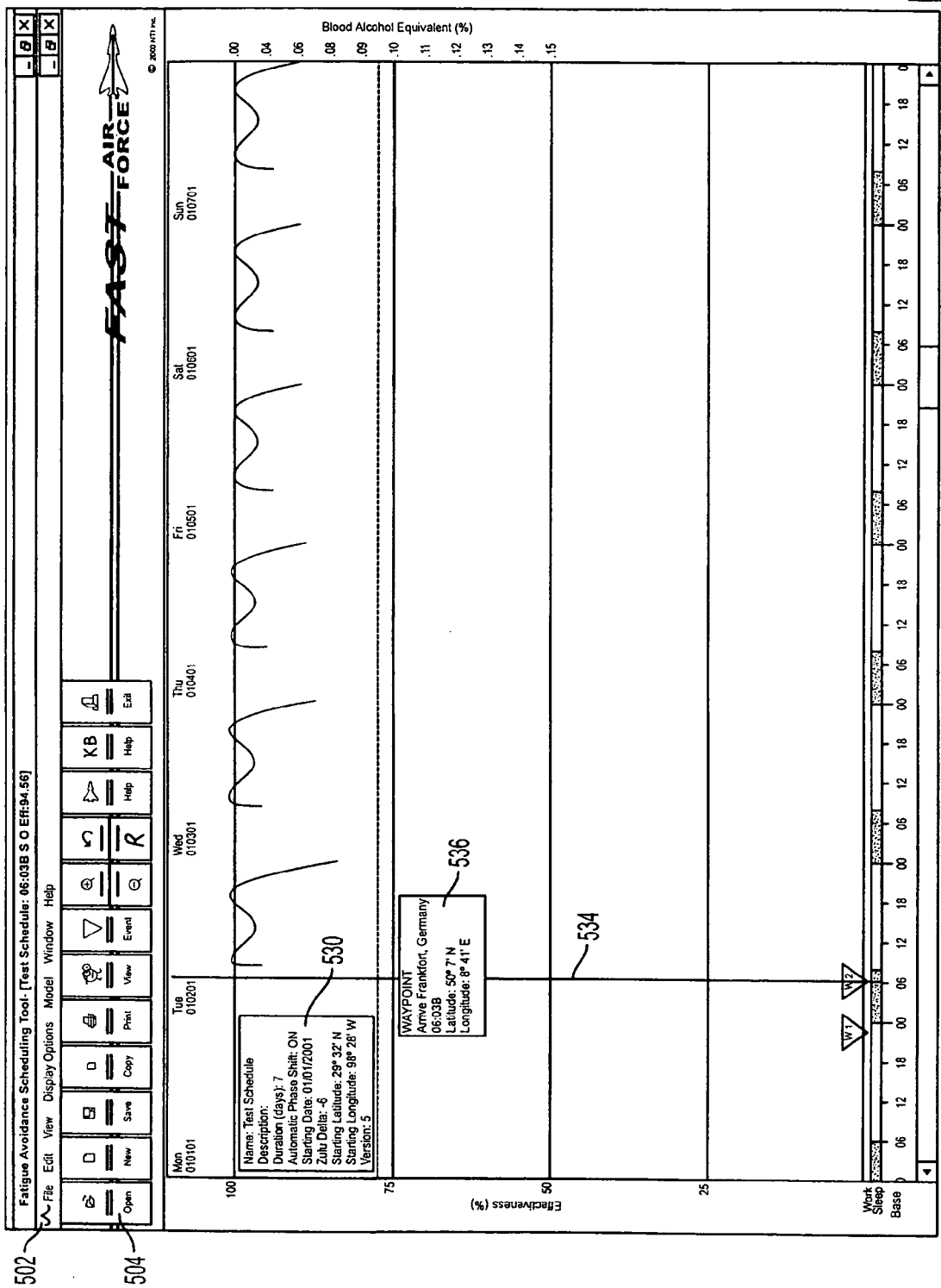
FIG. 33 is screen showing a defined second event of the interface for the system for evaluating the effectiveness of a person to perform a task according to the present invention.

As an example, as illustrated in FIG. 32, an event, such as a waypoint, may be added. Here the detailed information about the schedule is shown in box 530, in which name, description, automatic phase shift status, start date, Zulu delta, starting latitude and longitude and version are illustrated. A waypoint is added through the define event option and screen 528, and is shown in box 532. In this example the information includes a departure time of 22:27B from San Antonio, Tex. at latitude 29.32° N. and Longitude 98.28° W. A second event 534 may be added, as shown in FIG. 33, in which a second waypoint is shown at Frankfort, Germany, at 6:03B, and latitude 50.7° N. and Longitude 8.41° E. contained in box 536. Time indication followed by the letter 'B' indicate that the time is expressed as the subject's base time. That is, 'B' time is the base time at the original location and represents the subject's physiological time at the start of the schedule, not necessarily the time at the present location. Similarly 'Z' time is Zulu time.

Waypoints may be used to indicate when a subject changes location. In the above example, a first waypoint may be entered to indicate the subject is departing San Antonio, Tex. at 22:27 base time. A second waypoint may be entered to indicate to indicate the subject arrives at Frankfurt, Germany at 6:03 base time. Using the above model and algorithms, the system may calculate a great circle route from the departure waypoint to the arrival waypoint, and interpolate the actual sunlight along that path. The sunlight information may then be displayed on one or more interface screens as described above.

Figure 34:
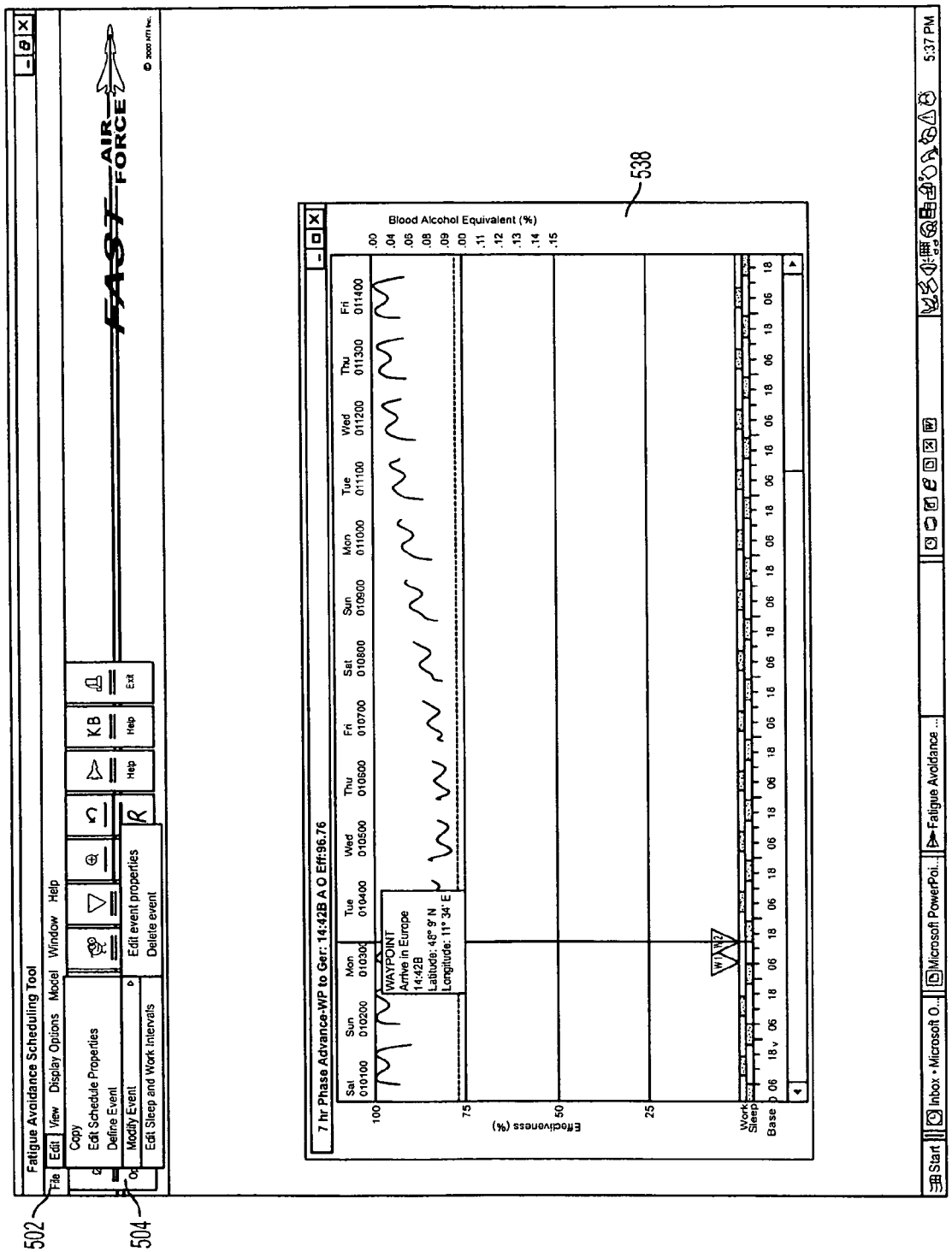
FIG. 34 is an edit or delete event properties screen of the interface for the system for evaluating the effectiveness of a person to perform a task according to the present invention.

When the MODIFY EVENT option is selected from the drop-down screen 524, screen 538, as illustrated in FIG. 34, is produced so that one of the previously entered events can be modified. The modified event will have corresponding changes in the schedule screen 510, calculated based on the above description with reference to FIGS. 1–16.

Figure 35:
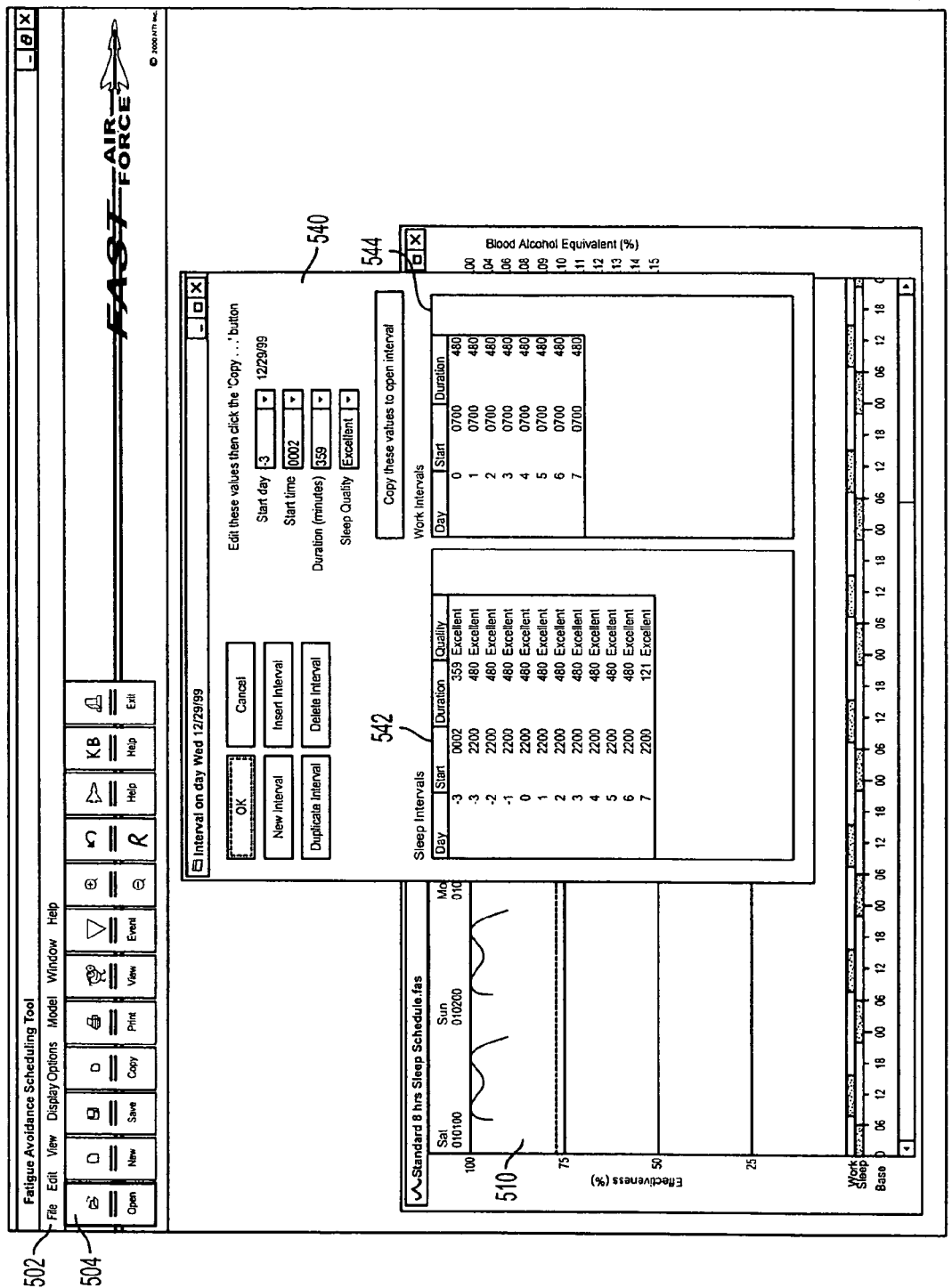
FIG. 35 is a screen for editing sleep and work intervals using a table entry form for the interface for the system for evaluating the effectiveness of a person to perform a task according to the present invention.

If the EDIT SLEEP AND WORK INTERVALS option is selected from the drop-down screen 524, the interval screen 540, shown in FIG. 35, is produced. From the interval screen 540 a user can add a new interval, insert an interval, duplicate an interval, or delete an interval. Each interval includes a start day and time, a duration, and a sleep quality indication. In addition, the screen 540 includes tables 542 for sleep intervals and 544 for work intervals. Any changes made using the foregoing options will be reflected in the table 542 and 544 based on the values input by the user.

Figure 36:
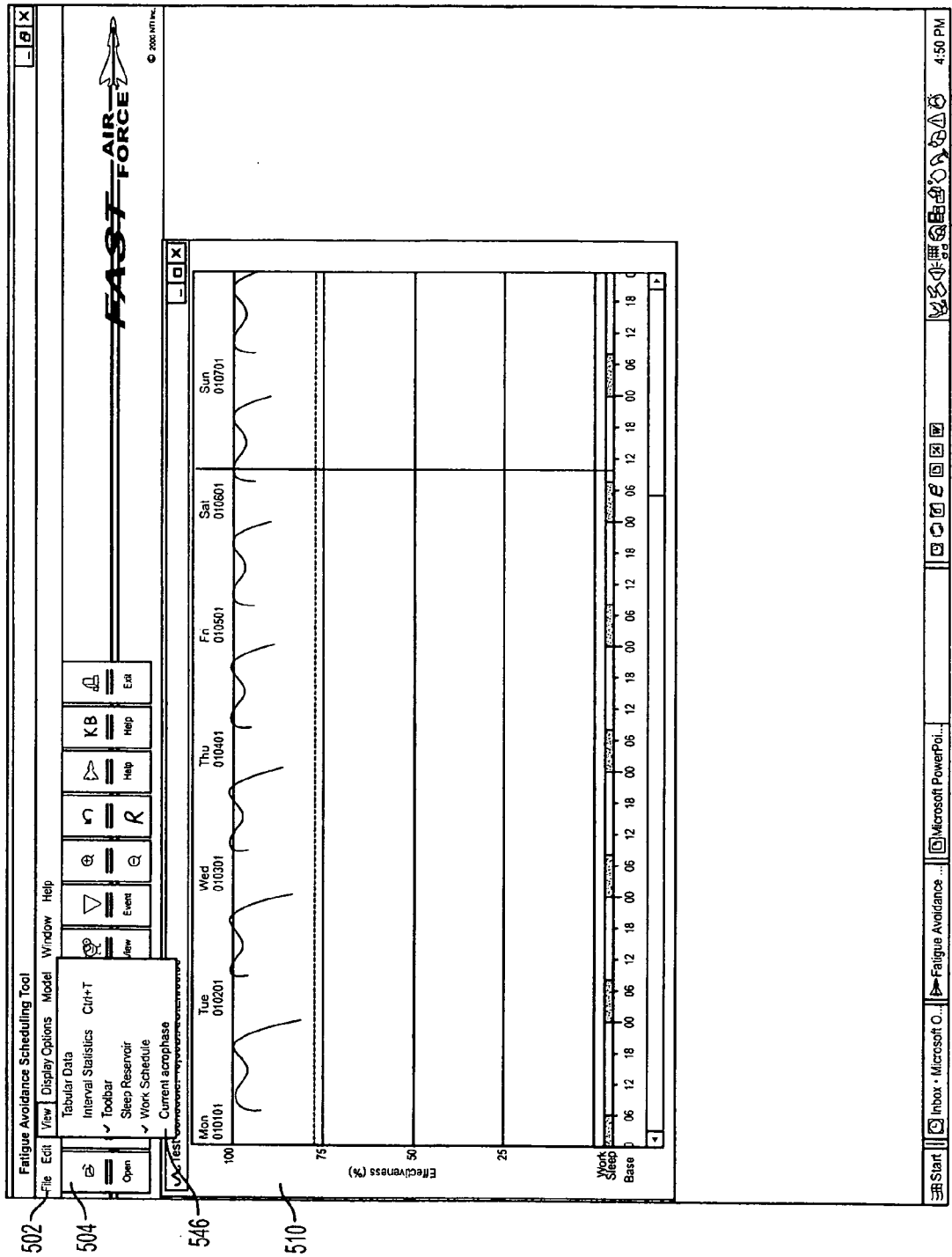
FIG. 36 is a view menu of the interface for the system for evaluating the effectiveness of a person to perform a task according to the present invention.

The user has multiple options for viewing schedules. The VIEW option, in the main toolbar 502 or secondary toolbar 504, provides access to the different viewing options. Referring to FIG. 36, when the VIEW option is selected from the main toolbar 502, a drop-down screen 546 is displayed, and contains TABULAR DATA, INTERVAL STATISTICS, TOOLBAR, SLEEP RESERVOIR, WORK SCHEDULE, and CURRENT ACROPHASE options.

Figure 37:
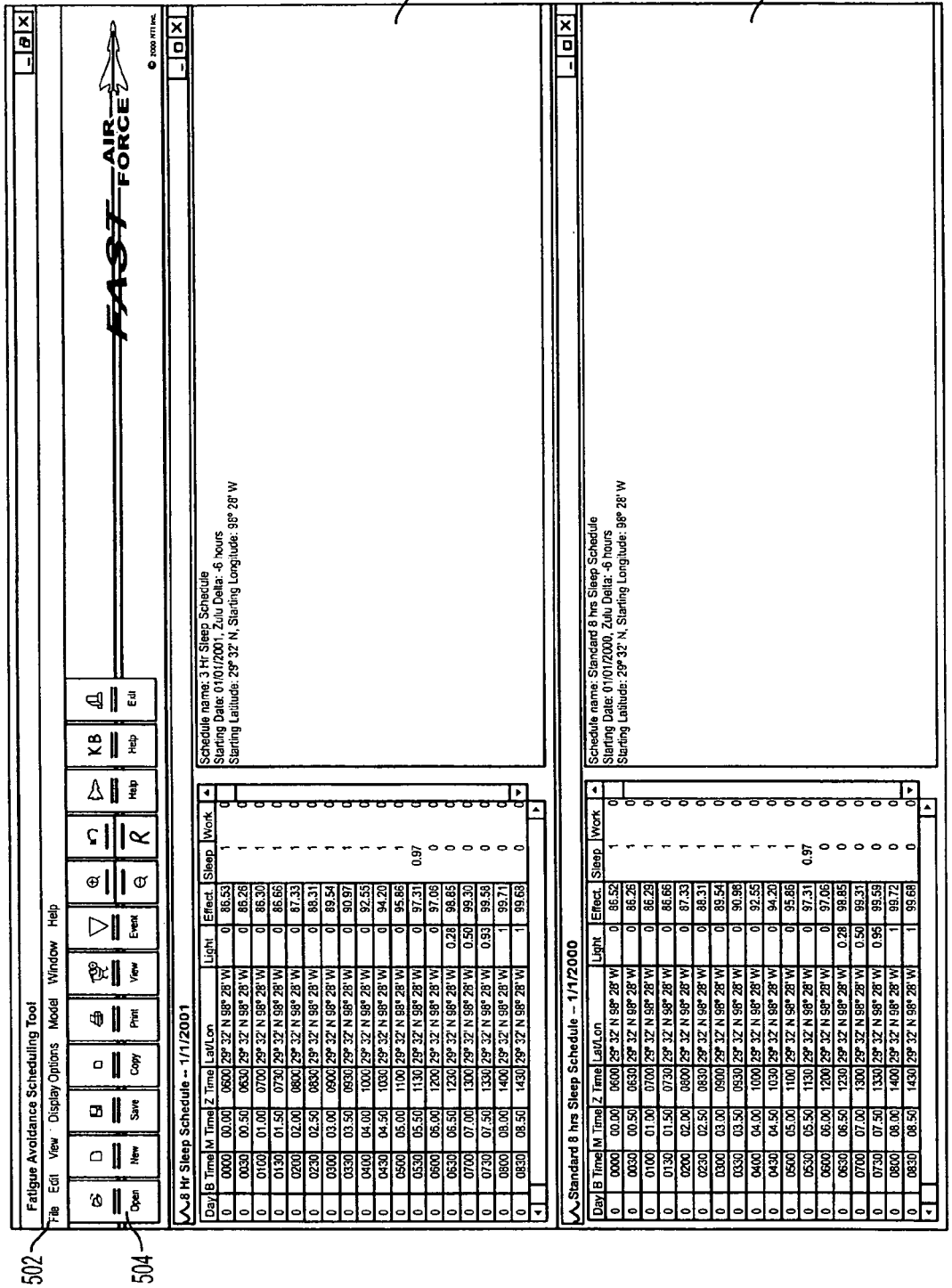
FIG. 37 is a screen showing tables for two schedules for the interface for the system for evaluating the effectiveness of a person to perform a task according to the present invention.

When the TABULAR option in the drop-down screen 546 is selected a tabular view of the schedule is presented. FIG. 37 illustrates an example where two schedules 548 and 549 are illustrated in tabular form. Each table includes similar data for each respective schedule. This information includes the day, the beginning time (B Time), mission elapsed time (M Time), which is the time in hours from midnight on day one, time at the Prime Meridian (Z Time), latitude and longitude (Lat/Long), Light, Effectiveness rating, and sleep and work indicators that show if the time period is a sleep period or a work period.

Figure 38:
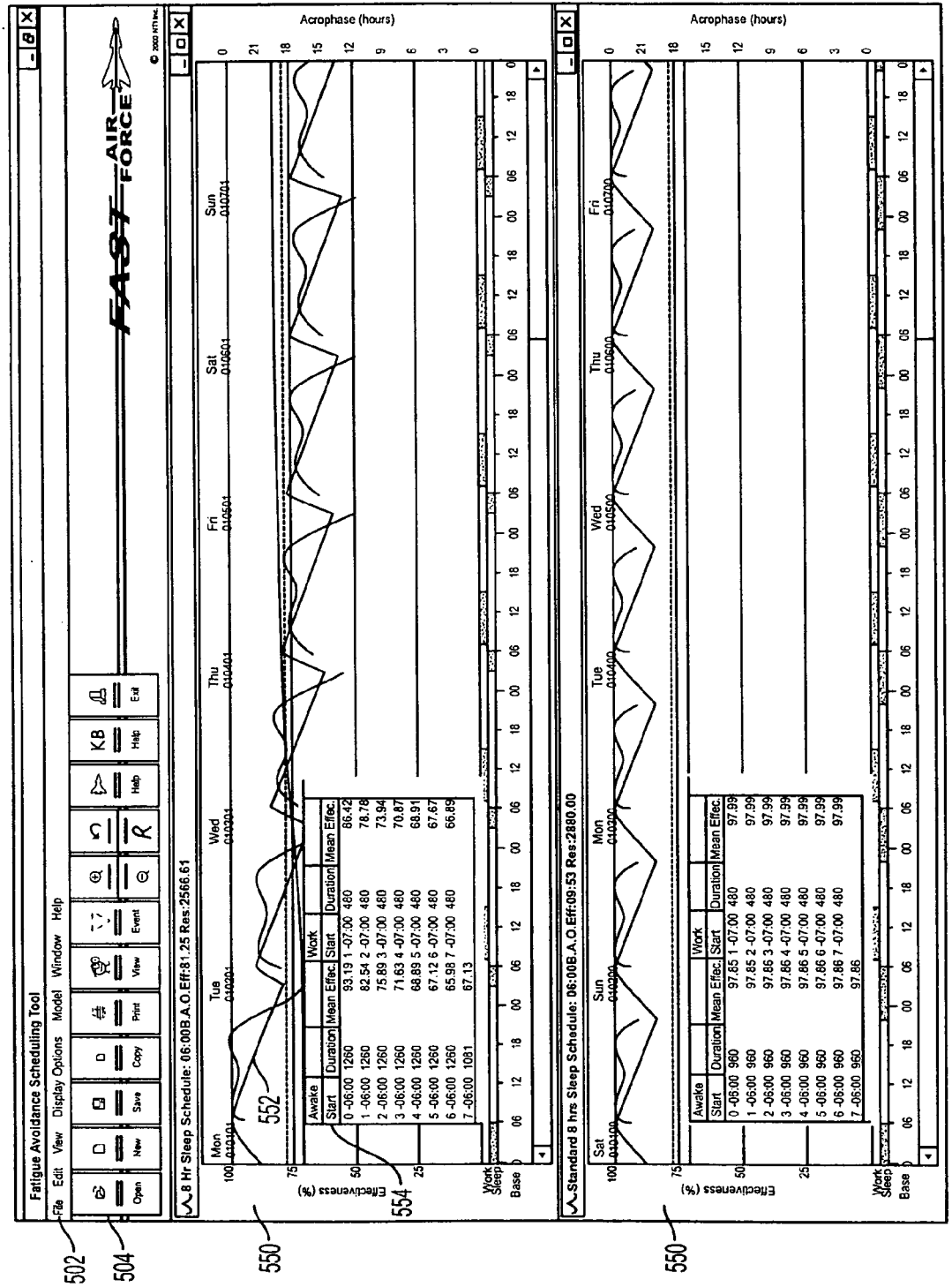
FIG. 38 shows the screen shown in FIG. 24 having further interval statistics screens for each schedule according to the interface for the system for evaluating the effectiveness of a person to perform a task of the present invention.

Using the INTERVAL STATISTICS option in the drop-down screen 546, a user is presented with interval statistics screen 550 as illustrated in FIG. 38. FIG. 38 shows two schedules tiled horizontally, however, a single schedule may be displayed. The schedule is created based on the data contained in the schedule file and calculated as described above with respect to FIGS. 1–16. Each interval statistics screen 550 has a mean effectiveness 552 for all awake periods and work periods. Mean effectiveness is the arithmetic average of the effectiveness scores for each minute in the defined interval, either awake period or work period. The table 554, containing the tabular data for the schedule 550, may be dragged to any portion of the schedule 550.

Figure 39:
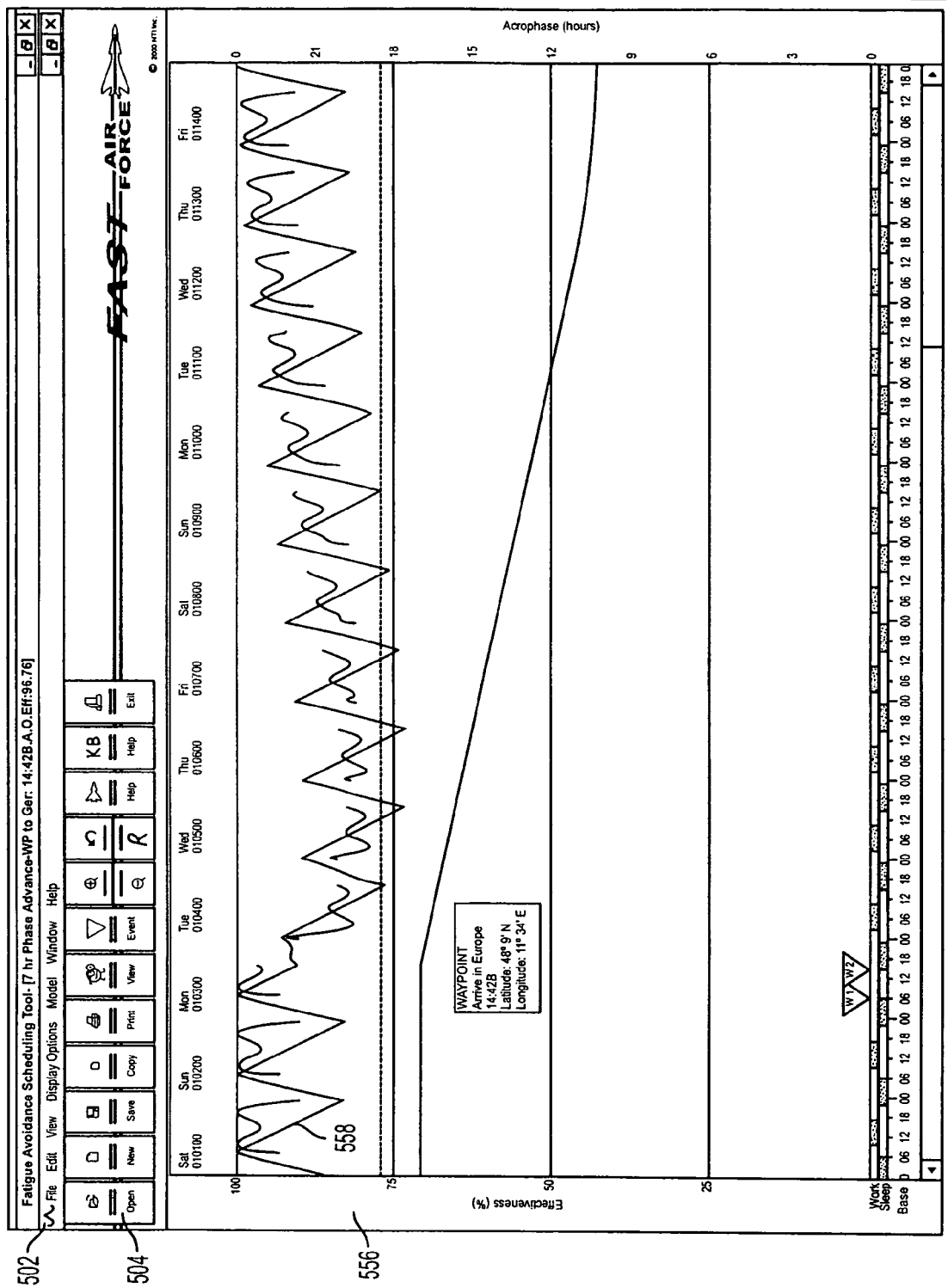
FIG. 39 is a screen showing a reservoir balance line according to the interface for the system for evaluating the effectiveness of a person to perform a task according to the present invention.
Figure 40:
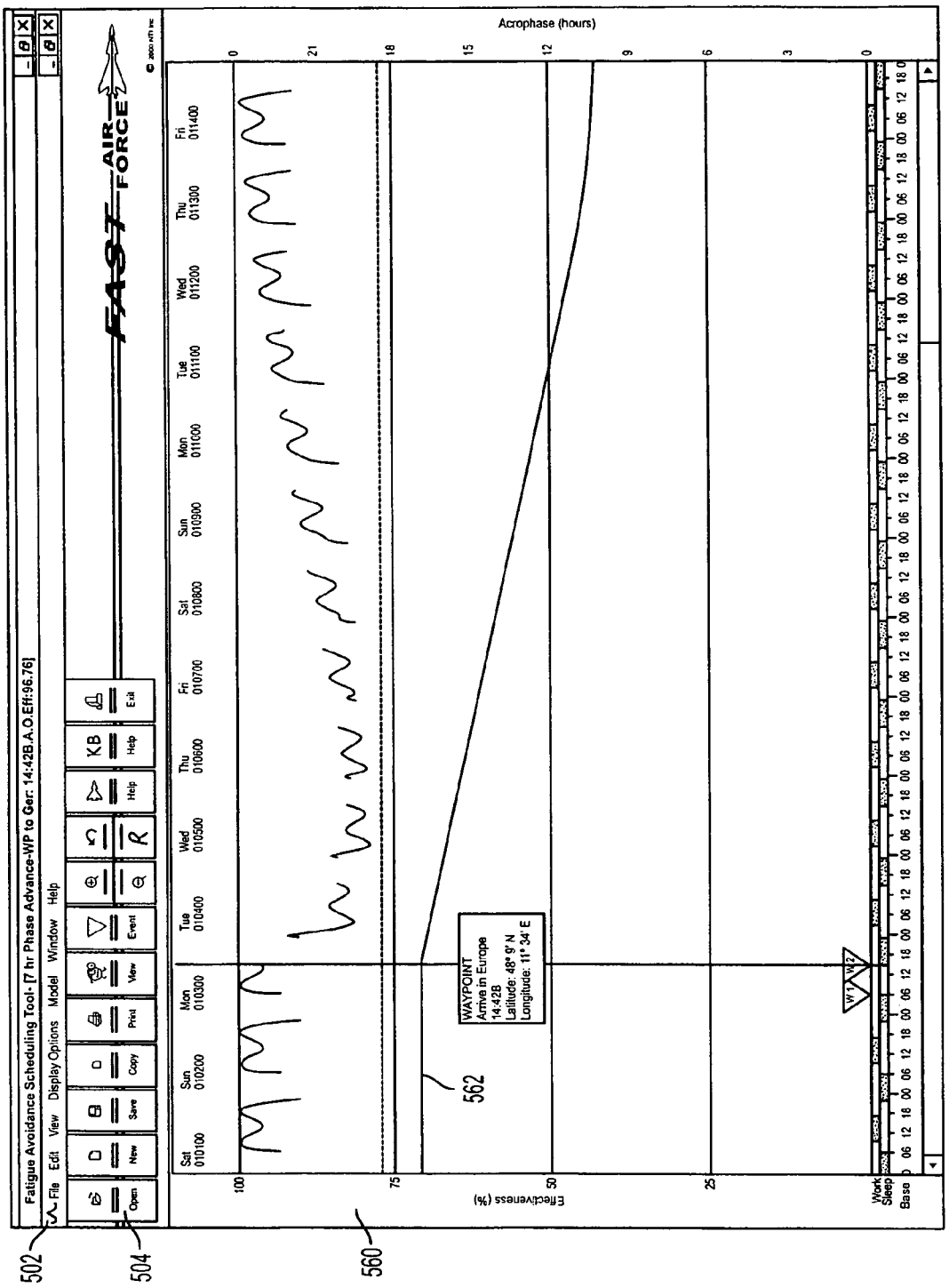
FIG. 40 is a schedule screen illustrating an acrophase line according to the interface for the system for evaluating the effectiveness of a person to perform a task according to the present invention.

The schedule screen 556 shown in FIG. 39 is presented to a user when the SLEEP RESERVOIR option is selected from the drop-down screen 546. In the schedule screen 556 the reservoir balance line 558 provides a quick visual indication of the balance in the sleep reservoir and takes a rough zigzag shape, for a person that has a regular sleep-pattern every day. The CURRENT ACROPHASE option in the drop-down screen 546 produces the schedule screen 560, shown in FIG. 40, in which the acrophase is represented by line 562.

Figure 41:
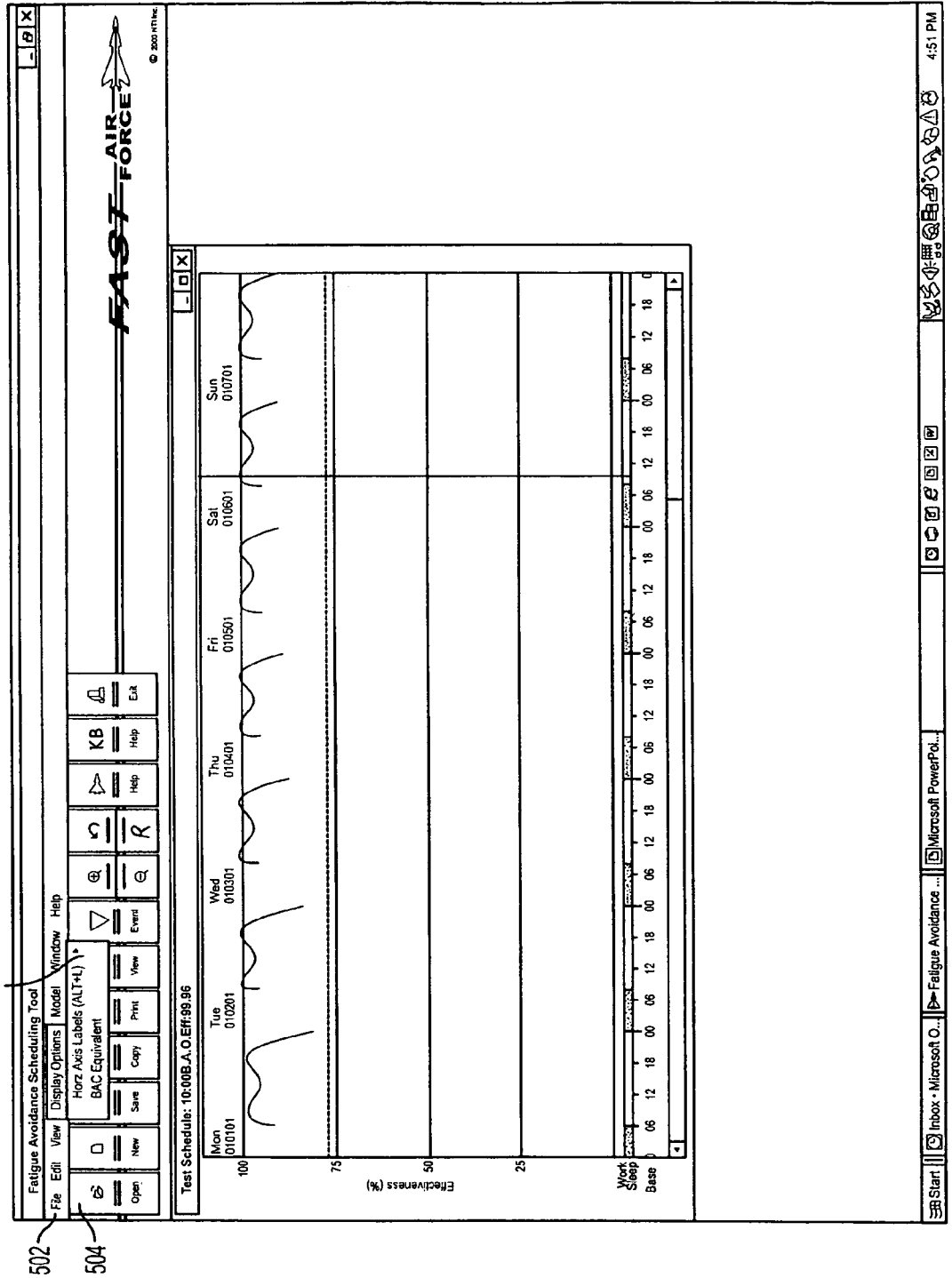
FIG. 41 is a display options menu of the interface for the system for evaluating the effectiveness of a person to perform a task according to the present invention.
Figure 42:
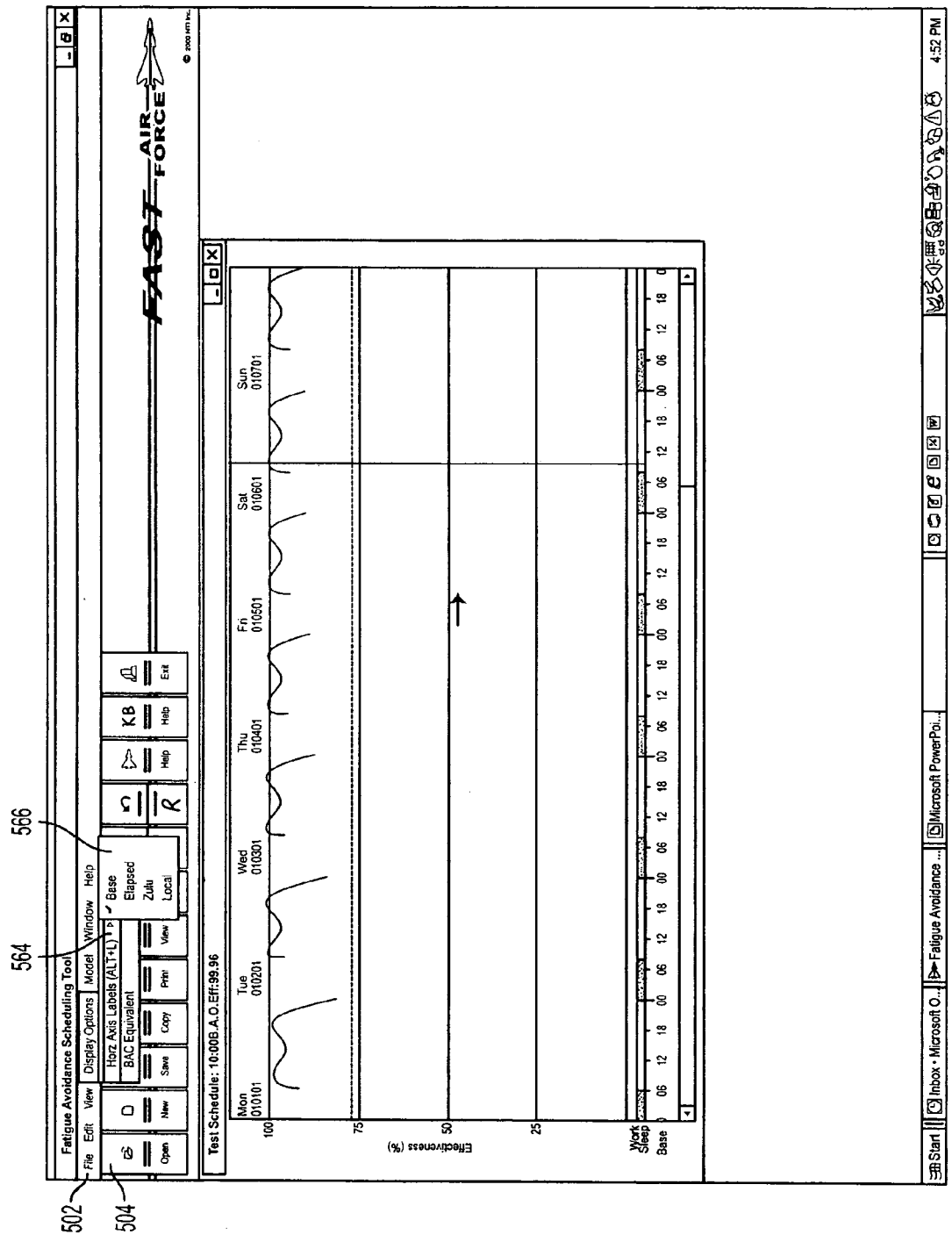
FIG. 42 is a horizontal axis labels screen of the interface for the system for evaluating the effectiveness of a person to perform a task according to the present invention.
Figure 43:
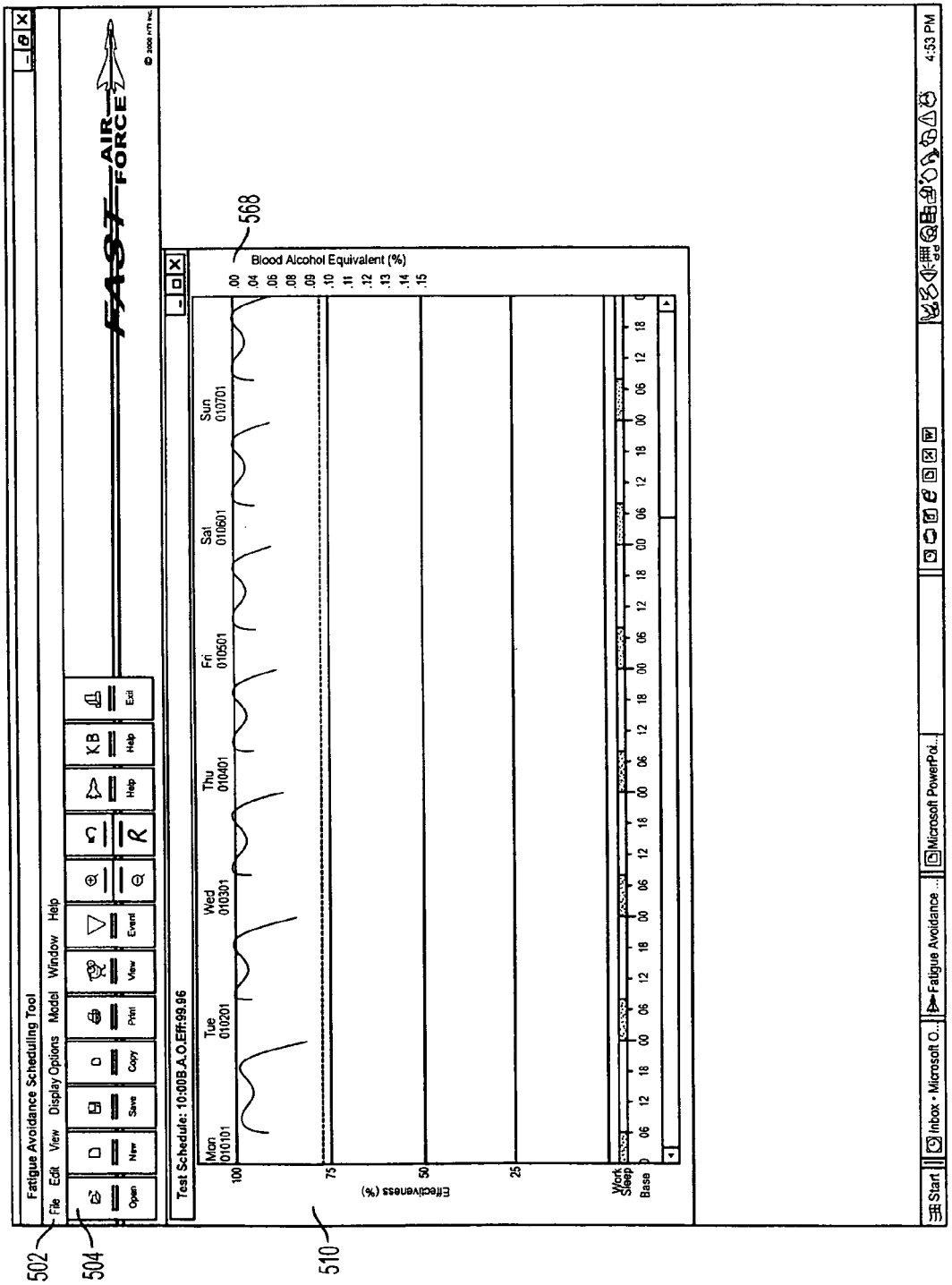
FIG. 43 is a blood alcohol equivalent right vertical axis screen of the interface for the system for evaluating the effectiveness of a person to perform a task according to the present invention.

The DISPLAY OPTIONS in the main toolbar 502 produces a drop-down screen 564, as illustrated in FIG. 41 and includes two options: HORIZONTAL AXIS LABELS and BAL (Blood Alcohol Level) EQUIVALENT. Selection of the HORIZONTAL AXIS LABELS option produces the drop down screen 566, illustrated in FIG. 42, and contains three options: BASE, ELAPSED, and ZULU. These three options provide the user with three choices for the time reference across the horizontal axis. The BAL Equivalent option produces a blood alcohol level equivalent 568 on the right vertical axis of the schedule 510, as shown in FIG. 43. The BAL Equivalence indicates the performance equivalence of the subject during his or her sleep cycle in terms of blood alcohol content, as is known in the art. That is, the BAL Equivalence is that level of alcohol that produces a similar change in reaction time as would be expected with the associated level of effectiveness from the SAFTE model described above.

Figure 44:
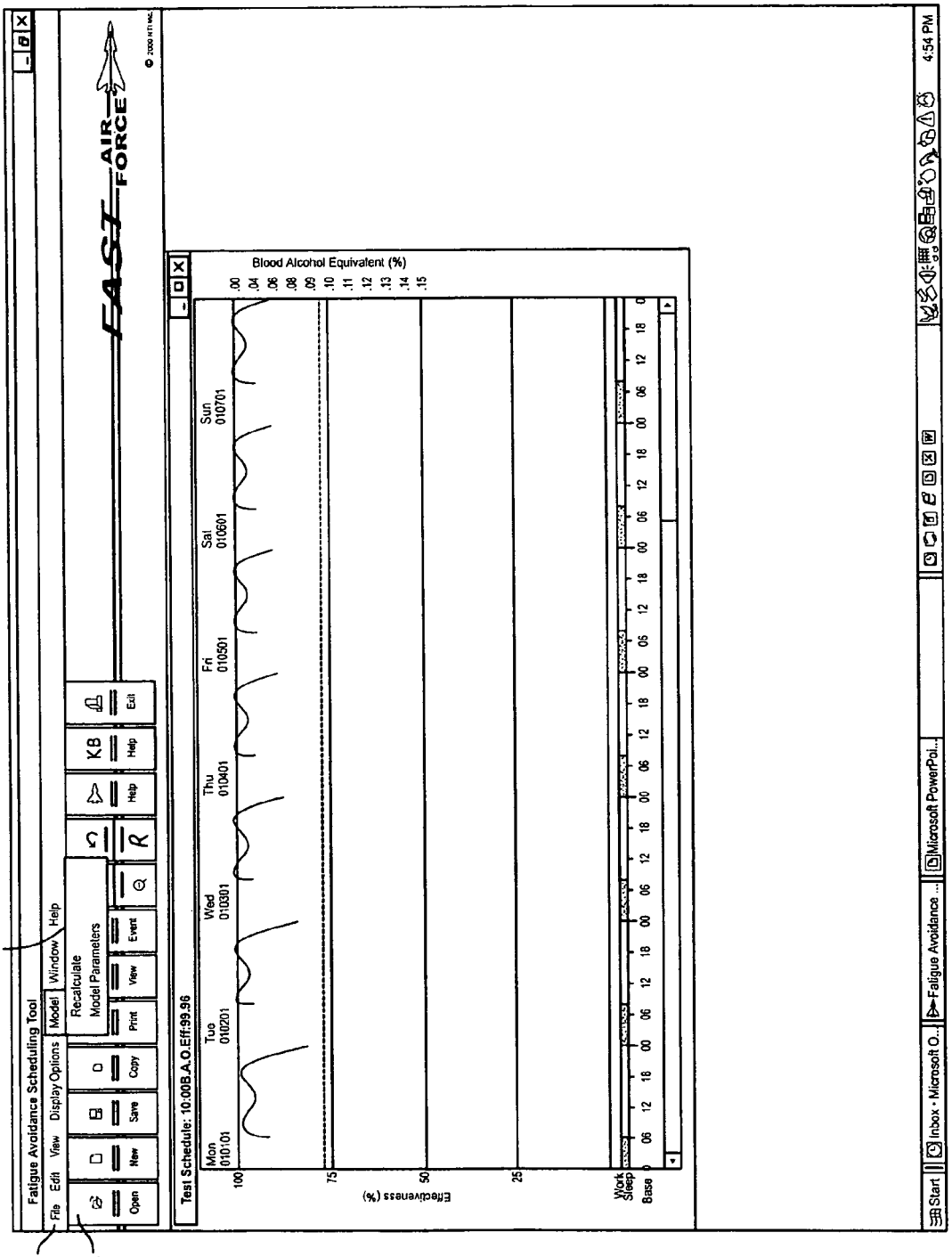
FIG. 44 is a model menu of the interface for the system for evaluating the effectiveness of a person to perform a task according to the present invention.
Figure 45:
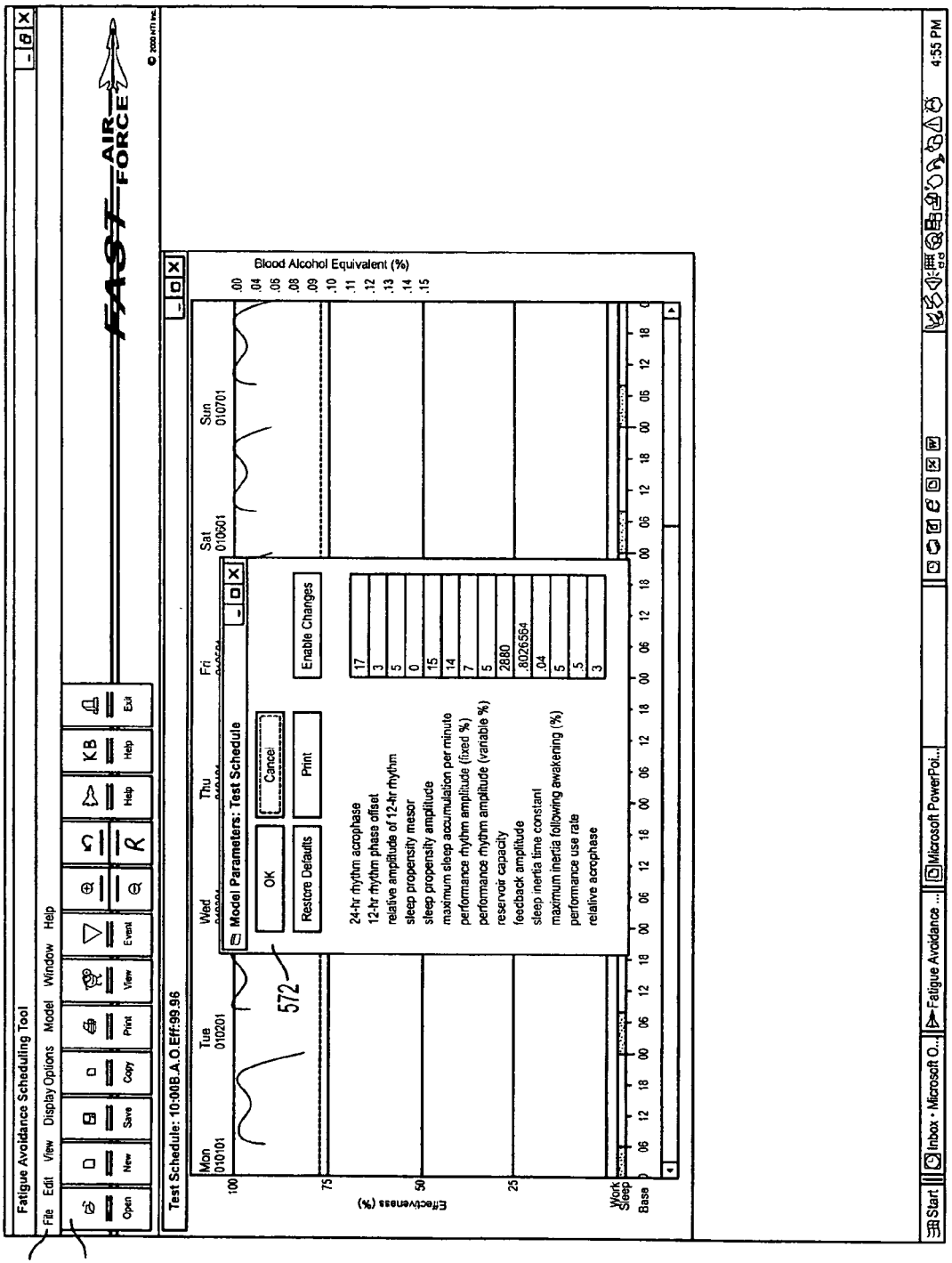
FIG. 45 is a model parameter screen of the interface for the system for evaluating the effectiveness of a person to perform a task according to the present invention.

When the MODEL option is selected from the toolbar 502 a drop-down screen 570, shown in FIG. 44, is produced. The screen 570 provides two choices, namely, RECALCULATE and MODEL PARAMETERS. The recalculate selection will calculate and re-plot the effectiveness prediction and is used whenever the sleep schedule information is changed. Recalculate may also be selected from the tool bar buttons, 504. By selecting the MODEL PARAMETERS option, the model parameter screen 572, shown in FIG. 45, is presented. The model parameter screen 572 enables the user to change schedule parameters, which may include a 24 hour rhythm acrophase, a 12 hour rhythm phase offset, the relative amplitude of the 12 hour rhythm, the sleep propensity mesor, the sleep propensity amplitude, the maximum sleep accumulation per minute, the performance rhythm amplitude as either a fixed or variable percentage, the reservoir capacity, the feedback amplitude, the sleep inertia constant, the maximum inertia following awakening, the performance use rate, and the relative acrophase.

After entering values for the foregoing parameters, screen 572 allows the user to save or delete the values, or to restore the original values. The user may also choose to print the values. In order to preserve existing schedule data, the capability to change the data through screen 572 may require a password. Model parameters are saved with the schedule file. This permits a schedule to be tailored to the specific characteristics of the person under study, if known. Once new parameters are entered and the user selects "OK", the schedule predictions are automatically recalculated.

Figure 46:
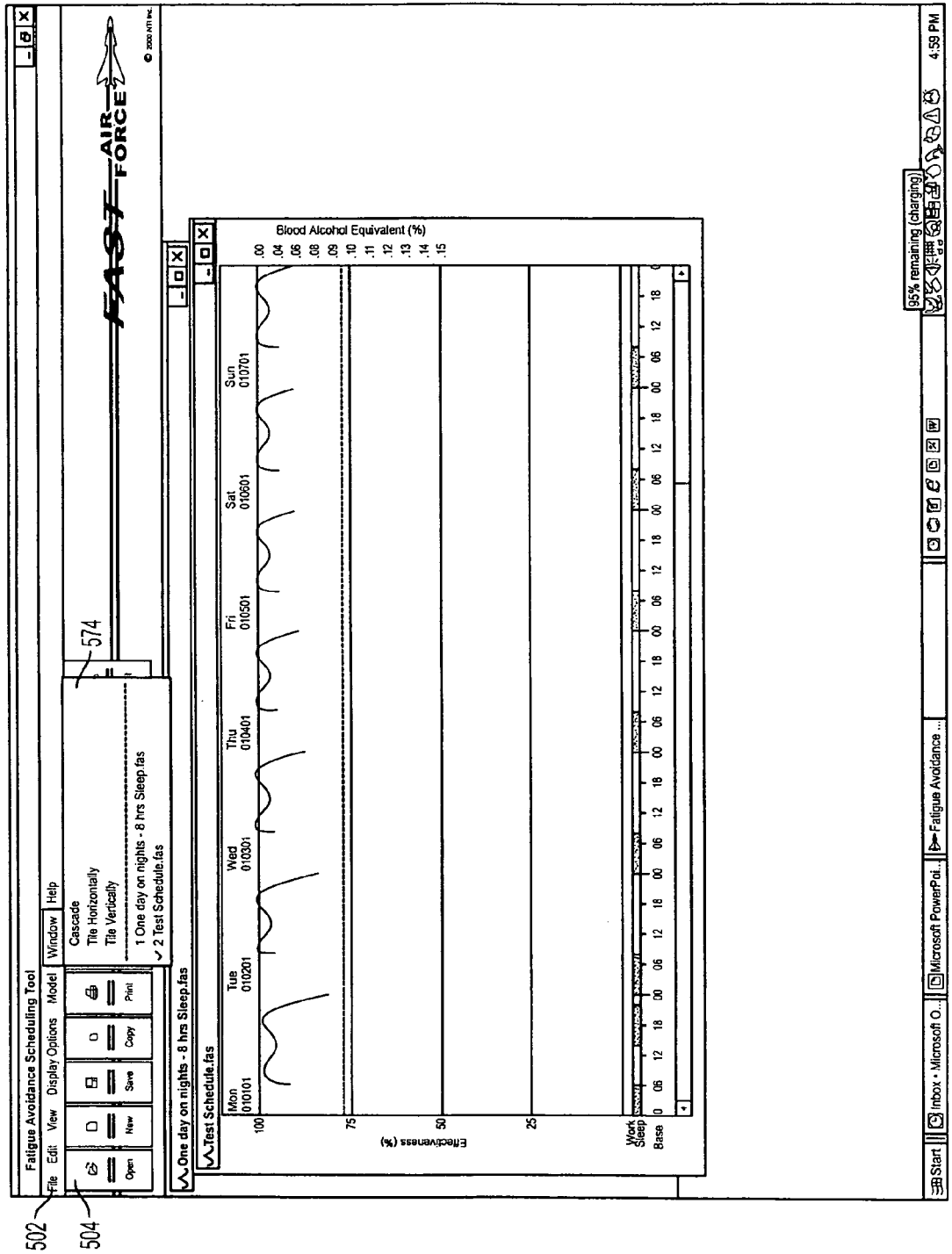
FIG. 46 is a menu for choosing the arrangement of multiple windows according to the interface for the system for evaluating the effectiveness of a person to perform a task according to the present invention.
Figure 47:
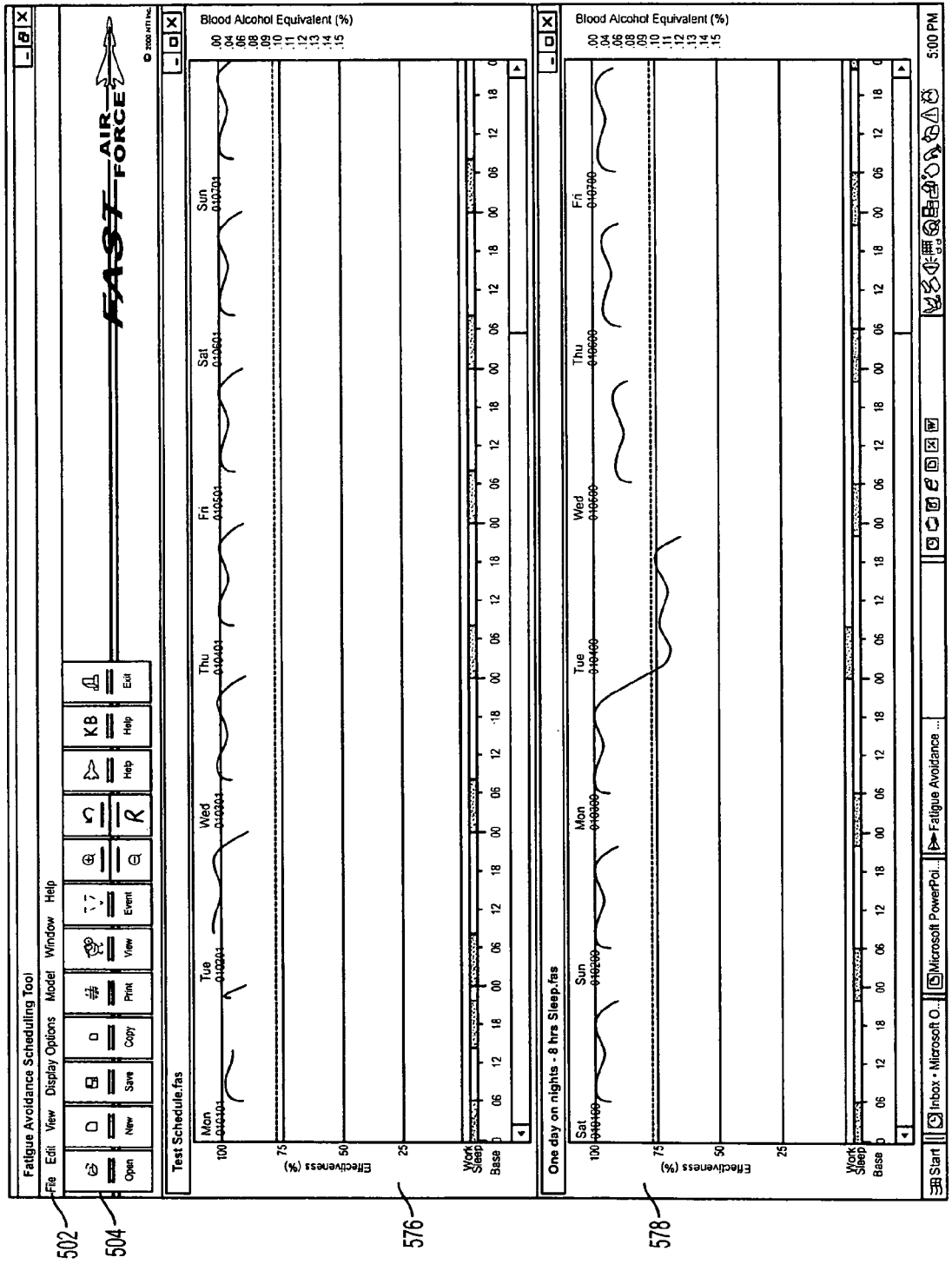
FIG. 47 is a screen showing two schedules tiled horizontally according to the interface for the system for evaluating the effectiveness of a person to perform a task according to the present invention.
Figure 48:
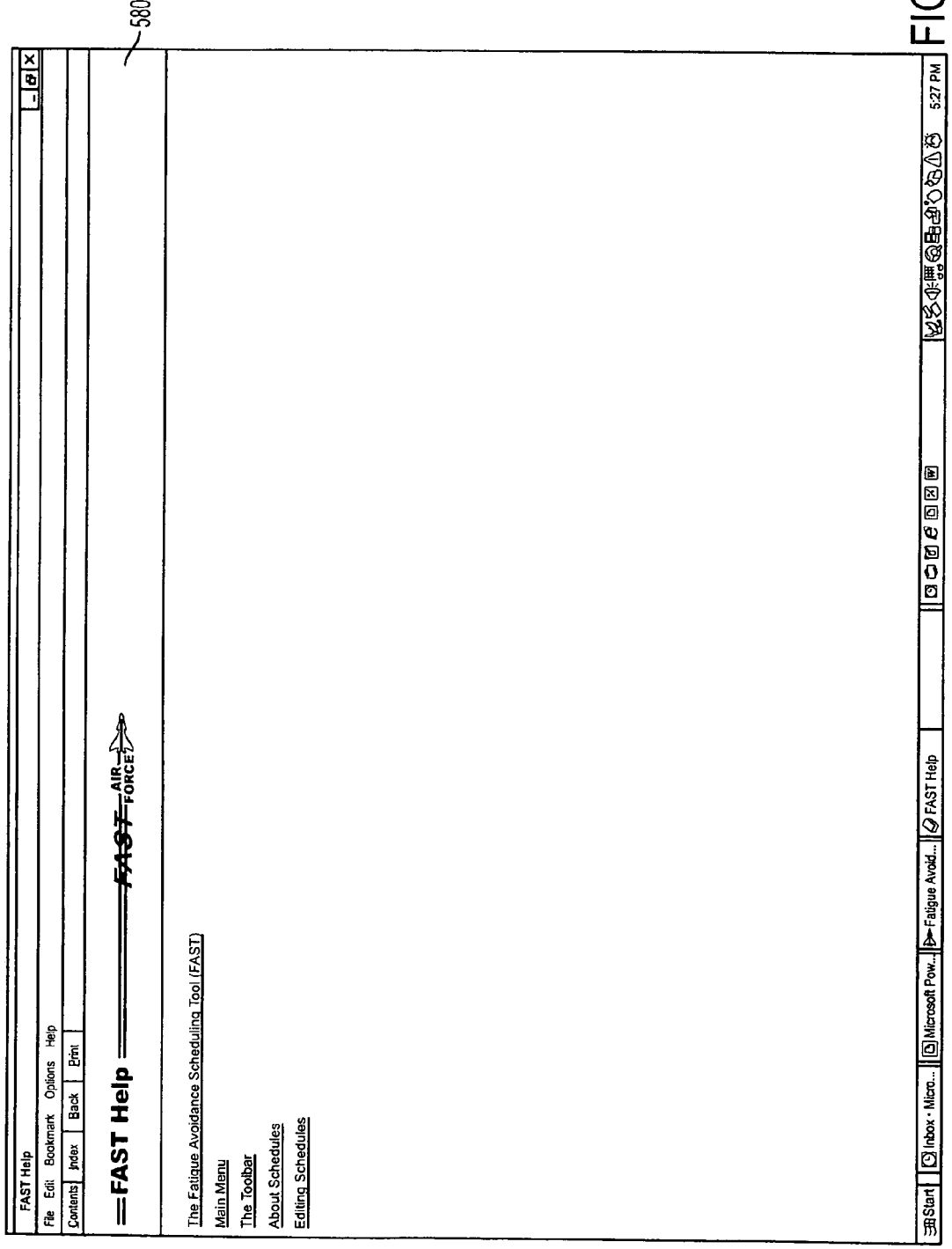
FIG. 48 is a help menu screen of the interface for the system for evaluating the effectiveness of a person to perform a task according to the present invention.

The WINDOW option in the main toolbar 502 presents the drop-down screen 574, shown in FIG. 46, when selected in order to provide the user with a choice of the arrangement of multiple windows and the current window selection. The screen 574 may include options for arranging the windows in a cascade manner or tiled horizontally or vertically. FIG. 47 illustrates an example of two schedules 576 and 578 tiled horizontally. Such an arrangement provides the user with an easy way to visually compare two schedules.

The last option on the main toolbar 502 is the HELP option. Selection of the HELP option presents a user with the Help menu screen 580, illustrated in FIG. 48. The Help menu screen 580 shows five help options: "The Fatigue Avoidance Scheduling Tool (FAST)," "Main Menu," "The Toolbar," "About Schedules," and "Editing Schedules."

Selection of the "The Fatigue Avoidance Scheduling Tool (FAST)" option brings up the help screen 582, as shown in FIG. 49, which presents the user with the underlying concepts behind the system and interface. Links may be provided to more detailed information, such as circadian rhythms and the details of the System and Method for Evaluating Task Effectiveness Based on Sleep Pattern.

Figure 50:
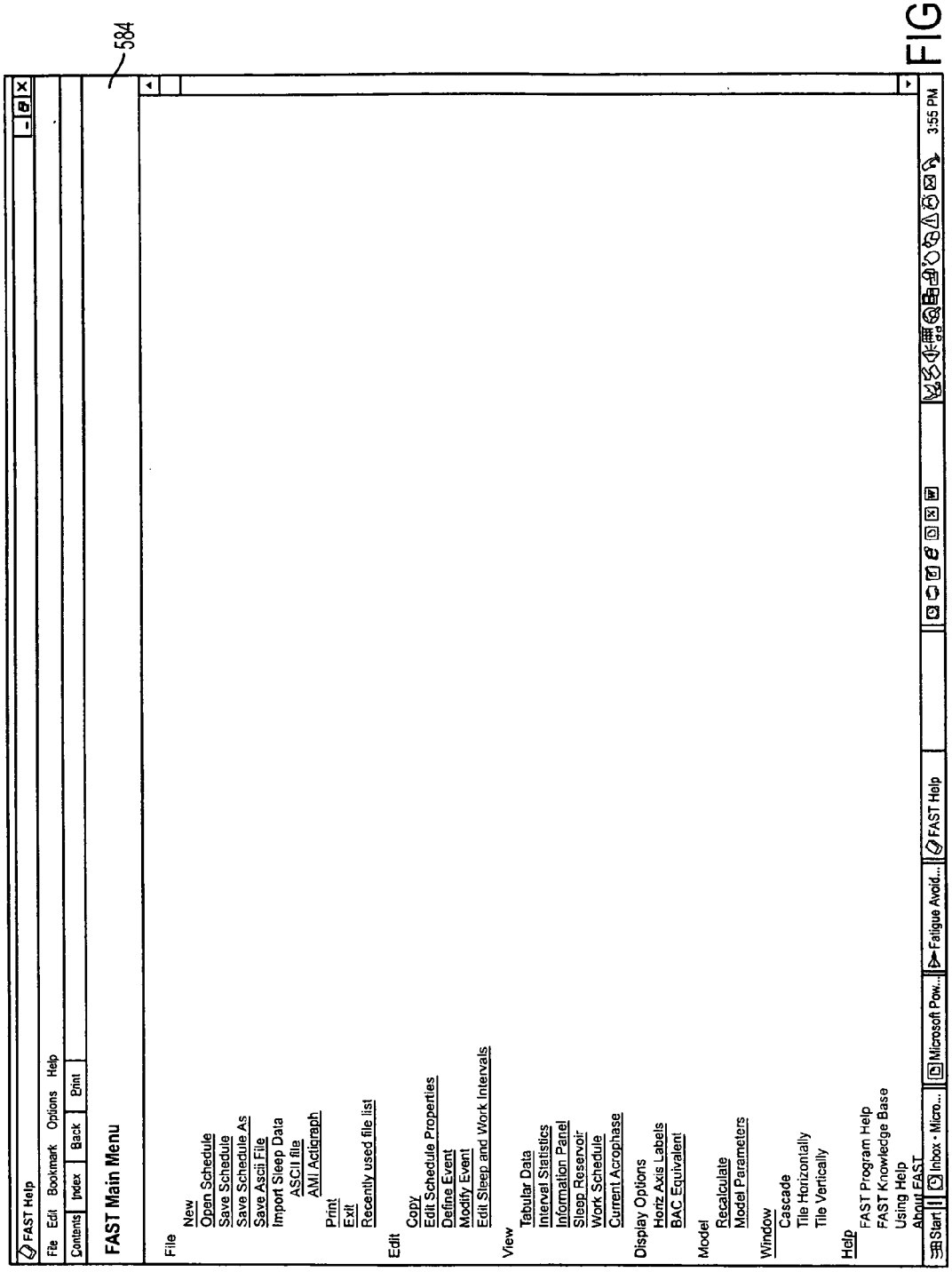
FIG. 50 is a FAST main menu screen displayed by selecting the main menu option from the screen shown in FIG. 48, for the interface for the system for evaluating the effectiveness of a person to perform a task according to the present invention.

The "Main Menu" option in the Help menu screen 580 produces the main menu screen 584 as shown in FIG. 50. The main menu screen 584 provides the user with detailed information concerning each of the options available through the main toolbar 502.

Figure 51:
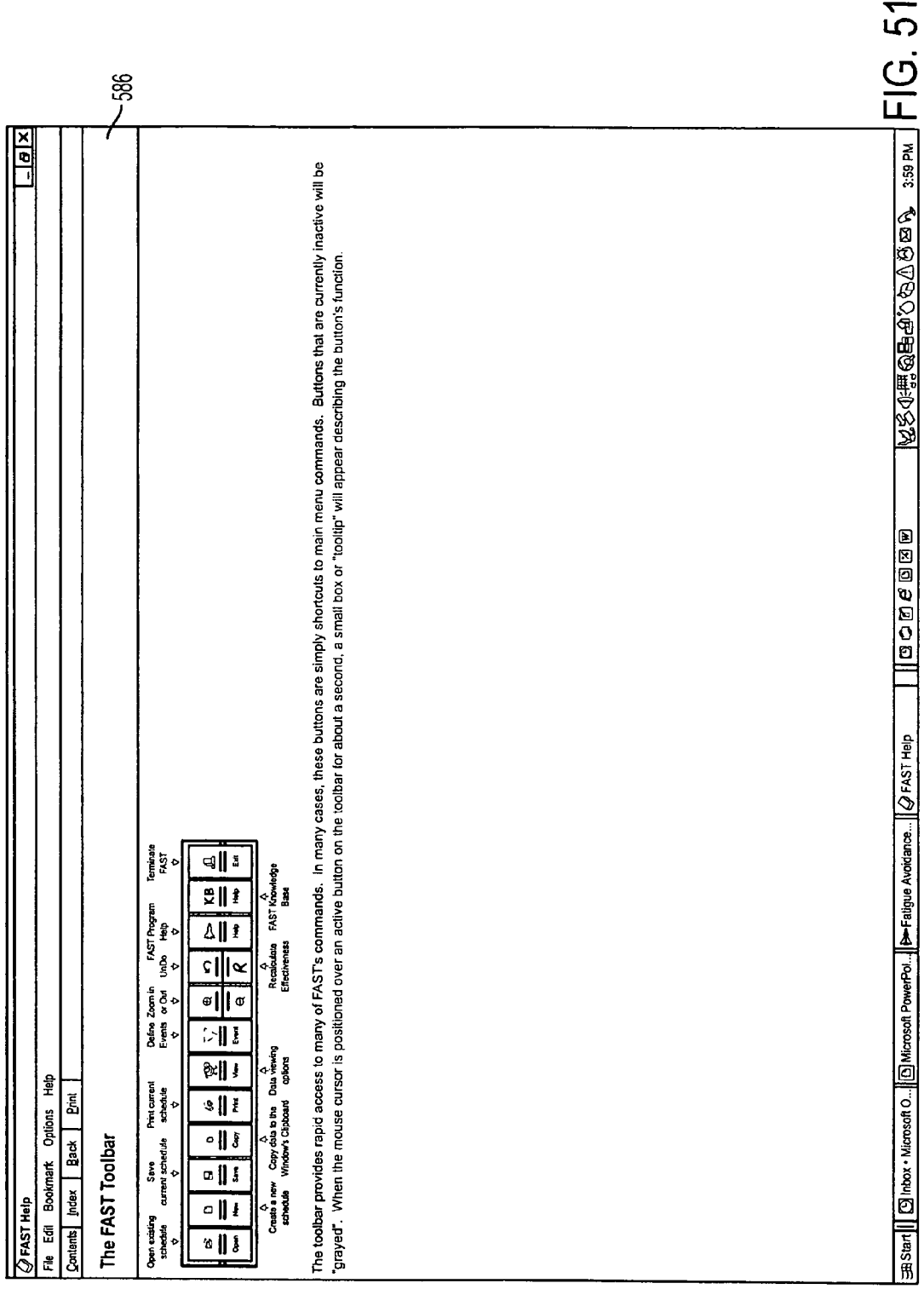
FIG. 51 is FAST toolbar screen displayed by selecting the toolbar option from the screen shown in FIG. 48, for the interface for the system for evaluating the effectiveness of a person to perform a task according to the present invention.

The Toolbar option in the Help menu screen 580 provides help information concerning the secondary toolbar 504 in toolbar help screen 586 shown in FIG. 51, and explains that some of the secondary toolbar options are shortcuts to main toolbar 502 options. Options that are inactive, i.e. not available at a particular point in time, appear in gray as opposed to available options that appear in black.

Figure 52:
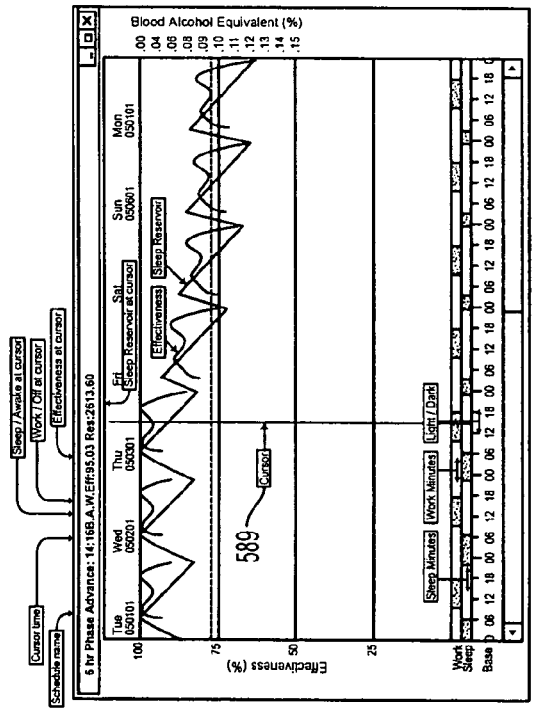
FIG. 52 is an about schedules screen displayed by selecting the about schedules option from the screen shown in FIG. 48, for the interface for the system for evaluating the effectiveness of a person to perform a task according to the present invention.

When the "About Schedules" option in Help menu screen 580 is selected the About Schedules Help Screen 588, shown in FIG. 52, is displayed. The components of a schedule screen are explained in screen 588, and links to more detailed information may be provided. Referring to FIG. 52, the representative schedule has markers explaining the multiple elements of the schedule.

The upper status line of the schedule includes a schedule name, a time indicator that corresponds to the location of the cursor 589 on the schedule, an indication of whether the schedule is in a sleep or wake period at the cursor location, an indication of whether the cursor is in a work section of the schedule, the individual's effectiveness at the cursor location, and the balance of the sleep reservoir at the cursor location. As the cursor is moved across the schedule, all the foregoing information, except for the schedule name, change.

Inside the schedule, both the effectiveness and the balance of the sleep reservoir may be plotted. The base axis of the schedule includes a visual indicator of the work cycle and the sleep/wake cycle. The bottom of the schedule can show different time indicators on the horizontal axis. These time indicators include the base time, which is the time at the location where a task originated, the elapsed time beginning at midnight on the first day, Zulu time, which is the time at the Prime Meridian, and local time, which is the time at the starting location of the schedule.

Figure 53:
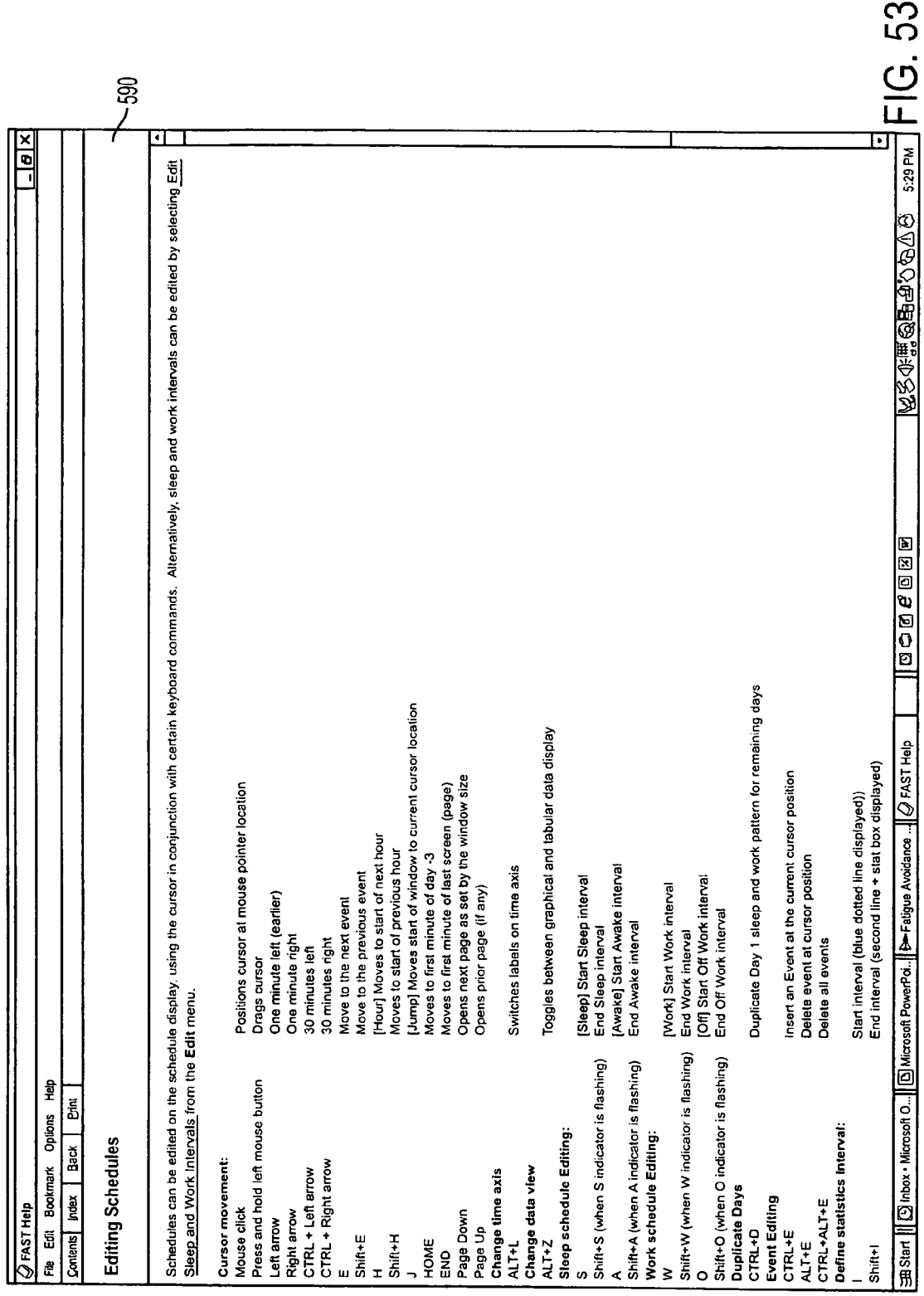
FIG. 53 is an edit schedules help menu screen displayed by selecting the editing schedules option from the screen shown in FIG. 48, for the interface for the system for evaluating the effectiveness of a person to perform a task according to the present invention.

The last option in Help menu screen 580 is the "Edit Schedules" help menu option, which produces the help menu 590, shown in FIG. 53, when selected. Help menu 590 explains the specific keystroke commands that may be employed to edit schedule information.

Figure 54:
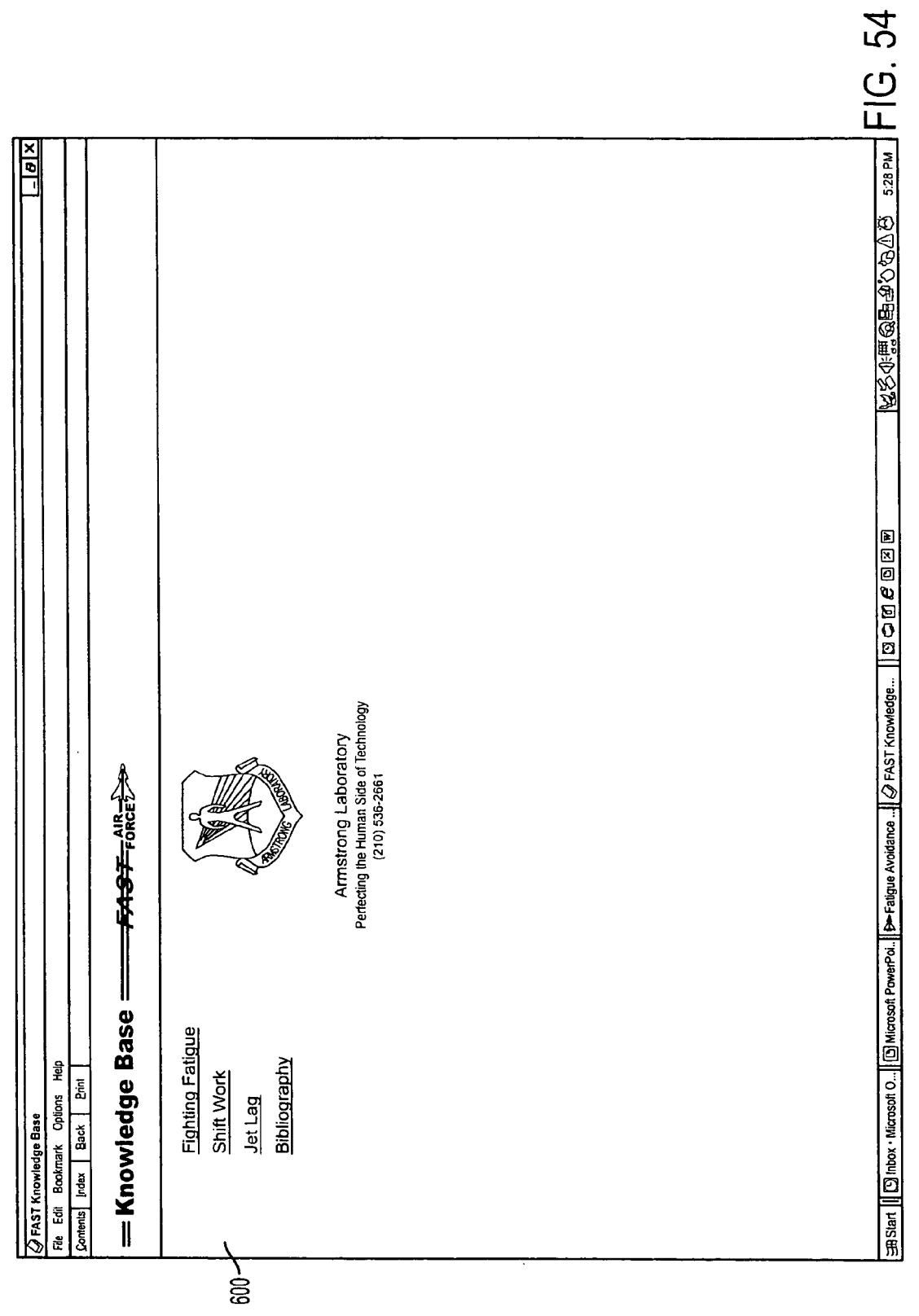

The Help menu screen 580 may optionally (not shown) include a link to a knowledge base, which, when selected, causes the system to open a knowledge base menu screen 600, illustrated in FIG. 54. The knowledge base menu screen 600 contains links to materials that provide additional relevant information to the user.

Figure 55:
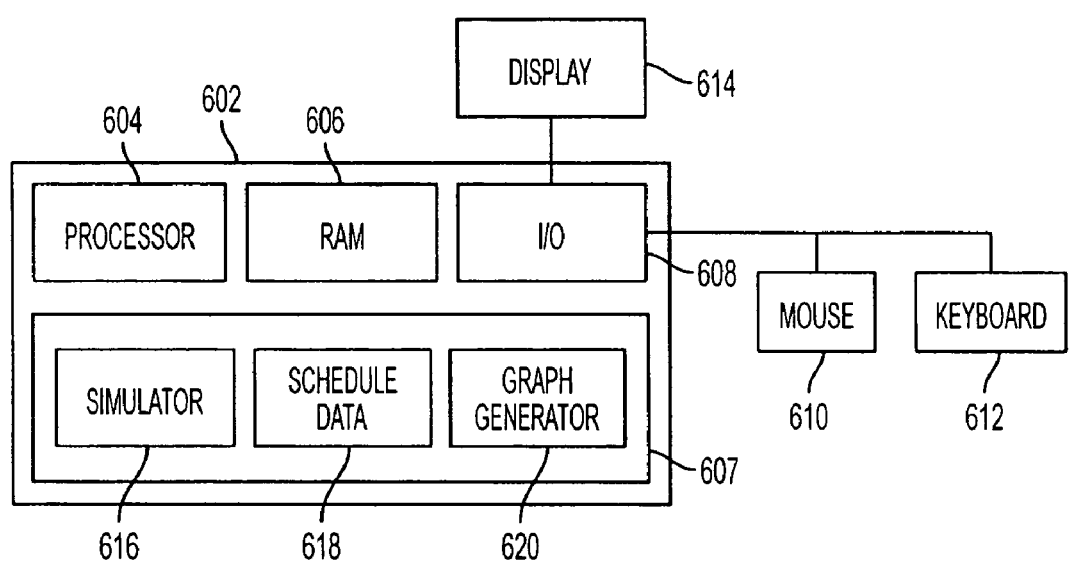
FIG. 55 illustrates a block diagram of a system according to an embodiment of the invention.

FIG. 55 illustrates a block diagram of a system 602 according to an embodiment of the invention. System 602 may include a processor 604, optional RAM 606, memory 607, and I/O 608 for communicating with input and output devices such as mouse 610, keyboard 612 and display 614. Memory 607 may store data and software such as a simulator engine 616, sleep schedule data 618, and a graph generator 620. Responsive to information displayed on display screen 614, a user may enter or modify sleep schedule data 618 (including metadata parameters) using mouse 610, keyboard 612 or any other input device. Simulator 616 may recalculate the sleep model (described above) using the new/modified parameters, and send the output to graph generator 620, which generates and sends the graphical results to display 614.

Using the interface, toolbars, and associated tools, a user is provided an easy and intuitive means for manipulating and interpreting the System and Method for Evaluating Task Effectiveness Based on Sleep Pattern. The plotted schedules created and displayed using the interface of the present invention provide the user with visual representations of schedules and the results of manipulations of the schedules so that the effectiveness of an individual to perform a task can be predicated and controlled. For instance a user can easily compare different sleep patterns for an individual over the course of a schedule to produce a particular effectiveness level at a specific time on the schedule. In view of the number of factors that can be varied using the interface of the present invention, the ability to view multiple schedules tiled horizontally provides the user with a simple method to compare different factors as they pertain to a specific task to thereby produce the desired effectiveness level.

Having described several embodiments of the system and method for predicting task effectiveness in accordance with the present invention, it is believed that other modifications, variations and changes will be suggested to those skilled in the art in view of the description set forth above. It is therefore to be understood that all such variations, modifications and changes are believed to fall within the scope of the invention as defined in the appended claims.

What is claimed is:

1. A method of evaluating the effectiveness of a person to perform a task based on a sleep pattern using the interface, said method performed by a computer system having a graphical user interface including a display and a user interface selection device, comprising the steps of:
   (i) receiving sleep pattern data for an individual;
   (ii) displaying a schedule based on the sleep pattern data;
   (iii) calculating and displaying a measure of task performance, wherein the measure is based at least in part on the received sleep pattern data;
   (iv) entering a parameter affecting the displayed schedule; and
   (v) displaying a second schedule for the individual, wherein the second schedule includes a recalculated measure of task performance responsive to the entered parameter,
   wherein step (iv) comprises entering event information corresponding to an aircraft takeoff or landing.

2. A method of evaluating the effectiveness of a person to perform a task based on a sleep pattern using the interface, said method performed by a computer system having a graphical user interface including a display and a user interface selection device, comprising the steps of:
   (i) receiving sleep pattern data for an individual;
   (ii) displaying a schedule based on the sleep pattern data;
   (iii) calculating and displaying a measure of task performance, wherein the measure is based at least in part on the received sleep pattern data;
   (iv) entering a parameter affecting the displayed schedule; and
   (v) displaying a second schedule for the individual, wherein the second schedule includes a recalculated measure of task performance responsive to the entered parameter,
   wherein step (iv) comprises entering event information corresponding to a travel waypoint.

3. A computer readable medium storing computer readable instructions to perform a method of evaluating the effectiveness of a person to perform a task based on a sleep pattern using the interface, comprising the steps of:
   (i) receiving sleep pattern data for an individual;
   (ii) displaying a schedule based on the sleep pattern data;
   (iii) calculating and displaying a measure of task performance, wherein the measure is based at least in part on the received sleep pattern data;
   (iv) entering a parameter affecting the displayed schedule; and
   (v) displaying a second schedule for the individual, wherein the second schedule includes a recalculated measure of task performance responsive to the entered parameter,
   wherein step (iv) comprises entering event information corresponding to aircraft takeoff or landing.

4. A computer readable medium storing computer readable instructions to perform a method of evaluating the effectiveness of a person to perform a task based on a sleep pattern using the interface, comprising the steps of:
   (i) receiving sleep pattern data for an individual;
   (ii) displaying a schedule based on the sleep pattern data;
   (iii) calculating and displaying a measure of task performance, wherein the measure is based at least in part on the received sleep pattern data;
   (iv) entering a parameter affecting the displayed schedule; and
   (v) displaying a second schedule for the individual, wherein the second schedule includes a recalculated measure of task performance responsive to the entered parameter,
   wherein step (iv) comprises entering event information corresponding to a travel waypoint.

* * * * *